United States Patent
Boyan et al.

(10) Patent No.: US 10,441,610 B2
(45) Date of Patent: Oct. 15, 2019

(54) PROTEIN DELIVERY FROM STEM CELL MICROCARRIERS

(75) Inventors: Barbara Dale Boyan, Richmond, VA (US); Zvi Schwartz, Richmond, VA (US); Christopher S. D. Lee, Atlanta, GA (US); Shirae Kerisha Leslie, Richmond, VA (US); Ramsey C. Kinney, Decatur, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 968 days.

(21) Appl. No.: 13/988,929

(22) PCT Filed: Nov. 23, 2011

(86) PCT No.: PCT/US2011/062068
§ 371 (c)(1),
(2), (4) Date: Jun. 23, 2014

(87) PCT Pub. No.: WO2012/071527
PCT Pub. Date: May 31, 2012

(65) Prior Publication Data
US 2014/0370111 A1    Dec. 18, 2014

Related U.S. Application Data

(60) Provisional application No. 61/416,463, filed on Nov. 23, 2010, provisional application No. 61/426,018, filed on Dec. 22, 2010.

(51) Int. Cl.
| | |
|---|---|
| *C12N 5/02* | (2006.01) |
| *C12N 5/00* | (2006.01) |
| *A61K 38/00* | (2006.01) |
| *A61K 35/28* | (2015.01) |
| *C12N 5/077* | (2010.01) |
| *C12N 5/0775* | (2010.01) |
| *A61K 9/50* | (2006.01) |
| *A61K 35/12* | (2015.01) |

(52) U.S. Cl.
CPC ............ *A61K 35/28* (2013.01); *A61K 9/5036* (2013.01); *C12N 5/0655* (2013.01); *C12N 5/0667* (2013.01); *A61K 2035/128* (2013.01); *C12N 2500/25* (2013.01); *C12N 2500/32* (2013.01); *C12N 2500/34* (2013.01); *C12N 2500/38* (2013.01); *C12N 2501/15* (2013.01); *C12N 2501/155* (2013.01); *C12N 2501/39* (2013.01); *C12N 2533/74* (2013.01)

(58) Field of Classification Search
None
See application file for complete search history.

(56) References Cited

U.S. PATENT DOCUMENTS

| | | | | |
|---|---|---|---|---|
| 8,202,701 B2 * | 6/2012 | Boyan | .................. | C12N 5/0012 |
| | | | | 435/174 |
| 9,642,914 B2 * | 5/2017 | Alsberg | ................. | A61K 47/36 |
| 2010/0215715 A1 * | 8/2010 | Han | ....................... | A61K 35/12 |
| | | | | 424/423 |

FOREIGN PATENT DOCUMENTS

| | | | |
|---|---|---|---|
| WO | WO 2011137292 | * | 4/2010 |
| WO | WO 2012/071527 | | 5/2012 |

OTHER PUBLICATIONS

Zheng et al., J of Biomed. Mater. Res, 2010, v.93 pp. 783-792).*
Lee et al., Tissue Engineer., 2008, v.14 pp. 1843-1851.*
European Patent Application No. 11843022.2 Official Communication dated Oct. 25, 2016 Regarding Consultation by telephone with applicant representative; 3 pgs.
Canadian Patent Application No. 2,818,894 Office Action dated Mar. 11, 2016; 4 pgs.
European Patent Application No. 11843022.2 Official Communication dated Oct. 21, 2015; 6 pgs.
Israeli Application No. 226501 Office Action dated Dec. 12, 2015; 4pgs.
Canadian Patent Application No. 2,818,894 Office Action dated Dec. 30, 2014; 6 pgs.
European Patent Application No. 11843022.2 Official Communication dated Dec. 16, 2014; 4 pgs.
Diekman BO, et al. (2010) Chondrogenesis of adult stem cells from adipose tissue and bone marrow: induction by growth factors and cartilage-derived matrix. Tissue Eng Part A. 16:523-533.
Erickson GR, et al. (2002) Chondrogenic potential of adipose tissue-derived stromal cells in vitro and in vivo. Biochem Biophys Res Commun. 290(2):763-769.
Estes BT, et al. (2006) Potent induction of chondrocytic differentiation of human adipose-derived adult stem cells by bone morphogenetic protein 6. Arthritis Rheum. 54(4):1222-1232.
Lee CS, et al. (2012) Adipose stem cells can secrete angiogenic factors that inhibit hyaline cartilage regeneration. Stem Cell Res Ther. 3(4):35.
Moyer HR, et al. (2010) Alginate microencapsulation technology for the percutaneous delivery of adipose-derived stem cells. Ann Plast Surg. 65(5): 497-503.
Communication conveying Supplementary European Search Report dated Apr. 10, 2014 for European Patent Application No. 11843022.2 (Applicant—Georgia Tech Research Corporation // Inventors—Boyan et al.) (7 pages).

* cited by examiner

*Primary Examiner* — Michail A Belyavskyi
(74) *Attorney, Agent, or Firm* — Morris, Manning & Martin, LLP; Daniel E. Sineway, Esq.

(57) ABSTRACT

Disclosed are methods and compositions of microbead carriers for delivery of cells and other biologically active substances to diseased or damaged tissue in a subject in need thereof.

11 Claims, 26 Drawing Sheets
Specification includes a Sequence Listing.

MVM AT 2

PROTEIN DELIVERY FROM STEM CELL MICROCARRIERS

CROSS REFERENCE TO RELATED APPLICATIONS

This application claims the benefit of U.S. Provisional Patent Application No. 61/416,463, filed on Nov. 23, 2010, and U.S. Provisional Patent Application No. 61/426,018, filed on Dec. 22, 2010, and is a continuation-in-part of U.S. patent application Ser. No. 11/576,542, which is a 371 application of PCT/US2005/036202 filed Oct. 7, 2005, which claims priority to and benefit of U.S. Provisional Patent Application No. 60/617,560, filed on Oct. 8, 2004, and where permissible the content of each of these applications is herein incorporated by reference in its entirety.

STATEMENT REGARDING FEDERALLY SPONSORED RESEARCH OR DEVELOPMENT

This invention was made with government support under grant numbers DGE0644493 awarded by the National Science Foundation and W81XWH-08-1-0704 awarded by the United States Army Medical Research and Materiel Command. The government has certain rights in the invention.

BACKGROUND

Technical Field

Aspects of the disclosed subject matter are broadly direct to methods and compositions for producing encapsulated cells and methods of using encapsulated cells, for example, in cellular arrays, screening protocols, and methods of treatment.

Related Art

High Throughput Screening (HTS) has been in use for at least the past ten years to screen large numbers of potential chemical compounds that may have pharmaceutical efficacy or that may be precursors to pharmaceuticals. A given investigation may involve the screening of on the order of about 10,000 compounds per day. The screening methods typically involve conducting a chemical reaction in the presence of a test compound to determine the effect of the test compound on the reaction. For example, compounds can be tested for the ability to inhibit or catalyze a desired chemical reaction or enzyme.

Cell based assays are also used in screening assays. With cell based assays, an aliquot of cells is contacted with a test compound to determine whether the test compound produces a desired or expected change in the cells. The test compound producing a change in the cells can be selected for further characterization. Cell based assays have certain advantages over simple chemical reaction assays. In particular, cell based assays can provide more detail on the physiological action of a test compound including, for example, uptake by cells or bioavailability. Unfortunately, cell based assays are not easily incorporated into HTS assays because it is difficult to standardize the number of cells contacted with various test compounds. Without standardizing the number of cells per reaction, meaningful comparisons between compounds are difficult to assess.

Small aliquots of cells having a uniform numbers of cells would facilitate automated manipulation of the cells during HTS. Additionally, such aliquots would be amenable to transplantation into a host using minimally invasive techniques.

Accordingly, there is a need for methods and compositions to produce aliquots of cells having predictable sizes and numbers of cells.

SUMMARY

Aspects of the present disclosure are generally directed to encapsulated cells, methods of producing encapsulated cells and uses thereof. One aspect provides a method for producing microencapsulated cells comprising applying an electrostatic potential to a droplet of cells suspended in a first solution comprising one or more types of monomers, wherein the electrostatic potential is in an amount sufficient to disrupt the surface tension of the droplet; and dropping the droplet into a polymerization solution from a distance sufficient to produce a structure encapsulating the cells with an average diameter of less than about 200 μm. The polymerization solution comprises a polymerizing agent that promotes the polymerization of the one or more types of monomers and optionally, a nutrient osmolyte, for example about 150 mM glucose.

Another aspect provides a cellular array comprising encapsulated cells produced according the present disclosure.

Still another aspect provides methods of treatment using the disclosed encapsulated cells. In particular aspects, the encapsulated cells are injected directly into pathology sites to repair damaged tissue or to secrete cytokines, growth factors, proteins, or combinations thereof. Because the average diameter of the disclosed encapsulate cells is less than about 200 μm, the encapsulated cells will be minimally damaged by shear forces produced during injection. Microcapsules having a diameter greater than 250 μm tend to block needles used to deliver the microcapsules to a host. Accordingly, the disclosed microcapsules having a diameter of less than about 250 μm, typically less than about 200 μm can be delivered to a host via injection with a standard surgical needle in an amount sufficient to treat the host.

In another aspect, provided is a method of decreasing expression, production, or secretion of an angiogenic factor by mesenchymal stem cells, comprising contacting the mesenchymal stem cells with a chondrogenic medium under suitable conditions, whereby contact with the chondrogenic medium decreases the expression, production or secretion of the angiogenic factor by the mesenchymal stem cells.

In another aspect, provided is a method of decreasing an inhibitory effect of mesenchymal stem cells on chondrogenic gene expression in a chondrocyte, wherein mesenchymal stem cells are in proximity to the chondrocyte, comprising contacting the mesenchymal stem cells with a chondrogenic medium under suitable conditions, whereby contacting the mesenchymal stem cells with the chondrogenic medium decreases the expression, production, or secretion of an angiogenic factor by the mesenchymal stem cells, thereby decreasing the inhibitory effect on chondrogenic gene expression in the chondrocyte.

In another aspect, provided is a method of decreasing an inhibitory effect of mesenchymal stem cells on proteoglycan synthesis in a chondrocyte, wherein mesenchymal stem cells are in proximity to the chondrocyte, comprising contacting the mesenchymal stem cells with a chondrogenic medium under suitable conditions, whereby contacting the mesenchymal stem cells with the chondrogenic medium decreases the expression, production, or secretion of an angiogenic factor by the mesenchymal stem cells, thereby decreasing the inhibitory effect on proteoglycan synthesis in the chondrocyte.

In another aspect, provided is a method of decreasing an inhibitory effect of mesenchymal stem cells on chondrocyte proliferation, wherein mesenchymal stem cells are in proximity to the chondrocyte, comprising contacting the mesenchymal stem cells with a chondrogenic medium under suitable conditions, whereby contacting the mesenchymal stem cells with the chondrogenic medium decreases the expression, production, or secretion of an angiogenic factor by the mesenchymal stem cells, thereby decreasing the inhibitory effect on chondrocyte proliferation.

In another aspect, provided is a method of decreasing a deleterious effect of mesenchymal stem cells on chondrocyte phenotype, wherein mesenchymal stem cells are in proximity to the chondrocyte, comprising contacting the mesenchymal stem cells with a chondrogenic medium under suitable conditions, whereby contacting the mesenchymal stem cells with the chondrogenic medium decreases the expression, production, or secretion of an angiogenic factor by the mesenchymal stem cells, thereby decreasing the deleterious effect on chondrocyte phenotype.

In another aspect, provided is a method of decreasing an apoptotic effect of mesenchymal stem cells on a chondrocyte, wherein mesenchymal stem cells are in proximity to the chondrocyte, comprising contacting the mesenchymal stem cells with a chondrogenic medium under suitable conditions, whereby contacting the mesenchymal stem cells with the chondrogenic medium decreases the expression, production, or secretion of an angiogenic factor by the mesenchymal stem cells, thereby decreasing the apoptotic effect on the chondrocyte.

In another aspect, provided is a method of increasing a stimulatory effect of mesenchymal stem cells on chondrogenic gene expression in a chondrocyte, wherein mesenchymal stem cells are in proximity to the chondrocyte, comprising contacting the mesenchymal stem cells with a chondrogenic medium under suitable conditions, whereby contacting the mesenchymal stem cells with the chondrogenic medium increases the expression, production, or secretion of chondrogenic factors by the mesenchymal stem cells, thereby increasing the stimulatory effect on chondrogenic gene expression in the chondrocyte.

In another aspect, provided is a method of increasing a stimulatory effect of mesenchymal stem cells on proteoglycan synthesis in a chondrocyte, wherein mesenchymal stem cells are in proximity to the chondrocyte, comprising contacting the mesenchymal stem cells with a chondrogenic medium under suitable conditions, whereby contacting the mesenchymal stem cells with the chondrogenic medium increases the expression, production, or secretion of chondrogenic factors by the mesenchymal stem cells, thereby increasing the stimulatory effect on proteoglycan synthesis in the chondrocyte.

In another aspect, provided is a method of increasing a stimulatory effect of mesenchymal stem cells on chondrocyte proliferation, wherein mesenchymal stem cells are in proximity to the chondrocyte, comprising contacting the mesenchymal stem cells with a chondrogenic medium under suitable conditions, whereby contacting the mesenchymal stem cells with the chondrogenic medium increases the expression, production, or secretion of chondrogenic factors by the mesenchymal stem cells, thereby increasing the stimulatory effect on chondrocyte proliferation.

In an aspect, provided is a composition comprising injectable biodegradable polymeric hydrogel microbeads, wherein the microbeads comprise mesenchymal stem cells previously contacted with chondrogenic medium under suitable conditions, whereby contact with the chondrogenic medium inhibited the expression, production, or secretion of an angiogenic factor or stimulated the expression, production, or secretion of a chondrogenic factor, or a combination of both, by the mesenchymal stem cells.

In another aspect, provided is a composition comprising injectable biodegradable polymeric hydrogel microbeads, wherein the microbeads comprise mesenchymal stem cells in contact with a chondrogenic medium under suitable conditions, whereby contact with the chondrogenic medium inhibits the expression, production, or secretion of an angiogenic factor or a hypertrophic factor or both, or stimulates the expression, production, or secretion of a chondrogenic factor or an anti-hypertrophic factor or both by the mesenchymal stem cells.

In another aspect, provided is a method of repairing cartilage in a subject diagnosed with diseased or damaged cartilage, comprising administering to a subject a therapeutically effective amount of a composition comprising injectable biodegradable polymeric hydrogel microbeads, wherein the microbeads comprise mesenchymal stem cells previously contacted with a chondrogenic medium under suitable conditions, whereby contact with the chondrogenic medium inhibited the expression, production, or secretion of an angiogenic factor or stimulated the expression, production, or secretion of a chondrogenic factor, or a combination of both, by the mesenchymal stem cells.

In another aspect, provided is a method of repairing cartilage in a subject diagnosed with diseased or damaged cartilage, comprising administering to a subject a therapeutically effective amount of a composition comprising injectable biodegradable polymeric hydrogel microbeads, wherein the microbeads comprise mesenchymal stem cells in contact with a chondrogenic medium under suitable conditions, whereby contact with the chondrogenic medium inhibits the expression, production, or secretion of an angiogenic factor or a hypertrophic factor or both, or stimulates the expression, production, or secretion of a chondrogenic factor or an anti-hypertrophic factor or both, by the mesenchymal stem cells.

In another aspect, provided is a method of controlling release of a biologically active composition from a biodegradable polymeric hydrogel microbead, comprising controlling the rate of degradation of the polymeric hydrogel, wherein the polymeric hydrogel is degraded by hydrolysis, by un-crosslinking of the polymeric hydrogel, or by a combination of both.

In another aspect, provided is a composition comprising injectable biodegradable polymeric hydrogel microbeads, wherein the microbeads comprise mesenchymal stem cells previously contacted with an osteogenic medium under suitable conditions, whereby contact with the osteogenic medium inhibited the expression, production, or secretion of an angiogenic factor by the mesenchymal stem cells.

In another aspect, provided is a composition comprising injectable biodegradable polymeric hydrogel microbeads, wherein the microbeads comprise mesenchymal stem cells previously contacted with an osteogenic medium under suitable conditions, whereby contact with the osteogenic medium increases the expression, production, or secretion of an osteogenic factor by the mesenchymal stem cells.

BRIEF DESCRIPTION OF THE FIGURES

FIGS. 6A-D show effects of ASC-secreted VEGF-A and FGF-2 on chondrocytes. (A) Schematic outlining chondrocytes treated with ASC-conditioned medium with VEGF-A and FGF-2 neutralizing antibodies and assayed for (B) [$^{35}$S]-sulfate incorporation, (C) caspase-3 activity, and (D) [$^{3}$H]-thymidine incorporation (n=6±SE. *$p<0.05$ vs. control, #$p<0.05$ vs. ASCs).

DETAILED DESCRIPTION

Figure 1A:
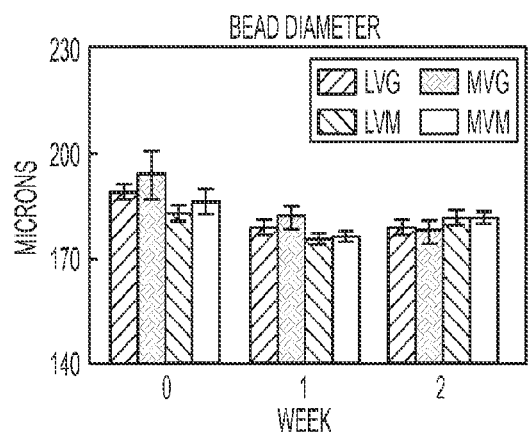
FIGS. 1A and 1B are bar graphs showing the average bead diameter of representative encapsulated cells to be 176.+−.2 to 194.+−.7 microns (A), and the average cell number per bead as 69.+−.2 to 80.+−.4 (B). There was no statistical difference in these parameters during the 2 week incubation time or between the different alginate formulations.

The present disclosure may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific angiogenic or chondrogenic factors, or to particular angiogenic or chondrogenic factors, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "an angiogenic factor" includes mixtures of angiogenic factors; reference to "a chondrogenic factor" includes mixtures of two or more such chondrogenic factors, and the like. It should also be noted that the term "or" is generally employed in its sense including "and/or" unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint and independently of the other endpoint.

In this specification and in the claims that follow, reference will be made to a number of terms which shall be defined to have the following meanings. Unless a contrary intention appears, the following terms refer to the indicated characteristics:

Definitions

"Optional" or "optionally" means that the subsequently described event or circumstance may or may not occur, and that the description includes instances where said event or circumstance occurs and instances where it does not. As used herein, by "subject" is meant an individual. Preferably, the subject is a mammal such as a primate, and more preferably a human. The term "subject" includes domesticated animals such as cats, dogs, etc., livestock (e.g., cattle, horses, pigs, sheep, goats, etc.), and laboratory animals (e.g., mice, rabbits, rats, gerbils, guinea pigs, etc.). As used herein, the terms "subject" and "patient" are interchangeable.

An "array", unless a contrary intention appears, includes any one-, two- or three-dimensional arrangement of addressable regions each having at least one unit of encapsulated cells optionally in combination with a particular chemical moiety or moieties (for example, biopolymers such as polynucleotide sequences) associated with that region. An array is "addressable" in that it has multiple regions of different moieties (for example, different cell types of chemicals) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces.

An "array layout" refers to one or more characteristics of the array or the features on it. Such characteristics include one or more of: feature positioning on the substrate; one or more feature dimension; some indication of an identity or function (for example, chemical or biological) of a moiety at a given location; how the array should be handled (for example, conditions under which the array is exposed to a sample, or array reading specifications or controls following sample exposure).

A "pulse jet" is a device which can dispense drops in the formation of an array. Pulse jets operate by delivering a pulse of pressure to liquid adjacent to an outlet or orifice such that a drop will be dispensed therefrom (for example, by a piezoelectric or thermoelectric element positioned in a same chamber as the orifice).

An array "package" may be the array plus only a substrate on which the array is deposited, although the package may include other features (such as a housing with a chamber).

A "chamber" references an enclosed volume (although a chamber may be accessible through one or more ports).

A "region" refers to any finite small area on the array that can be illuminated and any resulting fluorescence therefrom simultaneously (or shortly thereafter) detected, for example a pixel.

A "processor" references any hardware and/or software combination that will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station.

It will also be appreciated that throughout the present application that words such as "top," "upper," and "lower" are used in a relative sense only.

When one item is indicated as being "remote" from another, this is referenced that the two items are at least in different buildings, and may be at least one mile, ten miles, or at least one hundred miles apart. "Communication" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

Reference to a singular item, includes the possibility that there are plural of the same items present.

"May" means optionally.

Methods recited herein may be carried out in any order of the recited events which is logically possible, as well as the recited order of events.

All patents and other references cited in this application, are incorporated into this application by reference where permissible except insofar as they may conflict with those of the present application (in which case the present application prevails).

Methods of Encapsulation

Embodiments of the disclosure are directed to methods and compositions for encapsulating cells and methods of using the encapsulated cells. Suitable cells include, but are not limited to differentiated mesenchymal cells, epithelial cells, neural cells, endothelial cells, epithelial cells, myoblasts, chondrocytes, myoblasts, osteoblasts, osteoclasts, bone marrow cells, adult stem cells, embryonic stem cells, umbilical cord blood cells, fibroblasts, or a combination thereof. Although the disclosure discusses the use of alginate as an exemplary encapsulation matrix, it will be appreciated by one of skill in the art that any polymeric may be used to encapsulate the cells provided that the monomers can be polymerized by the addition of a polymerizing agent. The polymerizing agent can be chemical, ionic, temperature, electromagnetic energy, or a combination thereof.

A first embodiment provides a method for producing microencapsulated cells by applying an electrostatic potential to a droplet of cells suspended in a first solution in an amount sufficient to disrupt the surface tension of the droplet. The first solution includes one or more types of monomers that will polymerize and encapsulate the cells. Exemplary polymeric materials suitable for encapsulating cells include, but are not limited to alginate, agarose, hyaluronic acid, collagen, synthetic monomers, albumin, fibrinogen, fibronectin, vitronectin, laminin, dextran, dextran sulfate, chondroitin sulfate, dermatan sulfate, keratin sulfate, chitin, chitosan, heparan, heparan sulfate, or a combination thereof. Polymerization is initiated by dropping the droplet into a polymerization solution from a distance sufficient to produce a structure encapsulating the cells having a predetermined average diameter. Generally, the average diameter of the structure formed during the encapsulation process is less than about 200 µm, less than about 150 µm, less than about 100 µm, or between about 150 to about 250 µm. The drop distance needed to produce microcapsules with a predetermined diameter and optionally, a predetermined number of cells can be determined using the general equations provided in Example 1. Suitable drop distances are from about 1 to about 10 cm, typically about 5 cm. Drop distance and electrostatic potential can be varied in combination to obtain encapsulated cells having a diameter of less than about 250 µM. One of skill in the art will recognize that the cell density of the first solution can be adjusted alone or in combination with the parameters shown in the equations in Example 1, in particular with the drop distance to obtain microcapsules having a predetermine diameter and cell number. Drop distance refers to the distance the droplet of cells falls before contacting the polymerization solution.

A representative encapsulation matrix includes, but is not limited to alginate. Generally, the use of alginate as an immobilization matrix for cells involves mixing a suspension of the cells with a sodium alginate solution, whereafter the mixture is dripped into a polymerization solution containing a polymerizing agent, for example multivalent cations (usually $Ca^{++}$). The droplets form gel spheres instantaneously entrapping the cells in a three-dimensional lattice of ionically crosslinked alginate (Alginate as Immobilization Matrix for Cells" by Smidsrod and Skjak-Braek in Trends in Biotechnology, March 1990, Vol. 8, No. 3, pages 71-78). This immobilization procedure can be carried out under very mild conditions and is therefore compatible with most living cells. Generally, a 2% (w/v) solution of alginate in saline is sufficient for producing microcapsules having a diameter of less than about 200 μm, and less than about 100, 90, 80, or 70 total cells. The concentration of alginate con be varied to obtain a desired shape or size of encapsulated cells.

An exemplary polymerization solution comprises at least about 20 mM of a polymerizing agent such as $CaCl_2$. The amount of free $Ca^{++}$ can be standardized using calcium ion chelators such as EGTA and/or EDTA. For example, a solution of EGTA can be titrated $CaCl_2$ to obtain a solution having a desired concentration of free calcium. Other polymerizing agents include, but are not limited to divalent cations and or chemical catalysts. Alternatively, the polymerization agent can be heat, light, or other form of thermal or electromagnetic energy.

The polymerization solution also may contain a nutrient osmolyte. The term "nutrient osmolyte" refers to a solute that is nutrient for the cells that helps maintain the osmotic balance of the solution to protect the cells fro swelling, bursting, or dehydrating. Glucose is a suitable nutrient osmolyte that maybe used in the polymerization solution. The amount of glucose can be from about 50 to about 200 mM, typically about 150 mM.

A further embodiment provides a method of microencapsulating cells using alginate in combination with a second polymeric material, for example polyamino acids. Briefly, cells are suspended in sodium alginate in saline, and droplets containing cells are produced, for example by extruding the solution through a needle. An electrostatic potential is maintained between the droplets and the polymerization solution. Generally, about 6 kV is applied to obtain microcapsules having a diameter of less than about 200 μm.

Droplets of cell-containing alginate flow into calcium chloride in saline. The negatively charged alginate droplets bind calcium and form a calcium alginate gel. The microcapsules are washed in saline and incubated with a polyamino acid. Suitable polyamino acids include, but are not limited to poly-L-lysine, poly-L-ornithine, poly-L-arginine, poly-L-asparagine, poly-L-aspartic acid, poly-benzyl-L-aspartate, poly-S-benzyl-L-cysteine, poly-.gamma.-benzyl-L-glutamate, poly-S-CBZ-L-cysteine, poly-.epsilon.-CBZ-D-lysine, poly-.delta.CBZ-DL-ornithine, poly-O-CBZ-L-serine, poly-O-CBZ-D-tyrosine, poly(.gamma.-ethyl-L-glutamate), poly-D-glutamic acid, polyglycine, poly-.gamma.-N-hexyl L-glutamate, poly-L-histidine, poly (.alpha.,.beta.-[N-(2-hydroxyethyl)-DL-aspartamide]), poly-L-hydroxyproline Poly(.alpha.,.beta.-[N-(3-hydroxypropyl)-DL-aspartamide]), poly-L-isoleucine, poly-L-leucine, poly-D-lysine, poly-L-phenylalanine, poly-L-proline, poly-L-serine, poly-L-threonine, poly-DL-tryptophan, poly-D-tyrosine, or a combination thereof. In one embodiment, the positively charged poly-L-lysine and/or poly-L-ornithine displaces calcium ions and binds (ionic) negatively charged alginate, producing an outer poly-electrolyte membrane. A final coating of sodium alginate may be added by washing the microcapsules with a solution of sodium alginate, which ionically bonds to the poly-L-lysine and/or poly-L-ornithine layer. See U.S. Pat. No. 4,391,909 to Lim et al (all U.S. patents referenced herein are intended to be incorporated herein in their entirety). This technique produces what has been termed a "single-wall" microcapsule. Preferred microcapsules are essentially round, small, and uniform in size, for example having an average diameter of about 200 μm or less. Wolters et al., J. Appli Biomater. 3:281 (1992).

In a further embodiment, the alginate-polylysine microcapsules can then be incubated in a calcium chelator such as sodium citrate to solubilize any calcium alginate that has not reacted with poly-L-lysine, i.e., to solubilize the internal core of sodium alginate containing the cells, thus producing a microcapsule with a liquefied cell-containing core portion. See Lim and Sun, Science 210:908 (1980). Such microcapsules are referred to herein as having "chelated", "hollow" or "liquid" cores.

A "double-wall" microcapsule is produced by following the same procedure as for single-wall microcapsules, but prior to any incubation with sodium citrate, the microcapsules are again incubated with poly-1-lysine and sodium alginate.

A further embodiment provides microcapsules as described above having a final polymeric coating (e.g., polyethylene glycol (PEG)) or polyethylene oxide.

The encapsulating matrix may be formulated into a sponge-like material that is desirable for an implantable formulation. The matrices of the present invention may be formed into any shape by lyophilization or air drying in molds of the desired shape. Growth factors and/or therapeutic agents may be included in the matrix, and can include proteins originating from various animals including humans, microorganisms and plants, as well as those produced by chemical synthesis and using genetic engineering techniques. Such agents include, but are not limited to, biologically active substances such as growth factors such as, bFGF(FGF)-1), aFGF(FGF-2), EGF (epidermal growth factor), PDGF (platelet-derived growth factor), IGF (insulin-like growth factor), TGF-.beta. 1 through 3, including the TGF-.beta. superfamily (BMPs, GDF-5, ADMP-1 and dpp); cytokines, such as various interferons, including interferon-alpha, -beta and -gamma, and interleukin-2 and -3; hormones, such as, insulin, growth hormone-releasing factor and calcitonin; non-peptide hormones; antibiotics; anti-cancer agents and chemical agents, such as, chemical mimetics of growth factors or growth factor receptors, and gene and DNA constructs, including cDNA constructs and genomic constructs.

In another embodiment, the agents include those factors, proteinaceous or otherwise, which are found to play a role in the induction or conduction of growth of bone, ligaments, cartilage or other tissues associated with bone or joints, such as for example, BMP and bFGF (FGF-2). One embodiment provides autologous or allogeneic cells encapsulated within the matrix. The autologous cells may be those naturally occurring in the donor or cells that have been recombinantly modified to contain one or more exogenous nucleic acids encoding desired protein products.

Alternative Polymeric Materials

The disclosed encapsulate cells can also contain water-soluble macromers, species, which are at once polymers and macromolecules capable of further polymerization. The macromers can be polymerized using a photoinitiator (such as a dye), optionally a cocatalyst, optionally an accelerator, or radiation in the form of visible or long wavelength UV light. The reaction occurs either by suspension polymerization or by interfacial polymerization. The polymer membrane can be formed directly on the surface of the biological material, or it can be formed on material which is already encapsulated.

Poly(ethylene oxide) (PEO) is and exemplary polymeric material that can be used with the disclosed encapsulated cells. The PEO chain is highly water soluble and highly flexible. Polymethylene glycol, on the other hand, undergoes rapid hydrolysis, while polypropylene oxide is insoluble in water. PEO chains have an extremely high motility in water and are completely non-ionic in structure. The synthesis and characterization of PEO derivatives which can be used for attachment of PEO to various surfaces, proteins, drugs, etc. is known in the art. Other suitable polymers include poly (N-vinyl pyrrolidinone) and poly(ethyl oxazoline). These have been used to reduce interaction of cells with tissues. Water soluble ionic polymers, such as hyaluronic acid, can also be used to reduce cell adhesion to surfaces and can similarly be used.

Microcapsules

The methods of the present disclosure are intended for use with any microcapsule that contains living cells, for example cells secreting a desirable biological substance such as a hormone, protein, polysaccharide, or growth factor. One embodiment provides a microcapsule comprising an inner gel core containing the cells of interest, or a liquid core containing the cells of interest bounded by a semi-permeable membrane surrounding the cell-containing core. The inner core is preferably composed of a water-soluble gelling agent; preferably the water-soluble gelling agent comprises plural groups that can be ionized to form anionic or cationic groups. The presence of such groups in the gel allows the surface of the gel bead to be cross-linked to produce a membrane, when exposed to polymers containing multiple functionalities having a charge opposite to that of the gel.

Cells suspended in a gellable medium (such as alginate) may be formed into droplets using any suitable method as is known-in the art, including but not limited to emulsification (see e.g., U.S. Pat. No. 4,352,883), extrusion from a needle (see, e.g., U.S. Pat. No. 4,407,957; Nigam et al., Biotechnology Techniques 2:271-276 (1988)), use of a spray nozzle (Plunkett et al., Laboratory Investigation 62:510-517 (1990)), or use of a needle and pulsed electrical electrostatic voltage (see, e.g., U.S. Pat. Nos. 4,789,550; 5,656,468).

The water-soluble gelling agent is preferably a polysaccharide gum, and more preferably a polyanionic polymer. An exemplary water-soluble gelling agent is an alkali metal alginate such as sodium alginate. The gelling agent preferably has free acid functional groups and the semi-permeable membrane is formed by contacting the gel with a polymer having free amino functional groups with cationic charge, to form crosslinks between the free amino acids of the polymer and the acid functional groups. Suitable polymers include poly-L-lysine, poly-L-ornithine, poly-L-arginine, poly-L-asparagine, poly-L-aspartic acid, poly-benzyl-L-aspartate, poly-S-benzyl-L-cysteine, poly-.gamma.-benzyl-L-glutamate, poly-S-CBZ-L-cysteine, poly-.epsilon.-CBZ-D-lysine, poly-.delta.-CBZ-DL-ornithine, poly-O-CBZ-L-serine, poly-O-CBZ-D-tyrosine, poly(.gamma.-ethyl-L-glutamate), poly-D-glutamic acid, polyglycine, poly-.gamma.-N-hexyl L-glutamate, poly-L-histidine, poly(.alpha.,.beta.-[N-(2-hydroxyethyl)-DL-aspartamide]), poly-L-hydroxyproline Poly (.alpha.,.beta.-[N-(3-hydroxypropyl)-DL-aspartamide]), poly-L-isoleucine, poly-L-leucine, poly-D-lysine, poly-L-phenylalanine, poly-L-proline, poly-L-serine, poly-L-threonine, poly-DL-tryptophan, poly-D-tyrosine, or a combination thereof.

A particularly preferred microcapsule contains cells immobilized in a core of alginate optionally with a second polymeric coating, for example a poly-lysine coating; such microcapsules may comprise an additional external alginate layer to form a multi-layer to form a multi-layer alginate-polylysine-alginate microcapsule. See U.S. Pat. No. 4,391,909 to Lim et al., the contents of which are incorporated by reference herein in their entirety.

When desired, the microcapsules may be treated or incubated with a physiologically acceptable salt such as sodium sulfate or like agents, in order to increase the durability of the microcapsule, while retaining or not unduly damaging the physiological responsiveness of the cells contained in the microcapsules. By "physiologically acceptable salt" is meant a salt that is not unduly deleterious to the physiological responsiveness of the cells encapsulated in the microcapsules. In general, such salts are salts that have an anion that binds calcium ions sufficiently to stabilize the capsule, without substantially damaging the function and/or viability of the cells contained therein. Sulfate salts, such as sodium sulfate and potassium sulfate, are preferred, and sodium sulfate is most preferred. The incubation step is carried out in an aqueous solution containing the physiological salt in an amount effective to stabilize the capsules, without substantially damaging the function and/or viability of the cells contained therein as described above. In general, the salt is included in an amount of from about 0.1 or 1 millimolar up to about 20 to 100 millimolar, most preferably about 2 to 10 millimolar. The duration of the incubation can be from about 1 to 10 minutes to about 1 or 2 hours, or more (e.g., over night). The temperature at which the incubation step is carried out is typically from about 4 degrees Celsius up to about 37 degrees Celsius, with room temperature (about 21 degrees Celsius) preferred.

When desired, liquefaction of the alginate gel may be carried out by any suitable method as is known in the art, such as ion exchange or chelation of calcium ion by chelators including, but not limited to sodium citrate, ethylene glycol bis(beta-aminoethylether)-N,N'tetraacetic acid (EGTA) or ethylenediaminetetraacetic acid (EDTA).

One embodiment provides microcapsules comprising a cell-containing core and optionally one or more layers surrounding the cell-containing core that permit the diffusion of nutrients, biologically active molecules and other selected products through the surface membrane and into the microcapsule core and can be used to limit the exchange of substances by size or charge. For example, the surface membrane can contain pores of a size that determines the molecular weight cut-off of the membrane. Where the microcapsule contains protein-secreting cells, the membrane pore size is chosen to allow the passage of the protein from the core to the external environment, but to exclude the entry of host immune response factors.

Arrays

A further embodiment provides an array comprising units of encapsulated cells deposited at addressable locations of a substrate. For example, each addressable location may contain one or more units of encapsulated cells or one or more test compounds. The unit of encapsulated cells can be a single bead of alginate encapsulated cells having an average diameter of less than about 200 μm and containing a predetermined number of cells. Each unit may contain approximately the same number of cells, typically plus or minus 40, 30, 20, or 10 or less cells. The encapsulated cells may be attached to the array substrate using any conventionally means, for example, polysaccharides, polyamino acids, or a combination thereof.

In an embodiment, the present method can include reacting multiple cellular arrays with standard mixtures or additions of test compounds. The method can then include comparing the amount of signal detected at each corresponding location or feature on two or more of the arrays. Standardizing the arrays can be based on this comparison.

In an embodiment, the present method can include detecting a first detectable signal (e.g., color) from the disclosed arrays and a second detectable signal from a standard mixture of the control compounds. The method can include comparing the strength of the first and second detectable signals. Quantitating the signal generated by the test compounds with control compounds can be based on this comparison.

Contacting can include any of a variety of known methods for contacting an array with a reagent, sample, or composition. For example, the method can include placing the array in a container and submersing the array in or covering the array with the reagent, sample, or composition. The method can include placing the array in a container and pouring, pipetting, or otherwise dispensing the reagent, sample, or composition onto features on the array. Alternatively, the method can include dispensing the reagent, sample, or composition onto features of the array, with the array being in or on any suitable rack, surface, or the like.

Detecting can include any of a variety of known methods for detecting a detectable signal from a feature or location of an array. Any of a variety of known, commercially available apparatus designed for detecting signals of or from an array can be employed in the present method. Such an apparatus or method can detect one or more of the detectable labels described herein below. For example, known and commercially available apparatus can detect colorimetric, fluorescent, or like detectable signals of an array. The methods and systems for detecting a signal from a feature or location of any array can be employed for monitoring or scanning the array for any detectable signal. Monitoring or detecting can include viewing (e.g., visual inspection) of the array by a person.

The disclosed arrays or compositions can be provided in any variety of common formats. The present encapsulated cells can be provided in a container, for example, as a liquid. In an embodiment, each of a plurality of disclosed encapsulated cells and arrays is provided in its own container (e.g., vial, tube, or well). The present disclosed encapsulated cells and arrays or compositions can be provided with materials for creating a cellular array or with a complete cellular array. In fact, the encapsulated cells can be provided bound to one or more features of a cellular array.

Arrays on a substrate can be designed for testing against any type of sample, whether a trial sample, reference sample, a combination of them, or a known mixture of test compounds. Any given substrate may carry one, two, four or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 50 cm$^2$, 20 cm$^2$, or even less than 10 cm$^2$, or less than 1 cm$^2$. For example, features may have widths (that is, diameter, for a round spot) in the range from a 10 µm to 1.0 cm. In other embodiments each feature may have a width in the range of 1.0 m to 1.0 mm, of 5.0 µm to 500 µm, or of 10 µm to 200 µm. Non-round features may have area ranges equivalent to that of circular features with the foregoing width (diameter) ranges. Feature sizes can be adjusted as desired, for example by using one or a desired number of pulses from a pulse jet to provide the desired final spot size.

Substrates of the arrays can be any solid support, a colloid, gel or suspension. Exemplary solid supports include, but are not limited to metal, metal alloys, glass, natural polymers, non-natural polymers, plastic, elastomers, thermoplastics, pins, beads, fibers, membranes, or combinations thereof.

At least some, or all, of the features are of different compositions (for example, when any repeats of each feature composition are excluded the remaining features may account for at least 5%, 10%, or 20% of the total number of features), each feature typically being of a homogeneous composition within the feature. Thus, certain feature may contain one type of cell encapsulated as described and a second feature may contain a second type of cell encapsulated as described. Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents by may not be present when, for example, photolithographic array fabrication processes are used. It will be appreciated though, that the interfeature areas, when present, could be of various sizes and configurations.

Array features will generally be arranged in a regular pattern (for example, rows and columns). However other arrangements of the features can be used when the user has, or is provided with, some means (for example, through an array identifier on the array substrate) or being able to ascertain at least information on the array layout (for example, any one or more of feature composition, location, size, performance characteristics in terms of significance in variations of binding patterns with different samples, or the like). Each array feature is generally of a homogeneous composition.

Each array may cover an area of less than 100 cm$^2$, or even less than 50 cm$^2$, 10 cm$^2$, or 1 cm$^2$. In many embodiments, the substrate carrying the one or more arrays will be shaped generally as a rectangular solid (although other shapes are possible), having a length of more than 4 mm and less than 1 m, for example, more than 4 mm and less than 600 mm, less than 400 mm, or less than 100 mm; a width of more than 4 mm and less than 1 m, for example, less than 500 mm, less than 400 mm, less than 100 mm, or 50 mm; and a thickness of more than 0.01 mm and less than 5.0 mm, for example, more than 0.1 mm and less than 2 mm, or more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either test compound solutions or units of encapsulated cells. Other drop deposition methods can also be used for fabrication.

One embodiment provides a method of spotting a uniform number of mammalian cells at a plurality of locations of a substrate comprising applying an electrostatic potential to a succession of droplets of cells suspended in a first solution comprising one or more types of monomers, wherein the electrostatic potential is in an amount sufficient to disrupt the surface tension of each successive droplet. Each droplet is then dropped into a polymerization solution from a distance sufficient to produce a structure encapsulating a predetermined number of cells, wherein each structure produced comprises the predetermined number of cells plus or minus forty or less cells. The encapsulated cells are positioned at an addressable location of the substrate.

Methods Employing Arrays

Following receipt by a user of an array made according to the present disclosure, it will typically be exposed to a sample (for example, a test compound) in any well known manner and the array is then read. Reading of the array may be accomplished by illuminating the array and reading the location and intensity of resulting fluorescence at multiple regions on each feature of the array. Arrays may be read by any method or apparatus known in the art, with other reading methods including other optical techniques (for example, detecting chemiluminescent or electroluminescent labels) or electrical techniques (where each feature is provided with an electrode to detect hybridization at the feature). Data from read arrays may be processed in any known manner, such as from commercially available array feature extraction software packages. A result obtained from the reading followed by a method of the present invention may be used in that form or may be further processed to generate a result such as that obtained by forming conclusions based on the pattern read from the array (such as whether or not a particular target sequence may have been present in the sample, or whether or not a pattern indicates a particular condition of an organism from which the sample came). A result of the reading (whether further processed or not) may be forwarded (such as by communication) to a remote location if desired, and received there for further use (such as further processing).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Detectable Labels

The disclosed encapsulated cells and arrays can include a detectable label, for example, a first detectable label. A second detectable label can be generated when the test compound contacts encapsulated cells on an array. Suitable labels include radioactive labels and non-radioactive labels, directly detectable and indirectly detectable labels, and the like. Directly detectable labels provide a directly detectable signal without interaction with one or more additional chemical agents. Suitable of directly detectable labels include colorimetric labels, fluorescent labels, and the like. Indirectly detectable labels interact with one or more additional members to provide a detectable signal. Suitable indirect labels include a ligand for a labeled antibody and the like.

Suitable fluorescent labels include: xanthene dyes, e.g., fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (RG6G5 or G5), 6-carboxyrhodamine-6G (R6G6 or G6), and rhodamine 110; Alexa dyes, e.g., Alexa-fluor-547; cyanine dyes, e.g., Cy3, Cy5 and Cy7 dyes; coumarins, e.g., umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes.

Cryopreservation of Cells

Methods of cryopreservation are well known in the art. In general terms, cryopreservation of animal cells involves freezing the cells in a mixture of a growth medium and another liquid that prevents water from forming ice crystals, and then storing the cells at liquid nitrogen temperatures (e.g., from about −80 to about −196.degree.C.).

One embodiment provides the cryopreservation of isolated and encapsulated mammalian cells in a cryopreservation medium. Another embodiment provides cryopreservation of isolated cells followed by microencapsulation of the cells prior to in vivo implantation.

Screening Methods

One of the several embodiments of the disclosure provides methods for identifying lead compounds, for example, using a combinatorial library of chemical compounds. Certain embodiments provide methods for identifying modulators of a target protein or cell function. As used herein the terms "test compound" refers to any molecule that may potentially inhibit or enhance the biological activity of a target protein, physiological pathway, or cellular function. The test compound can be a protein or fragment thereof, a small molecule, or even a nucleic acid molecule. The disclosure contemplates using lead compounds to help develop improved compounds, which includes not only comparisons with known inhibitors and activators of a target protein or cell function, but predictions relating to the structure of target molecules.

One embodiment provides a method for identifying lead compounds using a high through put assay to contact units of encapsulated cells comprising a predetermined and optionally standardized number of cells and selecting the test compound that promotes or causes a change in phenotype of the encapsulated cells compared to a control compound. The change in phenotype includes, but is not limited to, morphological changes, color changes, changes in DNA or protein synthesis, changes in transcription or gene expression, changes in secretion, or a combination thereof.

In another embodiment, small molecule libraries that are believed to meet the basic criteria for useful drugs can be screened to identify useful compounds. Screening of such libraries, including combinatorially generated libraries (e.g., expression libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Test compounds may include fragments or parts of naturally-occurring compounds, or may be found as active combinations of known compounds, which are otherwise inactive. Compounds isolated from natural sources, such as animals, bacteria, fungi, plant sources, including leaves and bark, and marine samples can be assayed as candidates for the presence of potentially useful pharmaceutical agents. It will be understood that the pharmaceutical agents to be screened could also be derived or synthesized from chemical compositions or man-made compounds. Thus, it is understood that the test compound identified by embodiments of the present disclosure may be peptide, polypeptide, polynucleotide, small molecule inhibitors, small molecule inducers, organic or inorganic, or any other compounds that may be designed based on known inhibitors or stimulators.

Other suitable test compounds include antisense molecules, catalytic nucleic acids such as ribozymes, and antibodies (including single chain antibodies), each of which would be specific for a target protein or cellular function of interest.

In addition to the compounds initially identified, other sterically similar compounds may be formulated to mimic the key portions of the structure of the test compounds, for example binding domains. Such compounds, which may include peptidomimetics of peptide modulators, may be used in the same manner as the initial test compounds.

An inhibitor or activator according to the present disclosure may be one which exerts its inhibitory or activating effect upstream, downstream, directly, or indirectly on a target protein or cellular function. In one embodiment, the inhibition or activation or a target protein by an identified test compound results a detectable phenotypic change of the encapsulated cells compared to that observed in the absence of the added test compound.

Assay endpoints may be assayed using standard methods such as FACS, FACE, ELISA, Northern blotting and/or Western blotting. Moreover, the assays can be conducted using genetically engineered cells, immortalized cells, cell lines, primary cell cultures, autologous cells, or a combination thereof.

Various cell lines can be utilized for such screening assays, including cells specifically engineered for this purpose. Suitable cells include, but are not limited to differentiated mesenchymal cells, epithelial cells, neural cells, endothelial cells, epithelial cells, myoblasts, chondrocytes, myoblasts, osteoblasts, osteoclasts, bone marrow cells, adult stem cells, embryonic stem cells, umbilical cord blood cells, fibroblasts, or a combination thereof. Cells can also be engineered to express or overexpress compounds or proteins in response to contact with a test compound. Furthermore, those of skill in the art will appreciate that stable or transient transfections, which are well known and used in the art, may be used in the disclosed embodiments.

For example, a transgenic cell comprising an expression vector can be generated by introducing the expression vector into the cell. The introduction of DNA into a cell or a host cell is well known technology in the filed of molecular biology and is described, for example, in Sambrook et al., Molecular Cloning 3.sup.rd Ed. (2001). Methods of transfection of cells include calcium phosphate precipitation, liposome mediated transfection, DEAE dextran mediated transfection, electroporation, ballistic bombardment, and the like. Alternatively, cells may be simply transfected with an expression vector using conventional technology described in the references and examples provided herein. The host cell can be a prokaryotic or eukaryotic cell, or any transformable organism that is capable of replicating a vector and/or expressing a heterologous gene encoded by the vector. Numerous cell lines and cultures are available for use as a host cell, and they can be obtained through the American Type Culture Collection (ATCC), which is an organization that serves as an archive for living cultures and genetic materials (www.atcc.org).

A host cell can be selected depending on the nature of the transfection vector and the purpose of the transfection. A plasmid or cosmid, for example, can be introduced into a prokaryote host cell for replication of many vectors. Bacterial cells used as host cells for vector replication and/or expression include DH5.alpha., JM109, KC8, as well as a number of commercially available bacterial hosts such as SURE® Competent Cells and SOLOPACK™ Gold Cells (STRATAGENE, La Jolla, Calif.). Alternatively, bacterial cells such as $E.$ $coli$ LE392 could be used as host cells for phage viruses. Eukaryotic cells that can be used as host cells include, but are not limited to, yeast, insects and mammals. Examples of mammalian eukaryotic host cells for replication and/or expression of a vector include, but are not limited to, HeLa, NIH3T3, Jurkat, 293, Cos, CHO, Saos, and PC12. Examples of yeast strains include, but are not limited to, YPH499, YPH500 and YPH501. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Depending on the assay, culture may be required. The cell is examined using any of a number of different physiologic assays. Alternatively, molecular analysis may be performed, for example, looking at protein expression, mRNA expression (including differential display of whole cell of polyA RNA) and others.

Methods of Treatment

Transplantation

Encapsulated cells produced according to the present disclosure may be transplanted into subjects as a treatment of pathologies including, but not limited to tissue damage, ischemia, insulin-dependent diabetes, heart attack, nerve damage, brain damage, bone damage, or cartilage repair. Such transplantation may be into the peritoneal cavity of the subject, or directly into a pathology site. Preferably, the encapsulated cells are injected directly into the site as needed. Because the average diameter of the encapsulate cells is less than about 200 µm, the encapsulated cells will be minimally damaged by shear forces produced during injection. Microcapsules having a diameter greater than 250 µm tend to block needles used to deliver the microcapsules to a host. Accordingly, the disclosed microcapsules having a diameter of less than about 250 µm, typically less than about 200 µm can be delivered to a host via injection with a standard surgical needle, for example a 14 gauge or 18 gauge needle, in an amount sufficient to treat the host.

The encapsulated cells can be genetically engineered to secrete a polypeptide needed to treat the pathology, for example insulin to control glycemia. It will be apparent to those skilled in the art that the quantity of microcapsules transplanted depends on the ability of the microcapsules to provide function in vivo. One skilled in the art will be able to determine suitable transplantation quantities of microcapsules, using techniques as are known in the art.

A further embodiment provides a method for treating a host comprising delivering encapsulated cells to host produced according to the present disclosure. For example, the encapsulated cells can produce cartilage or cartilage components in the host.

A further embodiment provides a method for repairing tissue in a host comprising administering encapsulated cells produced according the present disclosure, wherein the encapsulated cells produce tissue or tissue components in the host.

Stem cells may not be restricted to cell restoration alone but may also secrete one or more paracrine factors (proteins) that can stimulate surrounding cells and tissues to regenerate or proliferate. Further, by microencapsulating stem cells to form injectable biocompatible polymeric microbeads, a person of ordinary skill in the art can facilitate cell or tissue regeneration or proliferation or both by administering the stem cells into an area of diseased or damaged tissue, for example cartilage, and localizing and controlling the release of paracrine factors from the stem cells. Thus, microbeads comprising encapsulated stem cells can serve as a renewable (i.e., replenishable) reservoir at the site of a diseased or damaged tissue for producing and secreting one or more paracrine factors into the surrounding environment to stimulate cellular proliferation and/or tissue regeneration. Stem cells encapsulated in the microbeads can continually produce one dr more paracrine factors, and these factors can be temporarily stored within the microbeads and then released from the microbeads into the surrounding diseased or damaged tissue, for example cartilage.

An object of the present disclosure is to provide compositions comprising pre-conditioned mesenchymal stem cells and methods of use thereof for decreasing the production, expression, and secretion of angiogenic factors or hypertrophic factors or both, which are detrimental to cartilage formation and regeneration. Another object of the present disclosure is to provide compositions comprising pre-conditioned mesenchymal stem cells and methods of use thereof for increasing the production, expression, and secretion of chondrogenic factors or anti-hypertrophic factors or both, which promote cartilage formation and regeneration. As used herein, "pre-conditioned mesenchymal stem cells" are cells that have been in contact with (i.e., cultured in) a specific culture medium that is selected to increase or decrease the production, expression, and secretion of various paracrine factors by the mesenchymal stem cells, depending on the desired effect, before the stem cells are encapsulated in the microbeads.

In another aspect, the disclosed mesenchymal cells can be conditioned by contact with a specific culture medium that is selected to increase or decrease the production, expression, and secretion of various paracrine factors by the mesenchymal stem cells, depending on the desired effect, after the stem cells are encapsulated in the microbeads. Thus, mesenchymal stem cells can be conditioned in the microbead when in contact with a selected medium, for example, a chondrogenic medium.

Therefore, in one aspect, provided is a method of decreasing expression, production, or secretion of an angiogenic factor or a hypertrophic factor or both by mesenchymal stem cells, comprising contacting the mesenchymal stem cells with a chondrogenic medium under suitable conditions, whereby contact with the chondrogenic medium decreases the expression, production or secretion of the angiogenic factor or hypertrophic factor or both by the mesenchymal stem cells.

An example of a mesenchymal stem cell is an adipose stem cell.

Adipose stem cells are stem cells taken from adipose (fat) tissue in a mammal. In one aspect, the mammal is a human being. As disclosed above, cells can be encapsulated in biocompatible and biodegradable polymeric microbeads that are about 200 micrometers or less in diameter that can be injected into a subject. The microbead can be sized to include a number of cells that can be dispersed or suspended throughout the microbead so that the cells can be viable for from about seven days to about 14 days. For example, from about 60 to about 150 cells can be encapsulated in a disclosed microbead and remain viable for, for example, about 10 days. Thus, for example, about 100 adipose stem cells can be encapsulated in an injectable polymeric microbead and remain viable for about 10 days.

As used herein, "contacting the adipose stem cells with a chondrogenic medium" means putting the stem cells into a culture medium that promotes in the stem cells the expression, production, or secretion of factors that promote the formation of cartilage in a subject. In one aspect, mesenchymal stem cells, for example adipose stem cells, can contact a chondrogenic medium before the stem cells are encapsulated in a microbead. In another aspect, mesenchymal stem cells, for example adipose stem cells, can contact a chondrogenic medium after the stem cells are encapsulated in a microbead.

As used herein, a "chondrogenic medium" is a culture medium used to support and nourish cells, for example adipose stem cells, which can be used to produce paracrine factors that promote the formation of cartilage by increasing chondrocyte proliferation, chondrocyte gene expression, and proteoglycan synthesis by chondrocytes. A chondrogenic medium can comprise, for example, the following components:

Dulbecco's Modified Eagle Medium (DMEM) containing glucose at 1 g/L or 4.5 g/L;

Fetal Bovine Serum (FBS), which can increase production of angiogenic factors or decrease chondrogenic factors; ranges in concentration from 0% to 20% (v/v); used at 0% (v/v);

L-Proline used at 40 µg/mL;

ITS+ supplement which consists of 6.25 µg/mL bovine insulin, 6.25 µg/mL transferrin, 6.25 µg/mL selenous acid, 5.33 µg/mL linoleic acid, 1.25 mg/mL, and Bovine Serum Albumin, which can increase production of IGF-I, used at 1% (v/v);

Ascorbic acid or ascorbic acid-2-phosphate, which can increase production of chondrogenic factors or decrease angiogenic factors, ranges in concentration from 1 µg/mL to 1 mg/mL (or 0), used at 50 µg/mL;

Dexamethasone, which can increase production of chondrogenic factors or decrease angiogenic factors, ranges in concentration from $10^{-10}$ to $10^{-6}$ M (or 0 M), used at 100 nM;

24R,25-dihydroxyvitamin D3 (herein called "24,25"), which can increase production of chondrogenic factors or decrease angiogenic factors, ranges in concentration from $10^{-10}$ to $10^{-6}$ M (or 0 M), used at $10^{-7}$ M or 0 M;

TGF-β1 can increase production of angiogenic factors (when used alone or with 10% FBS) or chondrogenic factors, ranges in concentration from 0.2 ng/mL to 100 ng/mL, used at 10 ng/mL; and BMP-6 which can increase production of noggin or decrease production of VEGF-A, ranges in concentration from 1 ng/mL to 500 ng/mL, used at 100 ng/mL.

As used herein, "under suitable conditions" refers to the time duration, temperature, and pH conditions that a person of ordinary skill in the art would know support the growth and viability of the cultured stem cells. For example, adipose stem cells can be in contact with a chondrogenic medium for from about five days to about 14 days, including the number of days between five and 14, and remain viable. Thus, adipose stem cells can be in contact with chondrogenic medium for 5, 6, 7, 8, 9, 10, 11, 12, 13, and 14 days and remain viable. Further, cells can be cultured at around 37° C. at a neutral pH, in the range of 6.7 to about 7.3, and at about pH 7.0.

Angiogenic factors are substances that promote the formation of blood vessels. Examples of angiogenic factors include, but are not limited to, Vascular Endothelial Growth Factor-A (VEGF-A) and Fibroblast Growth Factor-2 (FGF-2).

Hypertrophic Factors are substances that induce chondrocytes to undergo hypertrophic or terminal differentiation, which is characterized by an increase in chondrocyte volume, an increase in alkaline phosphatase activity, and synthesis and secretion of type-X collagen, eventually leading to calcification and apoptosis. A non-limiting example of a hypertrophic factor is Fibroblast Growth Factor-18 (FGF-18).

It may be desirable to decrease the inhibitory effect of adipose stem cells on chondrogenic gene expression in chondrocytes because in order to replace damaged tissue such as cartilage, it is necessary for the chondrocytes to express certain genes relating to the expression and secretion of the factors needed for cartilage synthesis.

Accordingly, in another aspect, provided is a method of decreasing an inhibitory effect of adipose stem cells on chondrogenic gene expression in a chondrocyte, wherein adipose stem cells are in proximity to the chondrocyte, comprising contacting the adipose stem cells with a chondrogenic medium under suitable conditions, whereby contacting the adipose stem cells with the chondrogenic medium decreases the expression, production, or secretion of an angiogenic factor or a hypertrophic factor or both by the adipose stem cells, thereby decreasing the inhibitory effect on chondrogenic gene expression in the chondrocyte.

Proteoglycans are glycosylated proteins. A variety of proteoglycans are present in cartilage such as aggrecan, decorin, biglycan, fibromodulin, lumicanr, and lubricin. Because such proteoglycans are needed for cartilage synthesis, it is desirable to decrease the inhibitory effect of adipose stem cells on proteoglycan synthesis. Accordingly, in another aspect, provided is a method of decreasing an inhibitory effect of adipose stem cells on proteoglycan synthesis in a chondrocyte, wherein adipose stem cells are in proximity to the chondrocyte, comprising contacting the adipose stem cells with a chondrogenic medium under suitable conditions, whereby contacting the adipose stem cells with the chondrogenic medium decreases the expression, production, or secretion of an angiogenic factor or a hypertrophic factor or both by the adipose stem cells, thereby decreasing the inhibitory effect on proteoglycan synthesis in the chondrocyte.

In another aspect, provided is a method of decreasing an inhibitory effect of adipose stem cells on chondrocyte proliferation, wherein adipose stem cells are in proximity to the chondrocyte, comprising contacting the adipose stem cells with a chondrogenic medium under suitable conditions, whereby contacting the adipose stem cells with the chondrogenic medium decreases the expression, production, or secretion of an angiogenic factor or hypertrophic factor or both by the adipose stem cells, thereby decreasing the inhibitory effect on chondrocyte proliferation.

Chondrocytes exhibit observable physical and biochemical properties a "phenotype." Adipose stem cells may have certain undesirable effects on chondrocyte phenotype including, but not limited to, increased apoptosis, decreased proteoglycan production, decreased cartilage tissue synthesis, decreased chondrocyte proliferation, decreased gene expression of sox 9, aggrecan, type II collagen, and cartilage oligomeric matrix protein.

In another aspect, provided is a method of decreasing a deleterious effect of adipose stem cells on chondrocyte phenotype (i.e., the phenotype of a chondrocyte), wherein adipose stem cells are in proximity to the chondrocyte, comprising contacting the adipose stem cells with a chondrogenic medium under suitable conditions, whereby contacting the adipose stem cells with the chondrogenic medium decreases the expression, production, or secretion of an angiogenic factor or a hypertrophic factor or both by the adipose stem cells, thereby decreasing the deleterious effect on chondrocyte phenotype.

Apoptosis refers to programmed cell death resulting from a series of biochemical events in a cell. It is desirable to avoid apoptosis in chondrocytes in methods or therapies to generate new or replacement cartilage. Thus, in another aspect, provided is a method of decreasing an apoptotic effect of adipose stem cells on a chondrocyte, wherein adipose stem cells are in proximity to the chondrocyte, comprising contacting the adipose stem cells with a chondrogenic medium under suitable conditions, whereby contacting the adipose stem cells with the chondrogenic medium decreases the expression, production, or secretion of an angiogenic factor or hypertrophic factor or both by the adipose stem cells, thereby decreasing the apoptotic effect on the chondrocyte.

In order to synthesize cartilage, chondrocytes express certain genes, and it may be desirable to stimulate gene expression in a chondrocyte. Accordingly, in another aspect, provided is a method of increasing a stimulatory effect of adipose stem cells on chondrogenic gene expression in a chondrocyte, wherein adipose stem cells are in proximity to the chondrocyte, comprising contacting the adipose stem cells with a chondrogenic medium under suitable conditions, whereby contacting the adipose stem cells with the chondrogenic medium increases the expression, production, or secretion of chondrogenic factors or anti-hypertrophic factors or both by the adipose stem cells, thereby increasing the stimulatory effect on chondrogenic gene expression in the chondrocyte.

Examples of chondrogenic factors are factors which induce chondrogenesis, chondrocyte proliferation, and synthesis of extracellular matrix components and other proteins specific to cartilage. Such factors include, but are not limited to, TGF-$\beta$1, TGF-$\beta$2, TGF-$\beta$3, IGF-1, PTHrP, or a combination thereof. A non-limiting example of an anti-hypertrophic factor is Noggin.

Further provided is a method of increasing a stimulatory effect of adipose stem cells on proteoglycan synthesis in a chondrocyte, wherein adipose stem cells are in proximity to the chondrocyte, comprising contacting the adipose stem cells with a chondrogenic medium under suitable conditions, whereby contacting the adipose stem cells with the chondrogenic medium increases the expression, production, or secretion of chondrogenic factors or anti-hypertrophic factors or both by the adipose stem cells, thereby increasing the stimulatory effect on proteoglycan synthesis in the chondrocyte.

In certain situations, it is desirable to promote the proliferation of chondrocytes, particularly in instances where such cells are located close to damaged or diseased tissue and in which a clinician needs to promote the local growth of cartilage. Thus, in another aspect, provided is a method of increasing a stimulatory effect of adipose stem cells on chondrocyte proliferation, wherein adipose stem cells are in proximity to the chondrocyte, comprising contacting the adipose stem cells with a chondrogenic medium under suitable conditions, whereby contacting the adipose stem cells with the chondrogenic medium increases the expression, production, or secretion of chondrogenic factors or anti-hypertrophic factors or both by the adipose stem cells, thereby increasing the stimulatory effect on chondrocyte proliferation.

As discussed hereinabove, disclosed are injectable microbeads that can be used to deliver cells or other compositions to a subject. In another aspect, provided is a composition comprising injectable biodegradable polymeric hydrogel microbeads, wherein the microbeads comprise adipose stem cells previously contacted with a chondrogenic medium under suitable conditions, whereby contact with the chondrogenic medium inhibited the expression, production, or secretion of an angiogenic factor or a hypertrophic factor or both, and/or stimulated the expression, production, or secretion of a chondrogenic factor or anti-hypertrophic factor or both by the adipose stem cells. It is contemplated that contacting adipose stem cells with a chondrogenic medium (i.e., pre-conditioning adipose stem cells by culturing the stem cells in a chondrogenic medium) can (1) inhibit the expression, production, or secretion of an angiogenic factor or a hypertrophic factor or both, and (2) stimulate the expression, production, or secretion of a chondrogenic factor or anti-hypertrophic factor or both by the adipose stem cells.

In another aspect, provided is a composition comprising injectable biodegradable polymeric hydrogel microbeads, wherein the microbeads comprise mesenchymal stem cells, for example adipose stem cells, in contact with a chondrogenic medium under suitable conditions, whereby contact with the chondrogenic medium inhibits the expression, production, or secretion of an angiogenic factor or a hypertrophic factor or both, or stimulates the expression, production, or secretion of a chondrogenic factor or an anti-hypertrophic factor or both by the adipose stem cells.

As disclosed above, a microbead can comprise alginate (alginic acid) or other anionic polysaccharides (polymers) including, but not limited to, for example, polyactide-co-glycolide. The molecular weight of a disclosed microbead can be from about 50 kDa to about 400 kDa. For example, the molecular weight of a disclosed microbead can be 150 kDa. Further, each microbead can comprise from about 60 to about 150 cells. For example, each microbead can comprise about 100 adipose stem cells. The adipose stem cells can be homogenously suspended or admixed throughout the microbead in a chondrogenic medium, for example, and can remain viable for at least about five to 14 days. Thus, for example, 100 adipose stem cells encapsulated in a disclosed microbead can remain viable for about 10 days.

Further, the disclosed microbeads are a renewable reservoir for the disclosed paracrine factors that are expressed, produced, and secreted by the adipose stem cells. Thus, the microbeads can store and then release into surrounding diseased or damaged tissue, for example cartilage, paracrine factors, such as angiogenic factors, hypertrophic factors, chondrogenic factors, or anti-hypertrophic factors, or a combination thereof.

In another aspect, provided is a method of repairing cartilage in a subject diagnosed with diseased or damaged cartilage, comprising administering to a subject a therapeutically effective amount of a composition comprising injectable biodegradable polymeric hydrogel microbeads, wherein the microbeads comprise adipose stem cells preconditioned by previous contact with a chondrogenic medium under suitable conditions, whereby contact with the chondrogenic medium inhibited the expression, production, or secretion of an angiogenic factor or hypertrophic factor or both, or stimulated the expression, production, or secretion of a chondrogenic factor or anti-hypertrophic factor or both by the adipose stem cells.

As used herein, "therapeutically effective" means that the amount of the composition and the method of treating a damaged or diseased tissue, for example cartilage, in a human subject produced an expected result of amelioration of one or more symptoms, signs, or sequelae of the disease or disorder. Such amelioration only requires a reduction or alteration, not necessarily elimination, of the cause, symptoms, signs, or sequelae of a disease or disorder.

By a "therapeutically effective amount" of a compound as provided herein is meant a sufficient amount of the compound to provide the desired effect. The exact amount required will vary from subject to subject, depending on the species, age, and general condition of the subject, the severity of damage or disease (or underlying genetic defect) that is being treated, the particular compound used, its mode of administration, and the like. Thus, it is not possible to specify an exact "effective amount." However, an appropriate "effective amount" can be determined by one of ordinary skill in the art using only routine experimentation.

As disclosed above, the microbeads are about 200 micrometers or less in diameter. Thus, because of their small size, the disclosed microbeads can be injected into the target area of diseased or damaged cartilage in a subject through a standard sterile needle, for example a 14-gauge needle or even a smaller needle, for example an 18-gauge needle. Chondrogenic factors and anti-hypertrophic factors released from the disclosed microbeads into the targeted area of diseased or damaged cartilage can stimulate nearby chondrocytes to proliferate and thus repair and regenerate the diseased or damaged cartilage tissue.

In another aspect, provided is a method of repairing cartilage in a subject diagnosed with diseased or damaged cartilage, comprising administering to a subject a therapeutically effective amount of a composition comprising injectable biodegradable polymeric hydrogel microbeads, wherein the microbeads comprise mesenchymal stem cells, for example adipose stem cells, in contact with a chondrogenic medium under suitable conditions, whereby contact with the chondrogenic medium inhibits the expression, production, or secretion of an angiogenic factor or a hypertrophic factor or both, or stimulates the expression, production, or secretion of a chondrogenic factor or an anti-hypertrophic factor or both, by the adipose stem cells.

In another aspect, provided is a method of controlling release of a biologically active composition from a biodegradable polymeric hydrogel microbead, comprising controlling the rate of degradation of the polymeric hydrogel, wherein the polymeric hydrogel is degraded by hydrolysis, by un-crosslinking of the polymeric hydrogel, or by a combination of both.

In one aspect, the diameter of a disclosed microbead is about 200 micrometers or less.

The biologically active composition can comprises a cell, a soluble protein, or an insoluble protein, or a combination thereof. In an aspect, a cell is a mesenchymal stem cell, for example, an adipose stem cell. Moreover, a wide variety of cells can be used in this aspect, depending on the type of cells that are desired to be released from a microbead. For example, for a microbead located in the body of a patient, it may be desirable to release one or more types of cell in the nearby tissue.

The biodegradable polymeric hydrogel can be an anionic polysaccharide, for example, an alginate.

In another aspect, the rate of hydrolysis is controlled by incorporating into the polymeric hydrogel a protease cleavage site, by incorporating into the polymeric hydrogel a site susceptible to hydrolysis, or by tethering a cleaving enzyme to the backbone of the polymeric hydrogel, or by a combination thereof.

In one aspect, a protease cleavage site is a peptide that is cleavable by a matrix metalloproteinase. A non-limiting example of such a peptide is a 12-amino acid oligopeptide identified as GGYGPVGLIGGK (SEQ ID NO:15).

A site susceptible to hydrolysis can be any appropriate site based on sequence, and in one aspect, a site susceptible to hydrolysis can comprise one or more acetal groups.

Any enzyme having the desired enzymatic activity of acting upon a polymeric hydrogel can be used. In one aspect, such an enzyme is alginate lyase.

In another aspect, a cleaving enzyme is released from a secondary nanoparticle or microparticle. For example, the secondary nanoparticle or microparticle can comprise polylactic-co-glycolic acid (PLGA), chitosan, agarose, gelatin, chondroitin sulfate, or a combination thereof. In one aspect, a secondary nanoparticle or microparticle is incorporated into the polymeric hydrogel.

In another aspect, an enzyme is incorporated into a polymeric hydrogel or secondary nanoparticle or microparticle at a temperature below its optimal active temperature and the operating physiological temperature of the hydrogel. Any suitable enzyme can be used. For example, alginate lyase can be incorporated into a polymeric hydrogel at 1° C. to 10° C.

In another aspect, the optimal active temperature and operating physiological temperature of the hydrogel is 37° C.

In another aspect, the optimal ratio range of alginate lyase to alginate is 0.5 units of lyase/g of alginate to 100 units of lyase/g alginate to control alginate degradation over a 12-day period.

In yet another aspect of the invention the rate of uncrosslinking of the polymeric hydrogel is controlled by adding to the polymeric hydrogel a chelator, by using a cross-linker with a lower ionic binding affinity, by using a degradable crosslinker, or by incorporating into the polymeric hydrogel a binding site for a molecule that can disrupt the structure of the polymeric hydrogel, or a combination thereof.

Any chelator capable of sequestering calcium can be used. In one aspect, the chelator is sodium citrate. In another aspect, the chelator is ethylenediaminetetraacetic acid (EDTA).

Any desired crosslinker that is capable of crosslinking a charged polymer with a lower ionic binding affinity can be used. Thus, in one aspect, a crosslinker with a lower ionic binding affinity is $CaSO_4$. In another aspect, a crosslinker with a lower ionic affinity is $CaCO_3$.

A variety of degradable crosslinkers can be used, for example a peptide that is cleavable by a matrix metalloproteinase. Examples of matrix metalloproteinases include, but are not limited to, collagenase, gelatinase, stromelysin, enamelysin, endometase, epilysin, and metalloslastase. An example of a binding site that can disrupt the structure of the polymeric hydrogel would be a peptide that mimics a natural amino acid domain that has the ability to change conformation by binding from an exogenous species. An example of an exogenous species may include, but is not be limited to, ions, molecules, and proteins.

In an aspect, a chelator is released from a secondary nanoparticle or microparticle. A secondary nanoparticle or microparticle can comprise polylactic-co-glycolic acid (PLGA), chitosan, agarose, gelatin, chondroitin sulfate, or a combination thereof. In an aspect, a secondary nanoparticle or microparticle is incorporated into a polymeric hydrogel.

In another aspect, a crosslinker is a polypeptide. A non-limiting example of such a peptide is the 12-amino acid oligopeptide sequence GGYGPVGLIGGK, identified as SEQ ID NO:15.

In yet another aspect, provided is a composition comprising injectable biodegradable polymeric hydrogel microbeads, wherein the microbeads comprise mesenchymal stem cells previously contacted with an osteogenic medium under suitable conditions, whereby contact with the osteogenic medium inhibited the expression, production, or secretion of an angiogenic factor. An osteogenic medium can be Dulbecco's Modified Eagle Medium, 15% fetal bovine serum (5-15%), 1% L-glutamine, 1 nM dexamethasone (1-100 nM), 6 mM beta-glycerophosphate (1-10 mM), and 50 µg/ml ascorbic acid (or ascorbic-2-phosphate), 50 ng/ml L-thyroxine (or No L-thyroxine).

In an aspect, the mesenchymal stem cells can be adipose stem cells.

Examples of angiogenic factors which can be inhibited include, but are not limited to, VEGF-A or FGF-2, or a combination of both.

In yet another aspect, provided is a composition comprising injectable biodegradable polymeric hydrogel microbeads, wherein the microbeads comprise mesenchymal stem cells previously contacted with an osteogenic medium under suitable conditions, whereby contact with the osteogenic medium increases the expression, production, or secretion of an osteogenic factor.

In an aspect, the mesenchymal stem cells can be adipose stem cells.

An osteogenic factor is a factor which induces osteogenesis, stimulates osteoblast proliferation, stimulates cellular synthesis of extracellular matrix components and other proteins found in bone, or directs mineralization of surrounding tissues. The osteogenic factors include, but are not limited to, bone morphogenetic protein-2 (BMP-2) and osteocalcin (OCN).

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLES

Example 1

Encapsulation of Cells

Ultrapure alginate compositions containing polysaccharides with .gtoreq.60% guluronate or mannuronate resides with average molecular weights > or <200,000 g/mole were used. Each alginate powder was sterilized using UV light and dissolved in 0.9% saline to produce a 2% (w/v) alginate solution. Rat chondrocytes suspended in a minimum volume of saline were added to the alginate solution resulting in $6 \times 10^6$ cells/ml. The solution was then extruded through a 0.18 mm (inner diameter) needle at 10 ml/hr. A 6,000 kV electrostatic potential between the $CaCl_2$ polymerization solution and the needle was used to disrupt the surface tension. Bead size and total cell number per bead were determined by morphometric analysis.

Cell number and bead size were controlled by varying the distance the cell suspension dropped before hitting the polymerization solution. Additional parameters were modulated according to the following generalized equations to obtain encapsulated cells having a diameter of less than 200 μm and containing a predetermined number of cells.

$$P_i - P_o = \frac{2y}{R}$$

$$P_i = \frac{F_s}{A}$$

$$A = 4\pi R^2$$

$$\frac{F_s}{4\pi R^2} - P_o = \frac{2\gamma}{R}$$

$$F_s = 4\pi R^2 \left(\frac{2\gamma}{R} + P_o\right)$$

$P_i$ = pressure inside droplet $P_o$ = pressure outside droplet (atmospheric pressure $y$ = surface tension of cell suspension $A$ = surface area of droplet $R$ = radius of droplet $F_s$ = surface force on droplet $F_e = -qE$ $E = \frac{V}{d}$ $F_e = -\frac{qV}{d}$ $F_e$ = electrostatic force $V$ = applied voltage $d$ = distance from needle to solution $q$ = charge on droplet $E$ = electric field $$Fe > Fs - \frac{qV}{d} > 4\pi R^2 \left(\frac{2\gamma}{R} + P_o\right)$$

$$(4\pi P_o)R^2 + (8\pi\gamma)R + \frac{qV}{d} < 0$$

$4\pi P_o$ = pressure term $8\pi y$ = surface tension term $\underline{qV}$ = electrostatic term Example 2

Effect of Alginate Composition on Microencapsulation

Alginate is co-polysaccharide composed of guluronate and mannuronate residues. The residue ratio and length of the polymer chains affect the mechanical properties of the alginate hydrogel. Four different alginate formulations (Table 2) were compared based on bead morphometrics and cell viability during two weeks of in vitro culture.

TABLE 1

Optimization of Microencapsulation Process

| Gelation Solution | Alginate Concentration | Bead Morphology | Cell Viability |
|---|---|---|---|
| 100 mM CaCl2 | 2.0% | Spherica | <50% |
| 50 mM CaCl2 + 75 mM NaCl | 2.0% | Irregular | ~50% |
| 20 mM CaCl2 + 120 mM NaCl | 2.0% | Irregular | ~70% |
| 50 mM CaCl2 + 150 mM Glucose | 2.0% | Spherical | ~90% |

TABLE 2

Alginate Compositions

| | Guluronate Content | |
|---|---|---|
| Molecular Weight | >60% | <40% |
| <200,000 g/mole | LVG | LVM |
| >200,000 g/mole | MVG | MVM |

Figure 1B:
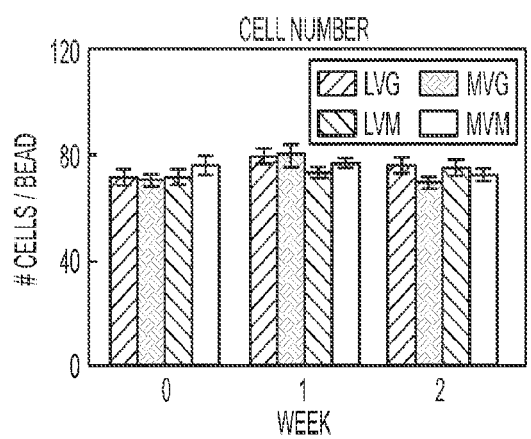
Figure 1C:
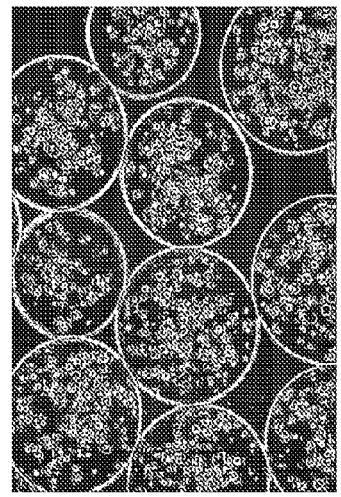
FIG. 1C shows a micrograph of representative beads and cells viewed by light microscopy.

The average bead diameter was 176.+−.2 μm to 194.+−.7 μm depending on the alginate composition used (FIG. 1A), but there was not statistically significant difference. In addition, no significant change in bead diameter was measured during the two weeks of in vitro culture. The initial cell number per bead was 69.+−.2 to 75.+−.3 (FIG. 1B), which corresponded to the loading density of $6\times10^6$ cells/ml. No significant change in cell number was observed over two weeks in any of the alginate compositions. The beads and encapsulated cells were easily viewed by light microscopy and remained intact and uniform during the two weeks of culture (FIG. 1C).

Example 3

Viability of Encapsulated Cells

Figure 2A:
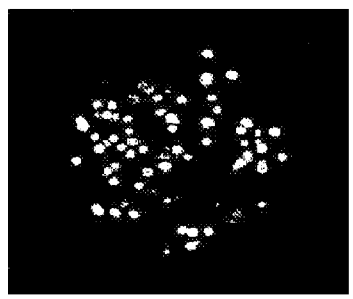
FIGS. 2A-C show fluorescent confocal micrograph of exemplary encapsulated cells using a calcein/ethidium homodimer-1 stain (A-C). The initial viability was 83% to 91%.
Figure 2B:
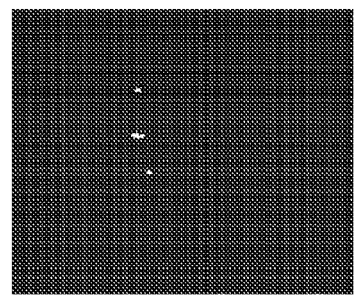
Figure 2C:
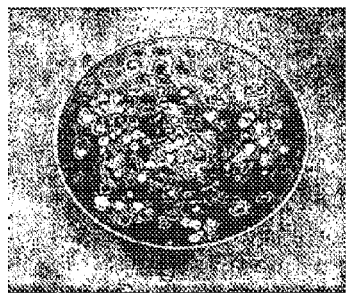
Figure 2D:
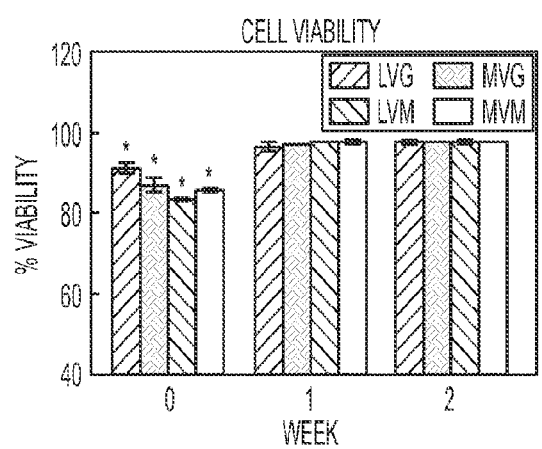
FIG. 2D shows a bar graph indicating viability increased after 1 week to >98% for all alginate compositions. *$P<0.05$, Initial vs. End Point.

The viability of the encapsulated chondrocytes was measured by fluorescent confocal microscopy and a live/dead stain consisting of calcein and ethidium homodimer-1. The calcein stains the cytoplasm of the live cells green (FIG. 2A) and the ethidium stains the nucleus of dead cells red (FIG. 2B). The live cells were evenly distributed throughout the beads (FIG. 2C) with an initial viability if 83% to 91% (FIG. 2D). The viability increased after one week in culture to greater than 98% for all alginate compositions and remained constant up to two weeks. No statistically significant differences were observed between the different alginate compositions on cell viability during the in vitro culture.

Example 4

In Vivo Implantation of Encapsulated Cells

The effects of alginate composition on encapsulated chondrocytes implanted in the gastrocnemius muscles of athymic mice for 4 weeks was investigated. The legs were harvested and stained with hematoxylin and eosin. Histological analysis did not show any obvious cartilaginous tissue, but the cells within the beads appeared to be alive at the time of harvest and had a round morphology characteristic of normal chondrocytes. In addition, the beads were surrounded by a dense cellularity with a basophilic matrix. It was unclear if the cellularity was infiltrating host tissue or donor cells migrating out of the implanted beads. The cellularity did not appear to be inflammatory and there was minimal fibrosis.

Example 5

Isolation of Cells

ASCs were isolated from the inguinal fat pad of 125 g Sprague Dawley rats (Harlan Laboratories, Indianapolis, Ind., USA) [14,15] or from human donors according to an approved IRB protocol. Briefly, rat fat pads were washed three times in Dulbecco's Modified Eagle Medium (DMEM, Invitrogen, Carlsbad, Calif., USA) with 3% penicillin and streptomycin (Invitrogen) and incubated in trypsin (Invitrogen) for 30 minutes. Fat pads were then diced and digested in 150 units/mL collagenase (Sigma, St. Louis, Mo., USA) and 3 units/mL dispase (Invitrogen) for four hours. ASCs were then pelleted and seeded at 5,000 cells/cm$^2$ in LonzaMesenchymal Stem Cell Growth Medium (MSCGM, Lonza Walkersville, Md., USA). After one passage, these cells were positive for CD73 and CD271 and negative for CD45 [15].

Costochondral chondrocytes from the ribs of 125 g male Sprague Dawley rats were isolated as described in detail previously [16,17]. Primary cells were cultured in DMEM containing 10% fetal bovine serum (FBS) and 50 µg/ml ascorbic acid (Invitrogen) until fourth passage prior to experimental analysis. These cells continue to express type II collagen, aggrecan, and cartilage oligomeric matrix protein [16].

Example 6

Microencapsulation

Figure 3A:
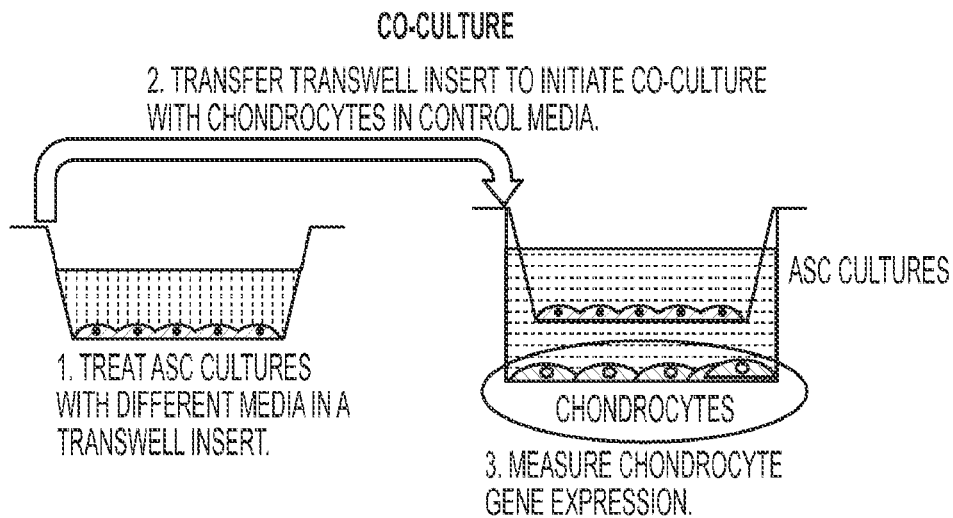
FIGS. 3A-D show effects of ASC Co-culture and ASC-conditioned media on chondrocyte gene expression. (A) Diagram of ASC co-culture and (B) conditioned media experiments. (C) Gene expression of chondrocytes after 7 days of ASC co-culture and (D) 24 hour treatment in ASC-conditioned media (n=6±SE. *$p<0.05$ vs. control, #$p<0.05$ vs. ASCs, <0.05 vs. ASC microbeads [ASC+μB]).

Once primary ASCs reached 90% confluence, cells were trypsinized and the first passaged ASCs were then microencapsulated. Low molecular weight (~150 kDa) alginate with a high mannuronate to guluronate ratio (40% guluronate) was UV light sterilized overnight and dissolved in 155 mM sodium chloride (Ricca Chemical, Arlington, Tex., USA) at a concentration of 20 mg/mL. ASCs were then seeded at 25×10$^6$ cells/mL, and microspheres were created using a Nisco Encapsulator VAR V1 LIN-0043 (Nisco Engineering AG, Zurich, Switzerland) at a 5 mL/hr flow rate, 0.175 mm nozzle inner diameter, and 6 kV/cm electrostatic potential [12,18]. Microbeads were cross-linked in a solution containing 50 mM CaCl$_2$, 150 mM glucose, and 15 mM 4-(2-hydroxyethyl)-1-piperazineethanesulfonic acid (pH=7.3, Sigma) for 15 minutes. The microbeads were washed 3 times in MSCGM prior to cell culture studies. First passaged ASCs were also plated in 6-well plates (FIG. 3A).

Example 7

ASC Cell Culture

Once first passaged ASCs reached 90% confluence, ASC monolayers and microbeads were then treated for 5 days with MSCGM, MSCGM with 10$^{-7}$ M 24R,25-dihydroxyvitamin D3, chondrogenic medium (CM) consistent of high glucose DMEM with 1 mM sodium pyruvate (Mediatech, Manassas, Va., USA), 40 µg/ml proline (Sigma), 50 µg/ml ascorbate-2-phosphate (Sigma), 1% ITS+, 100 nM dexamethasone (Sigma), 10 ng/ml recombinant human transforming growth factor beta-I (TGF-β1, R&D Systems, Minneapolis, Minn., USA) and 100 ng/ml recombinant human bone morphogenic protein 6 (BMP-6, PeproTech, Rocky Hill, N.J., USA) or medium consistent of high glucose DMEM with 1 mM sodium pyruvate (Mediatech, Manassas, Va., USA), 40 µg/ml proline (Sigma), 50 µg/ml ascorbate-2-phosphate (Sigma), 1% ITS+, and 10$^{-7}$M 24R,25-dihydroxyvitamin D3. Once media were changed on the fifth day, RNA was collected after 8 hours as described below while media and ASCs lysed in 0.05% Triton X-100 were collected after 24 hours. Monolayer fourth passaged chondrocytes cultured in DMEM, 10% FBS, and 50 µg/mL ascorbic acid and Sprague Dawley-derived clone 9 liver cells (ATCC, Manassas, Va., USA) cultured in F12K medium and 10% FBS served as controls. All media contained 1% penicillin and streptomycin.

Example 8

Growth Factor Expression and Production

Microbeads were uncross-linked in 82.5 mM sodium citrate (Sigma), pelleted at 500 g for 10 minutes and washed 2 more times in sodium citrate to remove any residual alginate. TRIzol reagent (Invitrogen) was added to the resulting cell pellet, homogenized using a QIAshredder (QIAGEN, Valencia, Calif., USA), and RNA was isolated using chloroform and an RNeasy Kit (Qiagen) as previously described [19]. 1 µg RNA was then reverse transcribed to cDNA using a High Capacity Reverse Transcription cDNA kit (Applied Biosystems, Carlsbad, Calif., USA). Expression of growth factors and chondrogenic genes was quantified as previously described using real-time PCR with gene-specific primers using the Step One Plus Real-time PCR System and Power Sybr® Green Master Mix (Applied Biosystems) [20]. Primers were designed using Beacon Designer software (Premier Biosoft, Palo Alto, Calif., USA) and synthesized by Eurofins MWG Operon (Huntsville, Ala., USA) unless otherwise noted (Table 4). VEGF-A and FGF-2 production over the last 24 hours of culture was quantified using ELISA (R&D Systems) and normalized to DNA content measured with a Quant-iTPicoGreen kit (Invitrogen).

Example 9

ASC-Chondrocyte Co-Culture

Figure 4A:
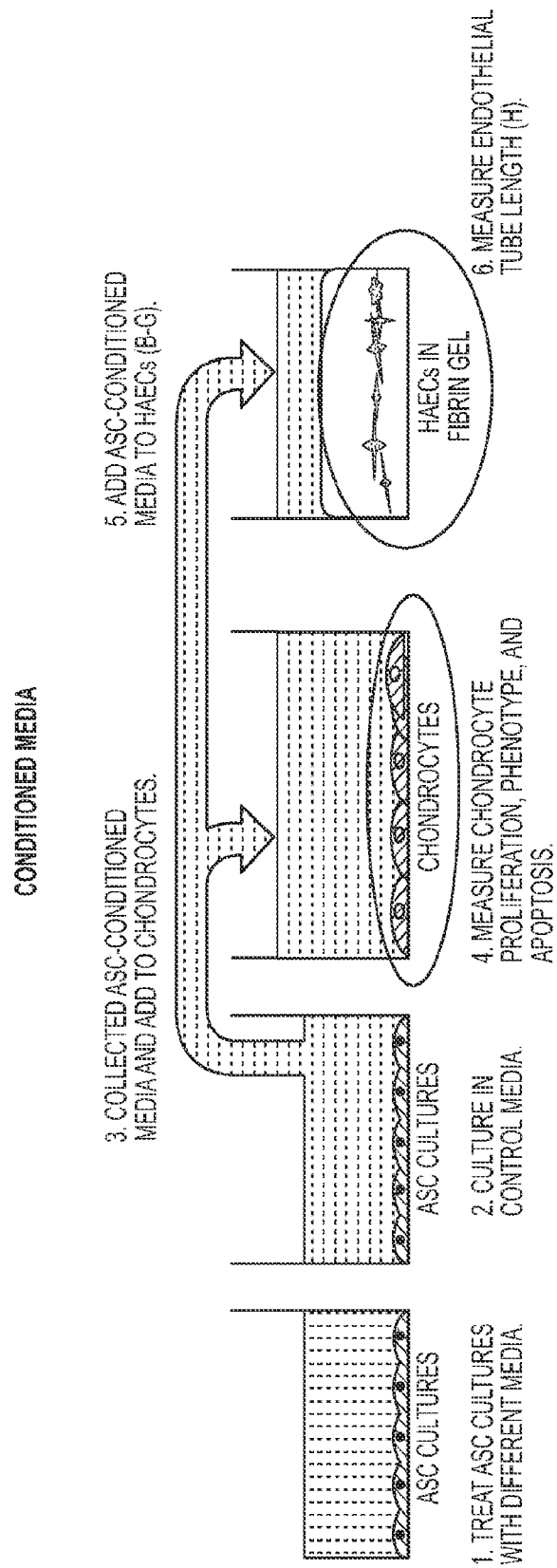
FIGS. 4A-H show effects of ASC-conditioned media on chondrocyte phenotype, proliferation, apoptosis, and angiogenic response. (A) Diagram of ASC-conditioned media experiments, (B) [$^{35}$S]-sulfate incorporation, (C) alkaline phosphatase activity, (D) [$^{3}$H]-thymidine incorporation, (E) caspase-3 activity, (F) bax/bcl2 expression, (G) DNA fragmentation, and (H) endothelial length (n=6±SE. *$p<0.05$ vs. control, #$p<0.05$ vs. ASCs, ^$p<0.05$ vs. ASC microbeads (ASC+μB)).

To assess the effects paracrine signaling between ASCs and chondrocytes had on chondrocyte phenotype, the two cell types were co-cultured in a trans-well system (FIG. 4A). Initial studies determined the number of microbeads per insert needed to have the same cell number as ASC confluent trans-well inserts. ASC monolayers and microbeads were treated with MSCGM or with chondrogenic media for 5 days in 0.2 µm high density cell culture inserts (BD Biosciences, Franklin Lakes, N.J., USA). ASC cultures and inserts were then washed in DMEM three times and added to wells with confluent chondrocytes. The two cell groups were then cultured in 4.5 mL DMEM+10% FBS. After 7 days, RNA was isolated from the chondrocytes to quantify chondrogenic gene expression. Microencapsulated clone 9 liver cells served as a control.

Example 10

ASC-Conditioned Media Chondrocyte Cultures

To assess the effects ASC-secreted growth factors have on chondrocytes, chondrocytes were cultured in ASC-conditioned media (FIG. 4B) obtained from T-75 flasks. Initial studies determined the number of microbeads per T-75 needed to have the same cell number as ASC confluent T-75 flasks. To obtain ASC-conditioned media, ASC monolayers and microbeads were treated with MSCGM or with chondrogenic media for 5 days in T-75s. After the fifth day of treatment, ASC monolayers and microbeads were washed in DMEM 3 times and 10 mL DMEM+10% FBS was added to each culture. After 24 hours, media containing the ASC-secreted factors were collected then immediately added to confluent chondrocyte cultures. After 12 hours in ASC-conditioned media, RNA was isolated from chondrocytes to quantify chondrogenic gene expression. To assess chondrocyte phenotype, apoptosis, and angiogenic response, the following assays were performed after 24 hours of ASC-conditioned media treatments. Conditioned medium from microencapsulated clone 9 liver cells served as a control.

Example 11

[$^3$H]-Thymidine Incorporation

DNA synthesis was assayed by measuring [$^3$H]-thymidine incorporation as described previously [21]. 40% confluent chondrocytes were treated with DMEM+1% FBS to induce quiescence. ASC-conditioned media were then added for 24 hours. Four hours before harvest, [$^3$H]-thymidine was added to a final concentration of 0.25 µCi/mL. Radioactivity in trichloroacetic acid-insoluble cell precipitates was measured by liquid scintillation spectroscopy.

Example 12

[$^{35}$S]-Sulfate Incorporation

Proteoglycan synthesis was assayed by measuring [$^3$S]-sulfate incorporation as previously described [22]. Since the amount of radiolabeled proteoglycan secreted by chondrocytes into the medium was previously found to be less than 15% of total radiolabeled proteoglycan production [23], only [$^{35}$S]sulfate incorporation of the monolayer was measured. 20 hours after ASC-conditioned media were added, [$^{35}$S]-sulfate was added to a final concentration of 18 µCi/mL for the final 4 hours of culture. Cells were then scraped in 0.25 M NaOH, diluted with an equal volume of 0.15 M NaCl, and added to 12-14 kDa dialysis tubing (Spectrum Labs, Rancho Dominguez, Calif., USA). Dialysis solution was replaced every 24 hours until the radioactivity was similar to baseline. The entire sample was then measured by liquid scintillation spectroscopy and normalized to protein content measured with a Pierce Macro BCA protein kit (ThermoScientific, Rockford, Ill., USA).

Example 13

Alkaline Phosphatase Activity

Alkaline phosphatase activity was measured as a function of release of p-nitrophenol from p-nitrophenylphosphate as previously described [24]. Enzyme activity was assayed after 1 hour at 37° C. and normalized to protein content measured with a Pierce Macro BCA protein kit (Thermo-Scientific).

Example 14

DNA Fragmentation

Confluent chondrocytes were pulsed with [$^3$H]-thymidine for 4 hours prior to ASC-conditioned media treatment for 24 hours [17]. Confluent chondrocyte cell monolayers were washed with DMEM three times to remove unincorporated [$^3$H] and cells were lysed with TE buffer (10 mMTris-HCl, 1 mM EDTA, 0.2% Triton X-100) for 30 min. Cell lysates were centrifuged at 13,000×g for 15 min to separate intact DNA from fragmented DNA. The amount of incorporated [$^3$H]-thymidine was determined in each fraction to establish the total amount of fragmented DNA.

Example 15

Caspase-3 Activity

Caspase-3 activity was determined using a colorimetric CaspACE™ Assay System from Promega (Madison, Wis., USA). 24 hours after ASC conditioned media were added to confluent chondrocytes, cells were scraped with PBS and suspended in 200 µl of cell lysis buffer. Samples were frozen at −80° C., thawed and sonicated twice. 2 µl of the caspase-3 selective substrate DEVD-pNA was added to each well containing 100 µl of cell lysate and incubated at 37° C. for 4 h. DEVD-pNA cleavage into the colorimetric product pNA was measured at 405 nm. Caspase-3 activity was normalized to total protein content measured with aPierce 660 nm protein assay (ThermoScientific).

Example 16

Fibrin Gel Assay

Angiogenic responses to ASC-conditioned media were assessed with endothelial cells cultured in a fibrin gel assay as previously described [25]. 30 µL of fibrinogen solution and 20 µL of thrombin solution were added to each well of a 96-well plate and the mixture was allowed to polymerize for 30 min at 37° C. Human aortic endothelial cells (HAECs, Lonza) were plated in 100 µL of endothelial cell basal medium (EGM-2, Lonza) at a density of 5×103 cells/well and cultured at 37° C. for 24 hours. At 24 hours, medium was removed and a second layer of fibrin was added on top of cells. The mixture was allowed to polymerize for 5 min before 100 µL of ASC conditioned media were added. After 12 hours, images were taken for morphometric analysis and total endothelial tube length was determined using Image Pro Plus.

Example 17 rhVEGF-A, rhFGF-2, and Antibodies Treatments

To determine the effect exogenous vascular endothelial growth factor A (VEGF-A) and fibroblastic growth factor 2 (FGF-2) have on chondrocytes, 1 ng/mL and 20 ng/mL of recombinant human VEGF-A165 and recombinant human FGF-2 (R&D Systems) were added to monolayer cultures of fourth passaged chondrocytes. To determine the effect VEGF-A and FGF-2 secreted by ASCs have on chondrocytes, conditioned medium from MSCGM-treated ASC monolayers was supplemented with 1 µg/mL goat anti rat IgG, 1 µg/mL anti-rat VEGF-A neutralizing antibody, or 1 µg/mL anti-rat FGF-2 neutralizing antibody and added to fourth passaged chondrocyte monolayers. After 24 hours, caspase-3 activity and [$^3$H]-thymidine incorporation were measured as described above. DMEM+10% FBS and conditioned medium from ASC monolayers treated with chondrogenic medium served as controls.

Example 18

Xiphoid Defect In Vivo

To assess if ASCs would inhibit cartilage regeneration, non-critically sized defects were made in the xiphoids of 125 g Sprague-Dawley rats as previously described [26, 27]. Once the peritoneum was accessed and the xiphoid was dissected free from the anterior abdominal wall, a full-thickness 1 mm cylindrical defect was made in the center of the xiphoid using a dermal biopsy punch (Mitex, Plainsboro, N.J., USA). This defect size was chosen because cartilage regeneration was previously observed after 35 days and the defect is large enough to contain cell pellets $1\times10^6$ ASCs in size [26]. A 1 cm×1 cm strip of SepraFilm® (Genzyme, Cambridge, Mass., USA) was then placed on the dorsal side of the xiphoid to protect the defect and serve as an adhesion barrier. ASC monolayers cultured in MSCGM or chondrogenic medium were pelleted at $1\times10^6$ ASCs/pellet and implanted into the defect. Empty defects and autografts (excised cartilage is re-implanted) served as controls. After groups were implanted, another strip of SepraFilm® was used to cover the ventral side of the xiphoid and the peritoneum and abdominal musculature were closed. Xiphoids were then excised 35-days post-surgery and examined as described below.

Example 19

Radiographic Imaging

Radiographic imaging (FaxitronBioptics, Lincolnshire, Ill., USA) was performed in the coronal plane at a voltage of 22 mV and exposure time of 16s to visualize soft tissue penetration as previous described [26]. A blind observer then scored the presence of soft tissue penetration with a score of 0 representing no healing, a score of 0.5 representing partial healing, and a score of 1 representing full healing.

Example 20

Equilibrium Partitioning of an Ionic Contrast Agent Micro-Computed Tomography (EPIC-μCT)

EPIC-μCT was used to visualize the distribution of proteoglycans within the xiphoid defects as previously described [26,28]. Xiphoids were washed in phosphate buffered saline (PBS), then incubated in 2 mL of 40% Hexabrix contrast agent (Mallinckrodt, St. Louis, Mo., USA) solution in PBS containing 1% proteinase inhibitor cocktail (CalBiochem, Darmstadt, Germany) overnight. Xiphoids were then patted dry and scanned in a μCT 40 (Scanco Medical, Brüttisellen, Switzerland) at 45 kV, 177 μA, 200 ms integration time, and 16 μm voxel size. Three-dimensional color images based on the X-ray attenuation were created by the Scanco software to observe proteoglycans in the tissue. Consistent with the inverse partitioning between proteoglycan concentration and contrast agent, low X-ray attenuation corresponded to regions of high proteoglycan concentration and no or high X-ray attenuation indicated regions of low proteoglycan concentration. To determine cartilage volume, the 1 mm defect was isolated with user-guided contours and evaluated at a 100-250 threshold range.

Example 21

Histology

After samples were analyzed with EPIC-μCT, they were washed in PBS for two hours, fixed in 10% phosphate-buffered formalin for 48 hours, and then embedded in paraffin. Seven-micrometer thick serial sections were obtained via a rotary microtome (HM 355 s rotary microtome; Microm, Walldorf, Germany) and stained with hematoxylin and eosin stain (H&E) to highlight cells and extracellular matrix on microscope images (DMLB; Leica, Nussloch, Germany).

Statistical Analysis

All in vitro experiments had six independent cultures per treatment group to ensure sufficient power to detect statistically significant differences. All in vitro experiments were conducted multiple times to validate the observations, but only data from a single representative experiment are shown and are expressed as means±standard errors. A power analysis determined that seven samples per group were needed for the in vivo study. Statistical analysis was conducted using ANOVA analysis with a post hoc Tukey test (GraphPad Prism, La Jolla, Calif., USA). Differences in means were considered to be statistically significant if the p-value was less than 0.05.

Results

Angiogenic Growth Factor Production from ASCs

Figure 3B:
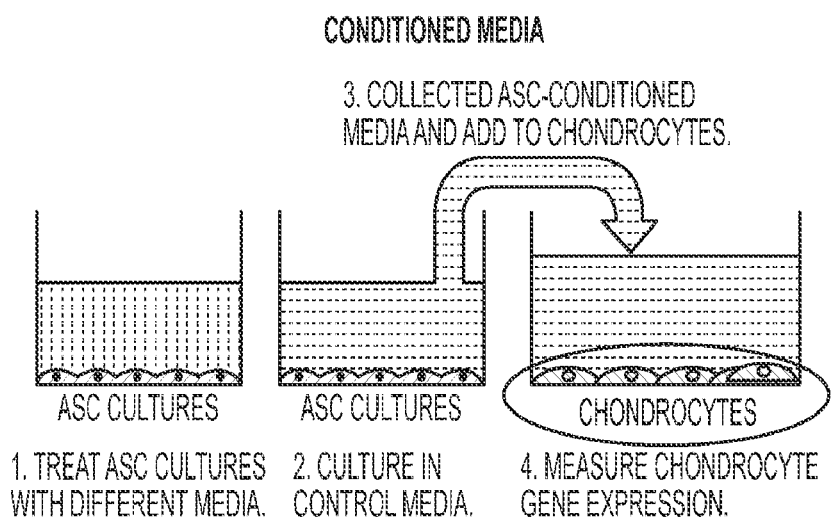
Figure 3C:
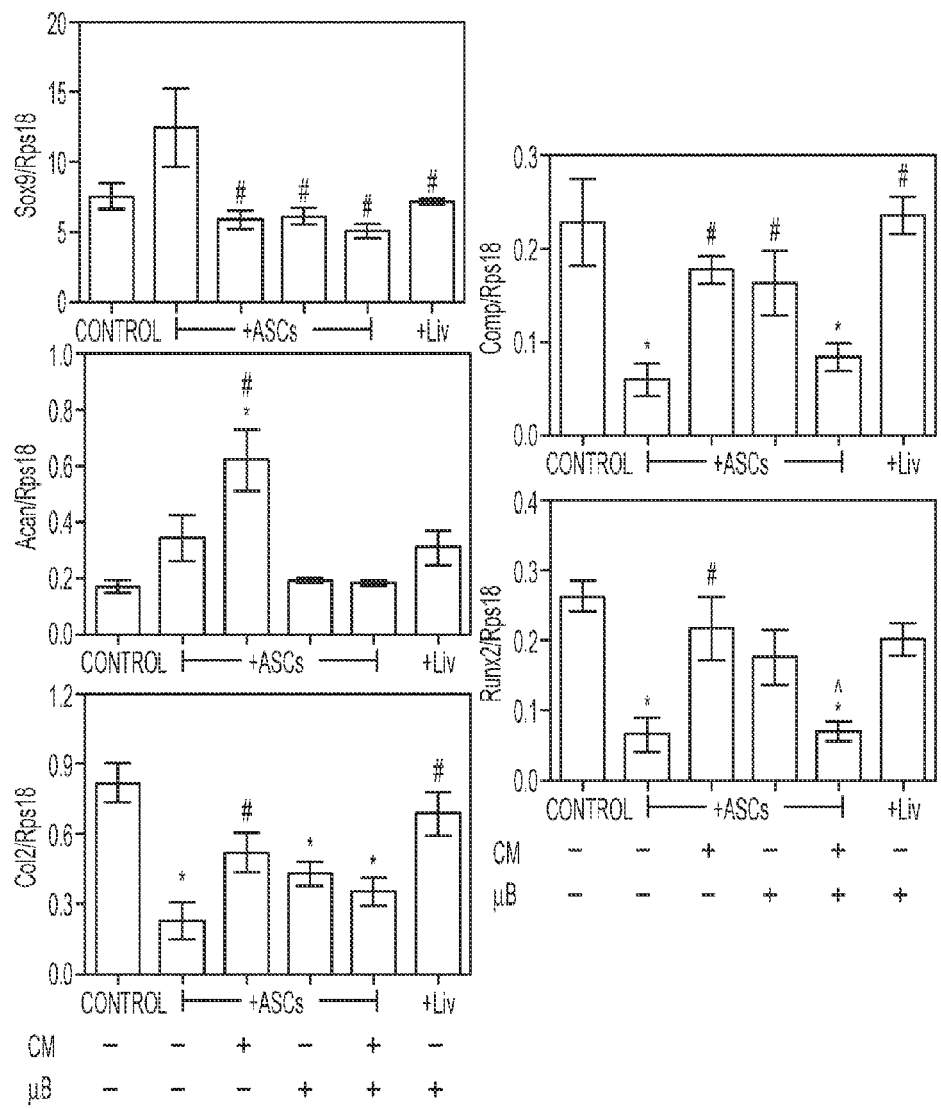
Figure 3D:
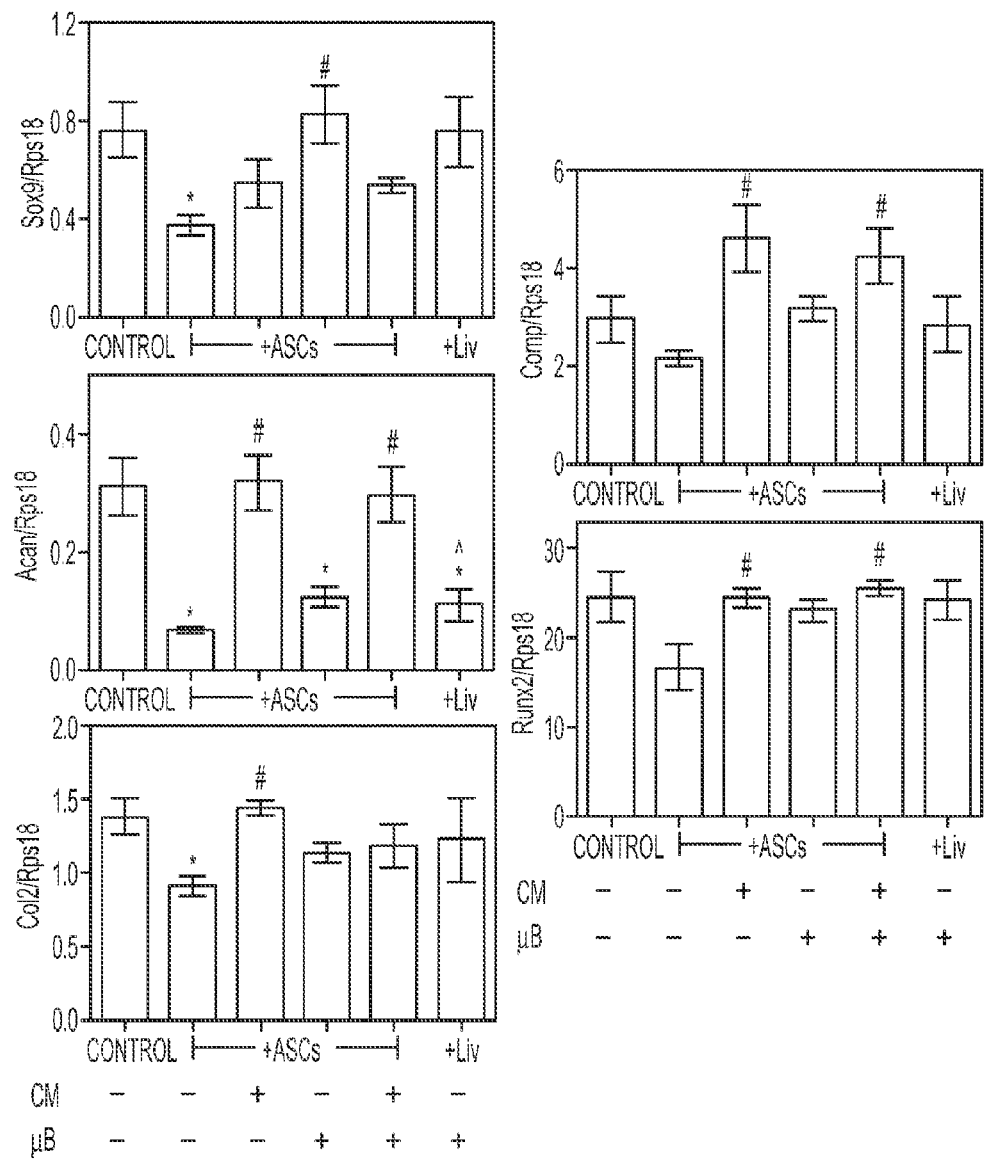

ASC monolayers and microbeads cultured in MSCGM had 3 times higher expression of VEGF-A but only half the expression of Pdgfa compared to chondrocytes (FIG. 3B). Chondrogenic medium treatment significantly reduced ASC expression levels of both VEGF-A and Fgf2 compared to ASCs cultured in MSCGM, resulting in expression levels similar to that of chondrocytes. However, chondrogenic medium did not influence Pdgfa expression. ASC monolayers secreted 10 times more VEGF-A than chondrocytes while ASC microbeads secreted 30 times more VEGF-A than chondrocytes (FIG. 3C). Chondrogenic medium treatments reduced VEGF-A secretion from ASC monolayers by 3 folds and from ASC microbeads by 3.5 folds, but VEGF-A secretion from both groups were still significantly greater than that from chondrocytes. FGF-2 secretion from ASC cultures and chondrocytes was very low compared to VEGF-A production though microencapsulation significantly increased FGF-2 secretion.

Effect of ASC Paracrine Signaling and Secreted Factors on Chondrocyte Gene Expression To determine the effect ASC paracrine signaling had on chondrocytes, a co-culture study was conducted (FIG. 4A). When ASC monolayers cultured in MSCGM were co-cultured with chondrocytes for 7 days, chondrocytes experienced 3.5 to 4 folds reductions in col2, comp, and runx2 expression compared to chondrocytes with no co-culture (FIG. 4C). However, ASC monolayers previously treated with chondrogenic medium increased acan expression in chondrocytes and had no effect on col2, comp, and runx2 expression in chondrocytes compared to control. ASC microbeads cultured in MSCGM significantly reduced col2 expression in chondrocytes, but ASC microbeads treated with chondrogenic medium significantly reduced col2, comp, and runx2 expression in chondrocytes compared to control. ASC co-cultures did not affect sox-9 expression, and co-culture with clone 9 liver cell microbeads did not influence chondrocyte gene expression compared to control.

Figure 4B:
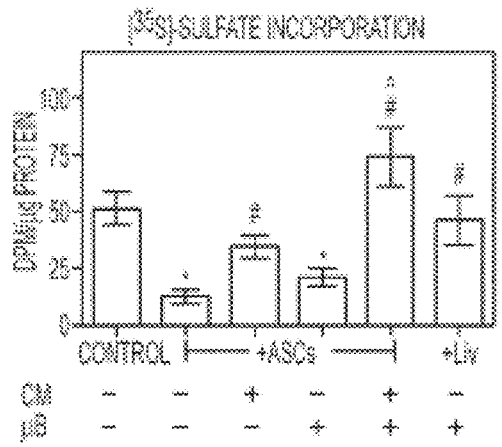
Figure 4C:
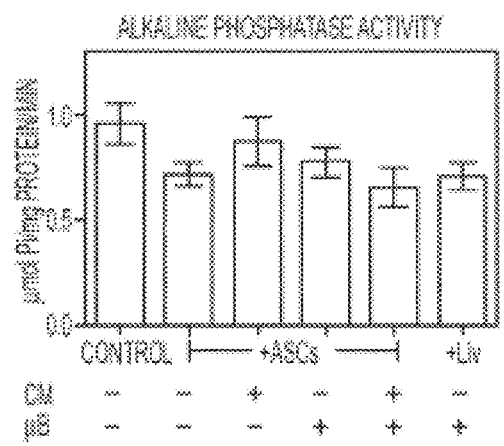
Figure 4D:
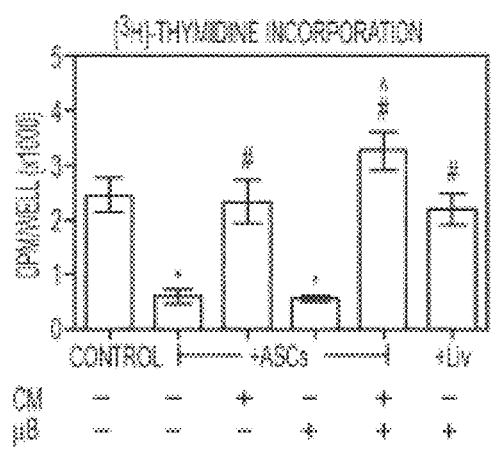
Figure 4E:
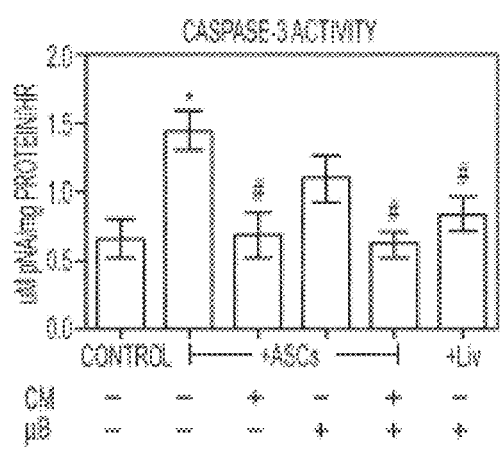
Figure 4F:
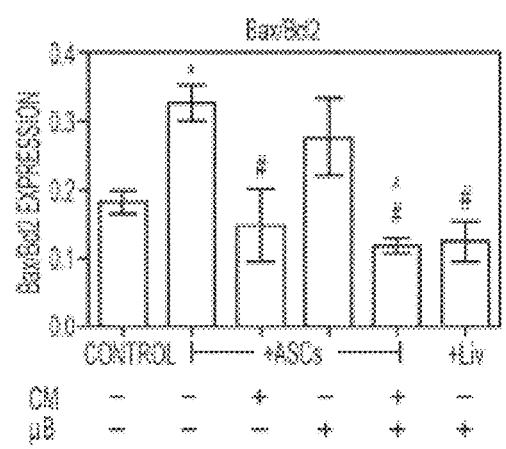
Figure 4G:
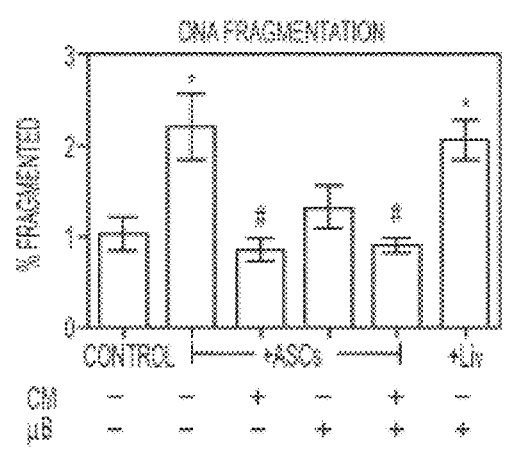
Figure 4H:
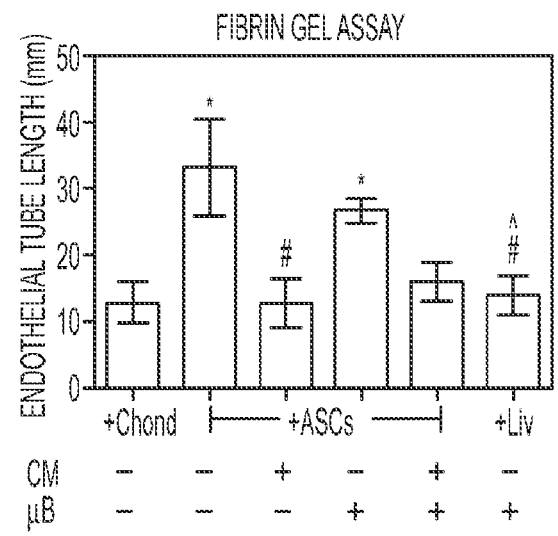
Figure 4H:
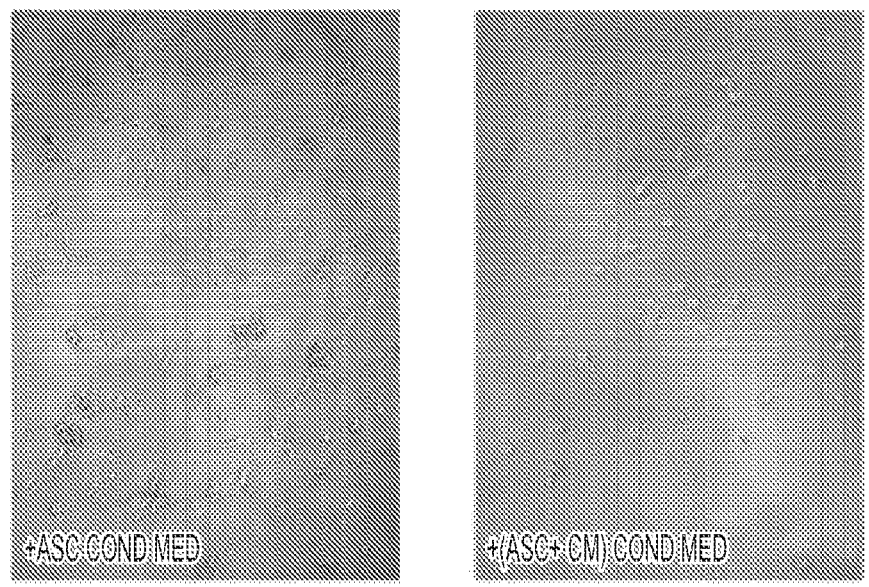

To determine the role ASC-secreted factors had on chondrocyte gene expression, a conditioned media study was performed (FIG. 4B). When conditioned medium from ASC monolayers cultured in MSCGM was added to chondrocyte for 12 hours, sox9 expression decreased by 50%, acan decreased by 78%, and col2 decrease by 35% compared to chondrocytes treated with control medium (FIG. 4D). However, conditioned medium from ASC monolayers previously treated with chondrogenic medium had no effect on chondrogenic gene expression compared to control medium. Conditioned medium from ASC microbeads cultured in MSCGM decreased acan expression, but conditioned medium from ASC microbeads treated with chondrogenic medium had no effect on chondrocyte gene expression. Additionally, treating chondrocytes with conditioned medium from ASC monolayers treated with chondrogenic medium increased acan, col2, comp, and runx2 expression compared to chondrocytes treated with conditioned medium ASC monolayer cultured in MSCGM. Clone 9 liver cell microbeads decreased aggrecan expression in chondrocytes but had no effect on sox9, col2, comp, or runx2.

Effect of ASC-Secreted Factors on Proliferation, Phenotype, and Apoptosis

Figure 5A:
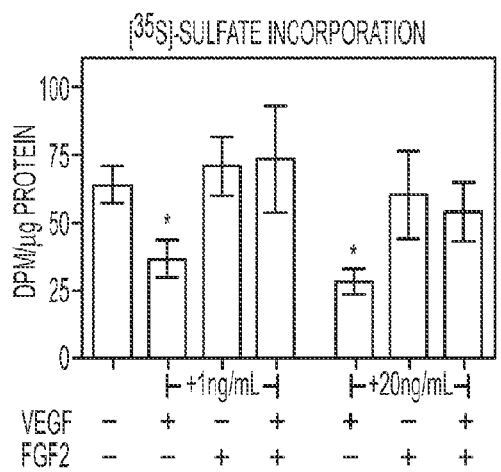
FIGS. 5A-C show Effects of exogenous VEGF-A and FGF-2 on chondrocytes. (A) [$^{35}$S]-sulfate incorporation of chondrocytes treated with recombinant human VEGF-A and FGF-2, (B) caspase-3 activity of chondrocytes treated with recombinant human VEGF-A and FGF-2, and (C) [$^{3}$H]-thymidine incorporation of chondrocytes treated with recombinant human VEGF-A and FGF-2 (n=6±SE. *$p<0.05$ vs. control, #$p<0.05$ vs. ASCs).
Figure 5B:
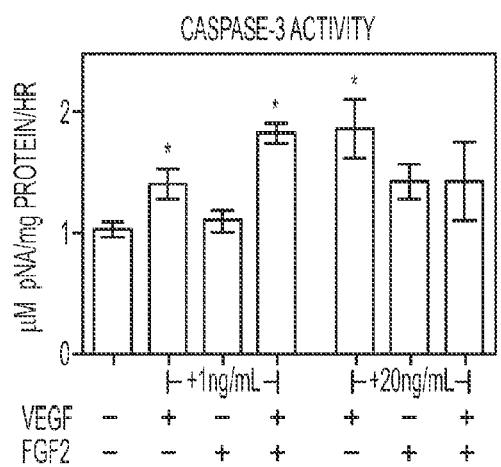
Figure 5C:
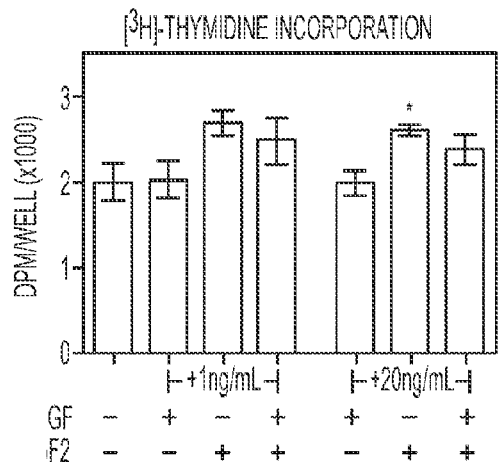

Additional conditioned media studies were carried out to further elucidate the role ASC-secreted factors have on chondrocyte phenotype and proliferation (FIG. 5A). After 24 hours, conditioned media from ASC monolayer and microbeads cultured in MSCGM decreased [$^{35}$S]-sulfate incorporation by 75% and 60% respectively compared to control (FIG. 5B) but had no effect on alkaline phosphatase activity (FIG. 5C). Conditioned media from ASC monolayer and microbeads cultured in MSCGM also decreased [$^{3}$H]-thymidine incorporation by approximately 76% compared to chondrocytes treated with control medium (FIG. 5D). Treating ASC monolayers and microbeads with chondrogenic medium prior to conditioned media collection eliminated the deleterious effects ASC-secreted factors had on chondrocytes (FIGS. 5B, D). Liver microbead conditioned medium did not affect [$^{3}$H]-thymidine incorporation, [$^{35}$S]-sulfate incorporation, or alkaline phosphatase activity (FIGS. 5B-D).

To determine if ASC-secreted factors were inducing chondrocyte apoptosis, different apoptotic markers were assayed after ASC-conditioned media treatments. Conditioned medium from ASC monolayer cultured in MSCGM increased caspase-3 activity 120%, bax/bcl expression 79%, and DNA fragmentation 114% compared to control medium (FIGS. 5E-G). Treating ASC monolayers with chondrogenic medium prior to collecting conditioned medium eliminated the apoptotic effects ASC-secreted factors had on chondrocytes. Conditioned medium from ASC microbeads cultured in MSCGM did not increase apoptosis compared to control medium. Conditioned medium from liver microbeads had no effect on caspase-3 activity, bax/bcl, but did increase DNA fragmentation compared to control (FIGS. 5E-G).

To determine if the detrimental effects of ASC-secreted factors were specific to chondrocytes, chondrocyte, ASC, and liver conditioned media were applied to human aortic endothelial cells (HAECs) to determine if there was an angiogenic response. ASC monolayer and microbead conditioned media increased endothelial tube length by 2.6 folds and 2 folds respectively (FIG. 5G). Treating ASCs with chondrogenic media prior to conditioned media collection eliminated this angiogenic response. Conditioned media from liver microbeads had no effect on endothelial tube length.

Effect of Exogenous VEGF-A and FGF-2 on Chondrocytes

Figure 6B:
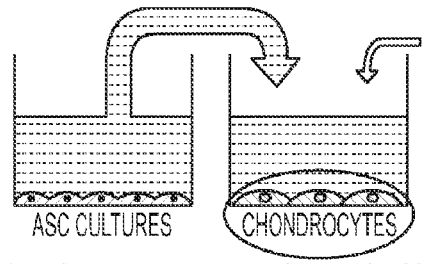
Figure 6B:
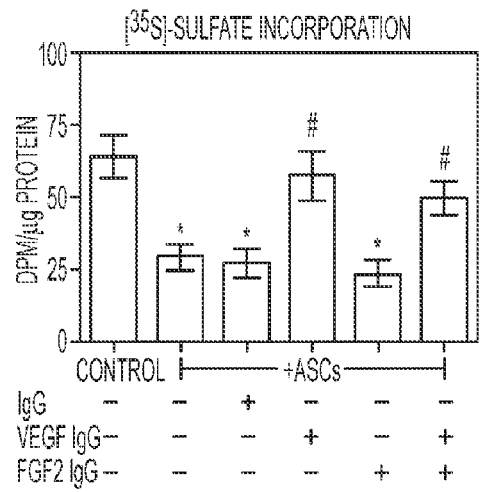
Figure 6C:
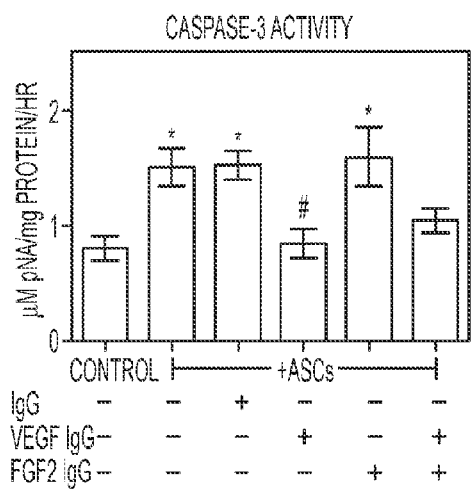
Figure 6D:
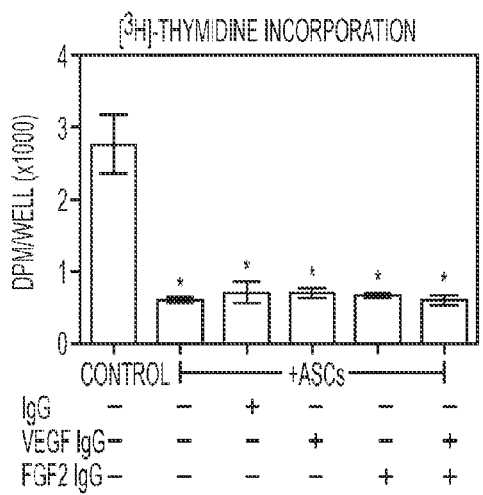

To determine the effect angiogenic factors VEGF-A and FGF-2 have on chondrocyte proteoglycan production (phenotype), caspase-3 activity (apoptosis), and [$^{3}$H]-thymidine incorporation (proliferation), 1 ng/mL and 20 ng/mL of each growth factor were added to chondrocytes. Both 1 ng/mL and 20 ng/mL of recombinant human VEGF-A (rhVEGF-A) treatments reduced [$^{35}$S]-sulfate incorporation by approximately 30% and 50% respectively (FIG. 6A). Adding rhFGF-2 at both 1 and 20 ng/mL alone had no effect on [$^{35}$S]-sulfate incorporation but did eliminated the inhibitory effect rhVEGF-A had on [$^{35}$S]-sulfate incorporation at both concentrations. Meanwhile both 1 ng/mL and 20 ng/mL rhVEGF-A significantly increased caspase-3 activity by 32% and 84% respectively (FIG. 6B). Adding 1 ng/mL of rhFGF-2 had no effect on caspase-3 activity and did not reduce the apoptotic effect of rhVEGF-A compared to control. However, 20 ng/mL rhFGF-2 eliminated the apoptotic effect of VEGF-A. VEGF-A and FGF-2 had a more limited effect on chondrocyte proliferation, as only the 20 ng/mL rhFGF-2 dosage increased [$^{3}$H]-thymidine incorporation (FIG. 6C).

Role of ASC-Secreted VEGF-A and FGF-2 on Chondrocytes

Figure 7A:
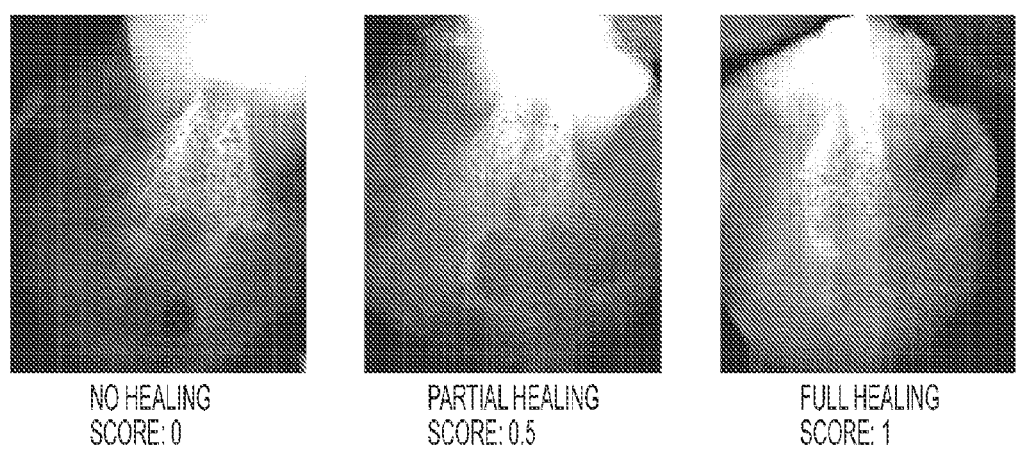
FIGS. 7A-C show effects of ASCs on cartilage regeneration. (A) Radiographic scoring. (B) 3-DEPIC-μCT images of xiphoids and calculated cartilage volume within defects (n=7±SE. *$p<0.05$ vs. empty defect, #$p<0.05$ vs. ASCs). (C) Representative H&E staining. Bar represents 100 μm at 20× magnification (D=defect, X=xiphoid, AG=autograft).
Figure 7B:
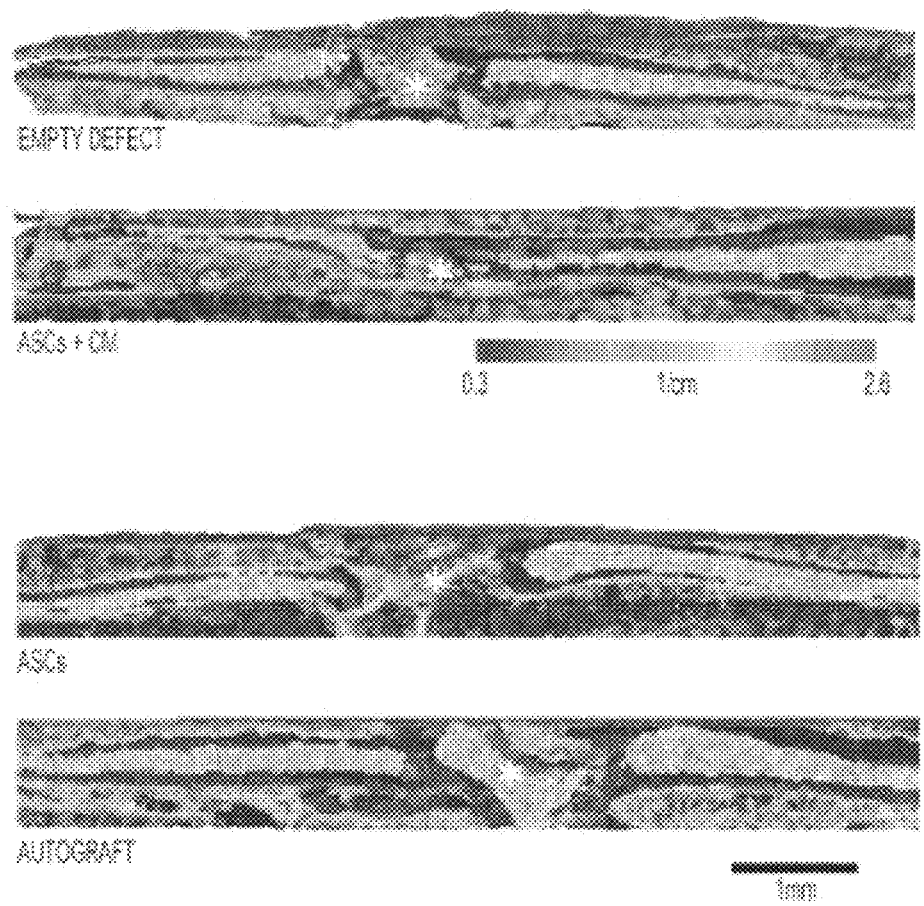
Figure 7B:
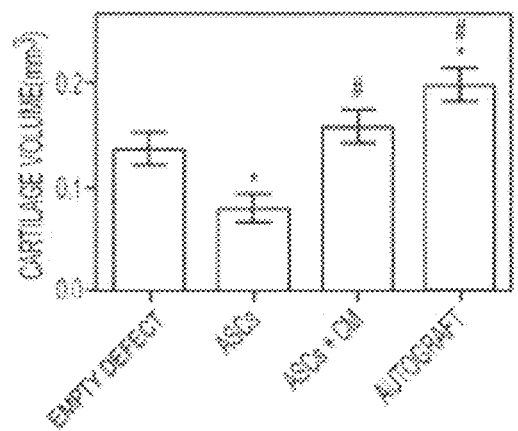
Figure 7C:
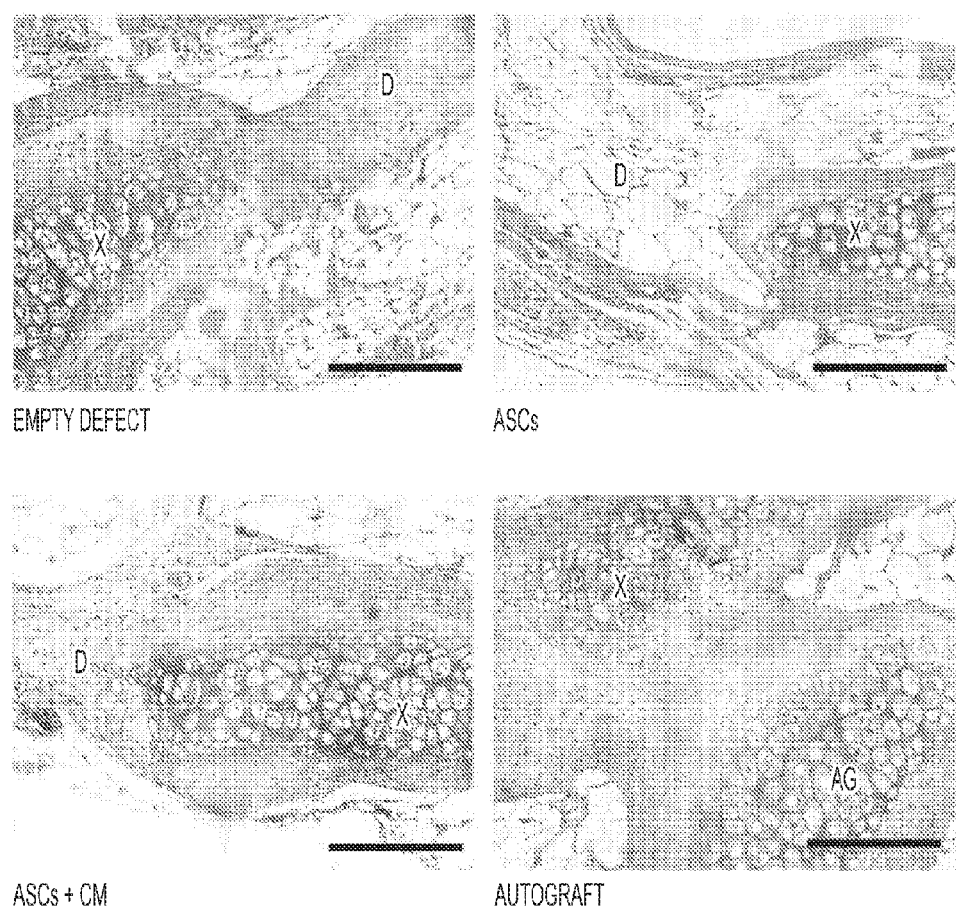

To determine if VEGF-A and FGF-2 in ASC monolayer conditioned medium were responsible for decreased chondrocyte proteoglycan production (phenotype), increased chondrocyte caspase-3 activity (apoptosis), and decreased [$^{3}$H]-thymidine incorporation (proliferation), conditioned medium from ASC monolayers cultured in MSCGM was supplemented with neutralizing antibodies for VEGF-A and FGF-2 were added to chondrocytes (FIG. 7A). ASC-conditioned medium with a goat-anti-rat IgG and FGF-2 neutralizing antibody decreased [$^{35}$S]-sulfate incorporation by approximately 50% (FIG. 7B) and increased caspase-3 activity by approximately 94% (FIG. 7C) compared to control medium. Adding VEGF-A neutralizing antibody to ASC conditioned medium eliminated both its deleterious effect on chondrocyte phenotype and apoptotic effect. ASC conditioned media with or without VEGF-A or FGF-2 neutralizing antibodies all decreased [$^{3}$H]-thymidine incorporation compared to control medium (FIG. 7D). As previously observed, conditioned medium from ASC monolayers treated with chondrogenic medium had no effect on chondrocyte caspase-3 activity, [$^{35}$S]-sulfate, and [$^{3}$H]-thymidine incorporation compared to control medium.

Role of ASCs in Cartilage Defect

Figure 8A:
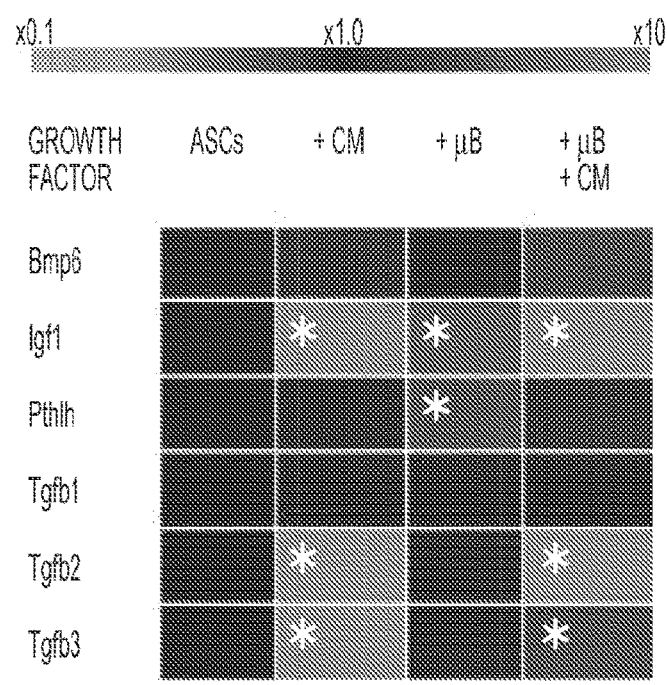
FIG. 8 shows the effect of microencapsulation and chondrogenic medium (CM) on chondrogenic factor production on monolayer and microencapsulated (μB) rat ASCs. MGM=Lonza Mesenchymal Stem Cell Growth Media, Chond=chondrocytes, ASCs=adipose stem cells (n=4 experiments).
Figure 8B:
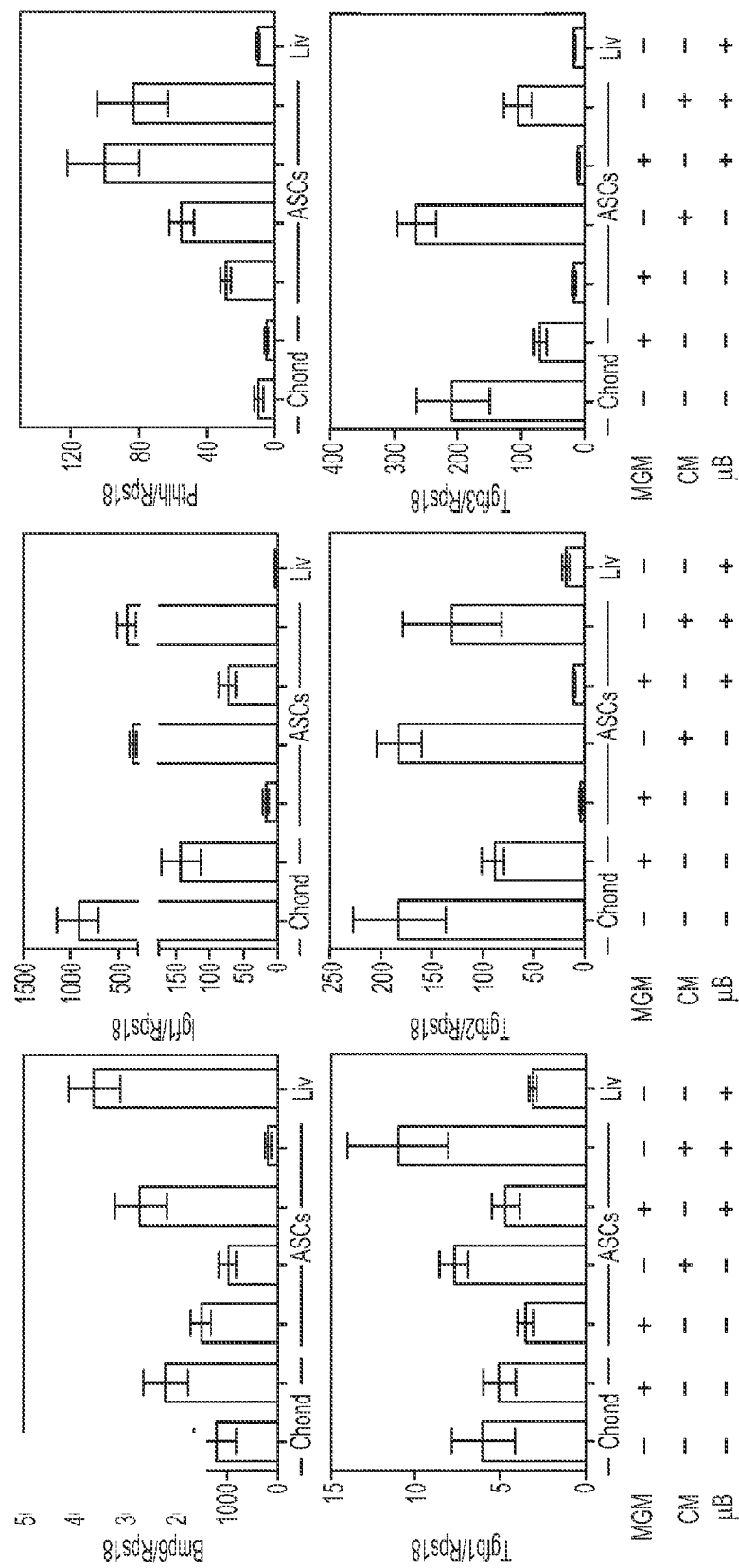
Figure 8C:
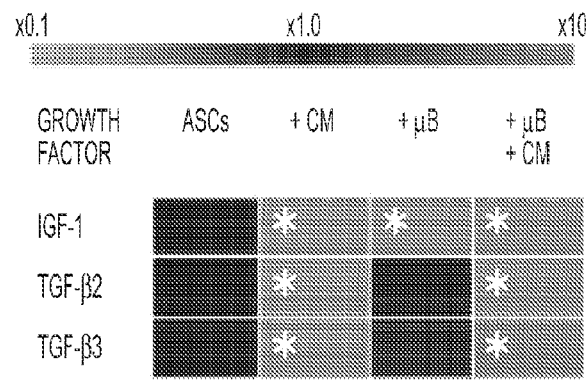
Figure 8D:
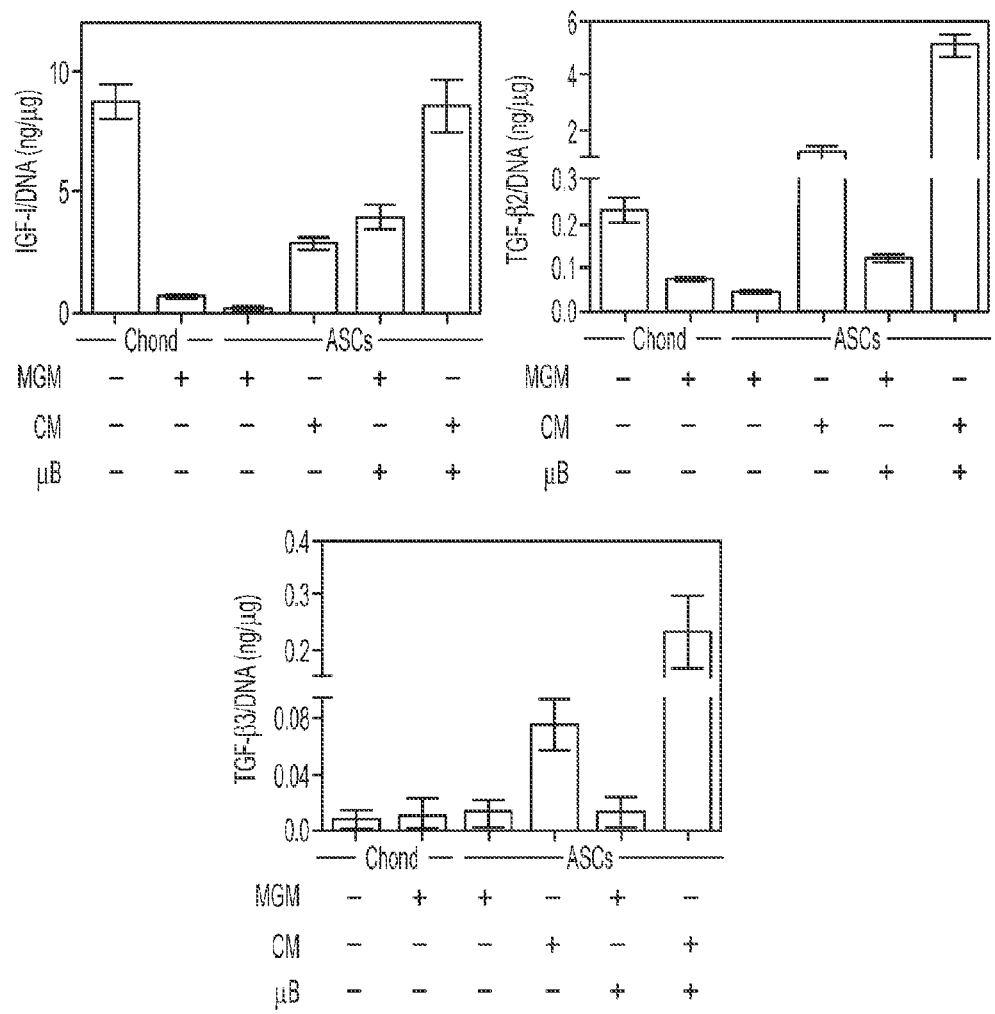
Figure 9A:
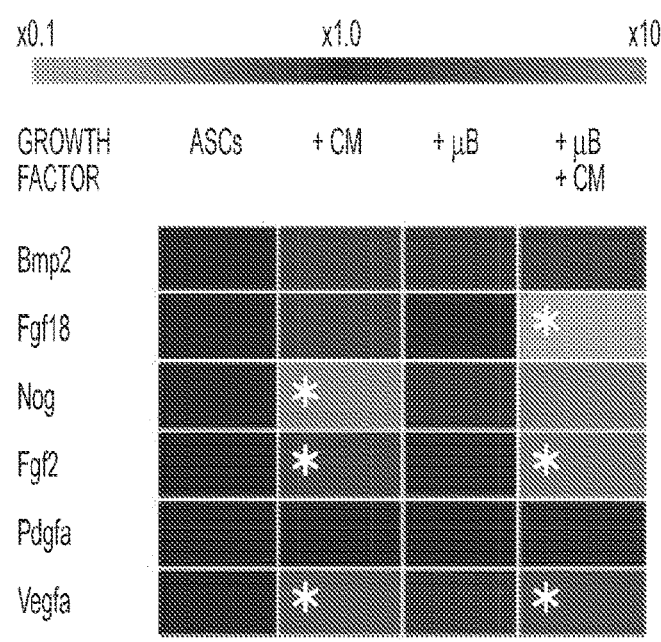
FIG. 9 shows the effect of microencapsulation and chondrogenic medium (CM) on angiogenic, hypertrophic, and anti-hypertrophic factor production on monolayer and microencapsulated (μB) rat ASCs. MGM=Lonza Mesenchymal Stem Cell Growth Media, Chond=chondrocytes, ASCs=adipose stem cells (n=4 experiments).
Figure 9B:
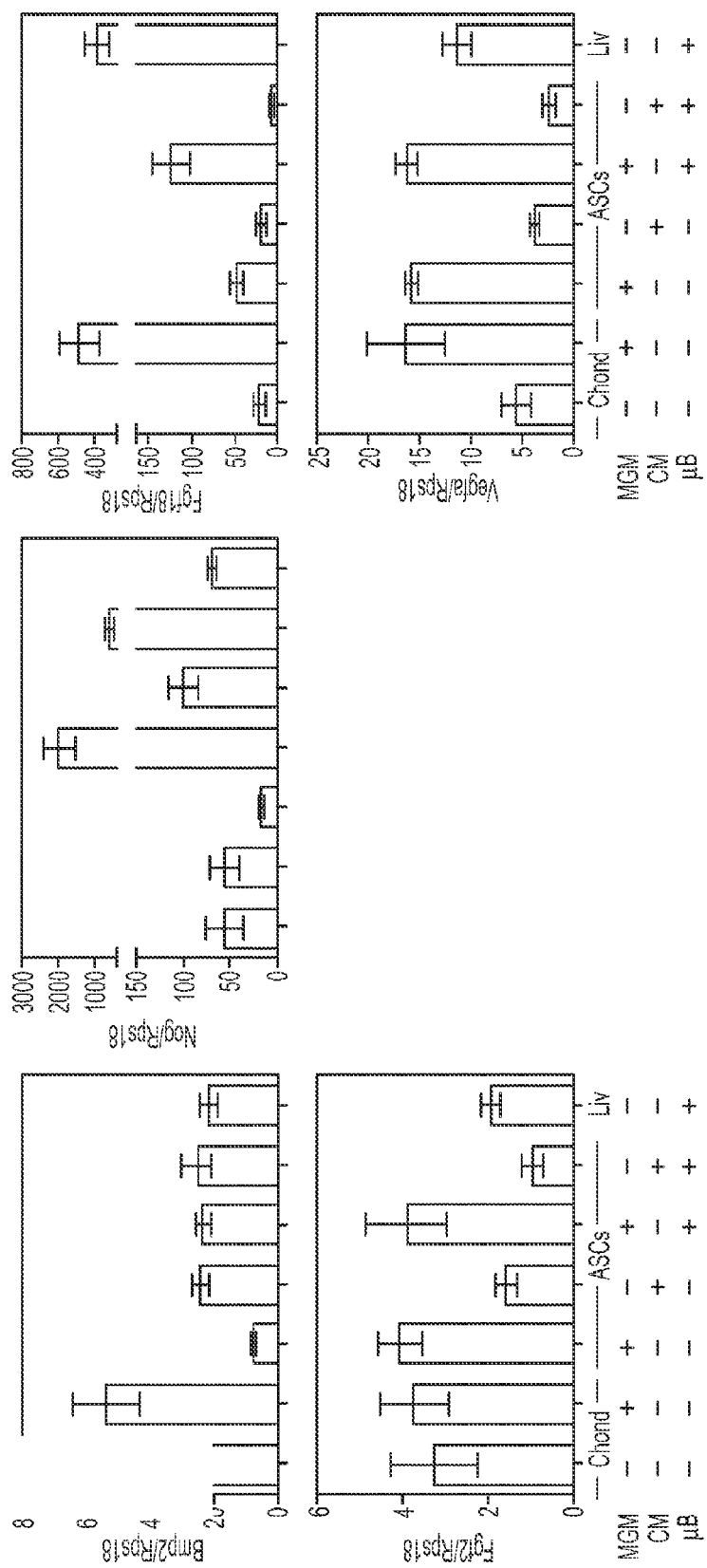
Figure 9C:
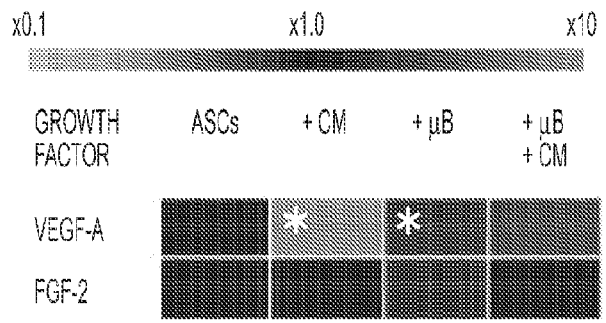
Figure 9D:
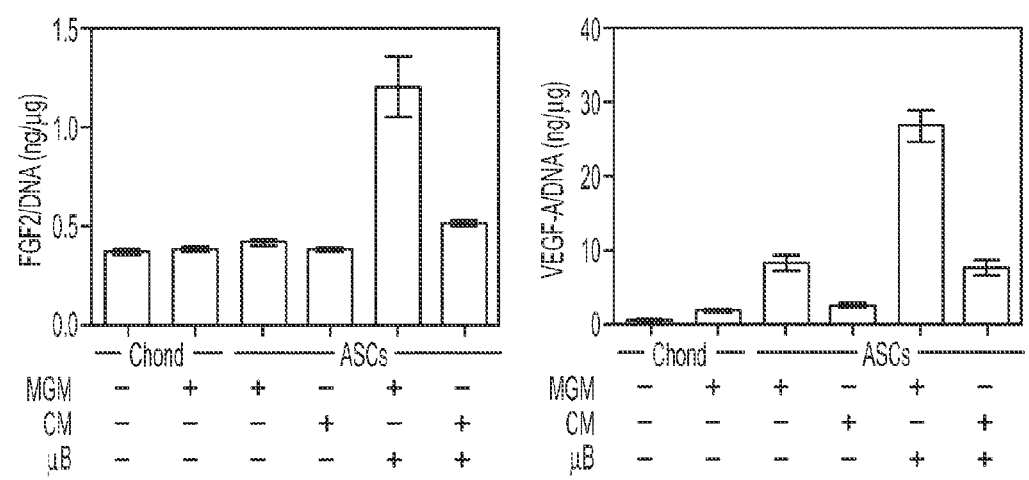

To determine the effect ASCs have on cartilage regeneration, ASC pellets were implanted in a 1 mm xiphoid cartilage defect. Scores of radiographic images showed that 7 of 7 defects with autografts had partial or full healing and empty defects had 3 of 7 defects with partial or full healing (FIG. 8A). However, only 1 of 7 defects with ASC pellets had partial healing whereas 4 of 7 defects with pellets of ASCs treated with chondrogenic media had partial or full healing. When EPIC-μCT was used to evaluate proteoglycan distribution in the defect, proteoglycan was visible in empty defects and defects with pellets of ASCs treated with chondrogenic medium but absent from defects with pellets of untreated ASCs (FIG. 8B). EPIC-μCT calculated cartilage volume for defects with ASC pellets was significantly smaller than cartilage volume in both autografts and empty defects. Defects with ASCs treated with chondrogenic media had more cartilage than defects with untreated ASCs, but were not different from empty defects (FIG. 8B).

In histological sections of defects with autografts, early-stage cartilage and infiltrating cells were starting to integrate the graft with the surrounding xiphoid (FIG. 5C). Similar tissue deposition and cell infiltration was observed for empty defects and defects with ASCs treated with chondrogenic media. However, defects with ASCs were infiltrated with surrounding epithelial tissue instead and lacked the connective tissue that was observed in empty defects.

Results

As shown in FIG. 8, chondrogenic medium significantly increased expression of chondrogenic factors Igf1, Tgfb2, and Tgfb3 in monolayer and microbead cultures. Microencapsulation significantly increased expression of chondrogenic factors Igf1 and Pthlh (gene for PTHrP). Chondrogenic medium significantly increased production of IGF-I, TGF-β2, TGF-β3 in monolayer and microbead cultures. Microencapsulating significantly increased production of chondrogenic factor IGF-1.

As shown in FIG. 9, chondrogenic medium increased expression of Noggin. Chondrogenic medium decreased expression of Fgf2 and Vegfa in monolayer and microbead cultures and Fgf18 in microbead cultures. Chondrogenic medium decreased secretion of VEGF-A in monolayer cultures. Microencapsulation increased production of VEGF-A.

Figure 10:
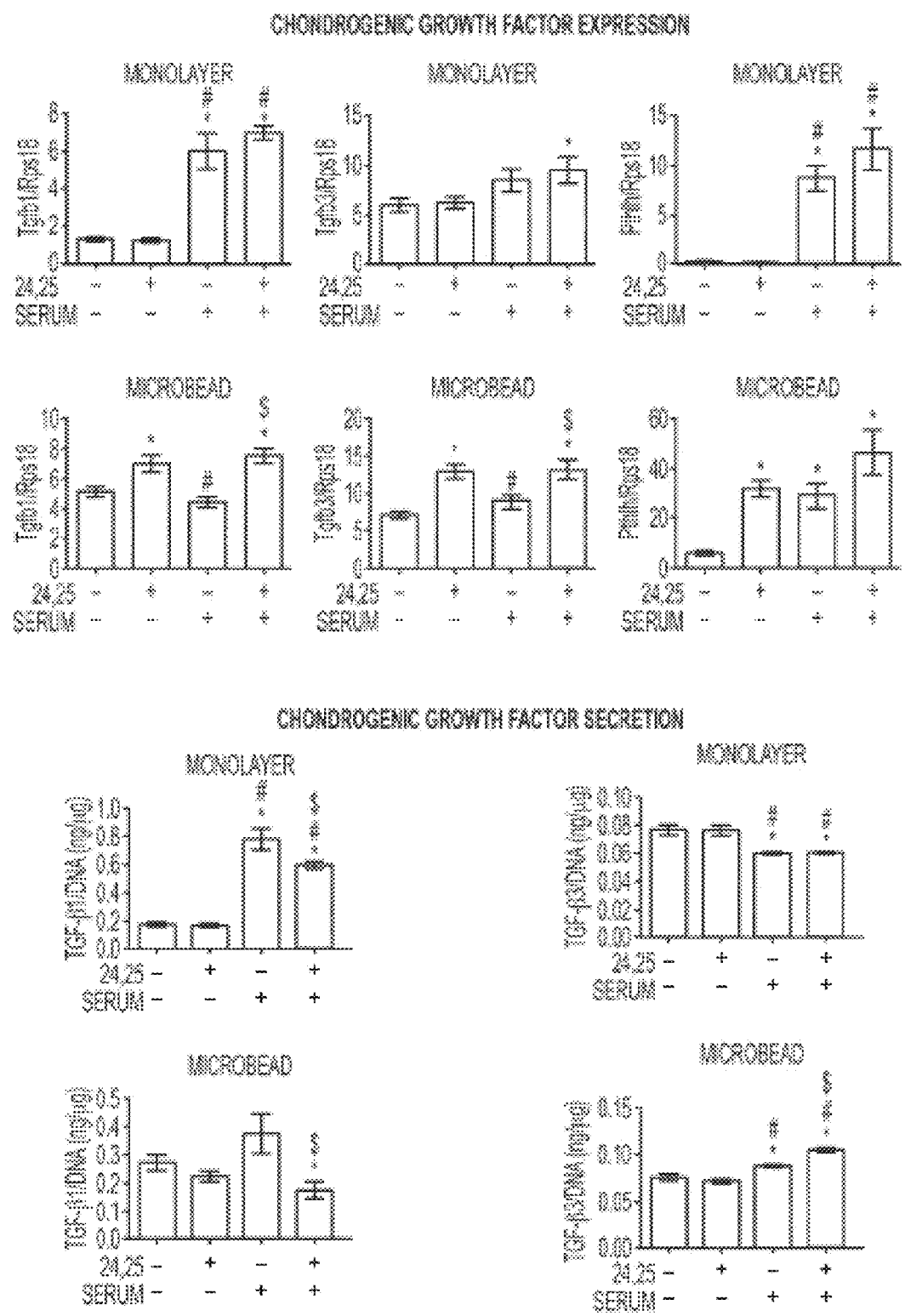
FIG. 10 shows the effect of 24R,25-dihydroxyvitamin D3 (24,25) and fetal bovine serum (serum) on chondrogenic factor production from monolayer and microencapsulated rat adipose stem cells (n=6 samples).

As shown in FIG. 10, serum increased the expression of Tgfb1 and Pthlh in monolayer cultures. 24,25 increased expression of Pthlh in microbead cultures without serum and increased expression of Tgfb1 and Tgfb3 in cultures with or without serum. Serum increased secretion of TGF-β1 in monolayers. Serum decreased secretion of TGF-β3 in monolayers. 24,25 increased secretion of TGF-β3 in microbeads.

Figure 11:
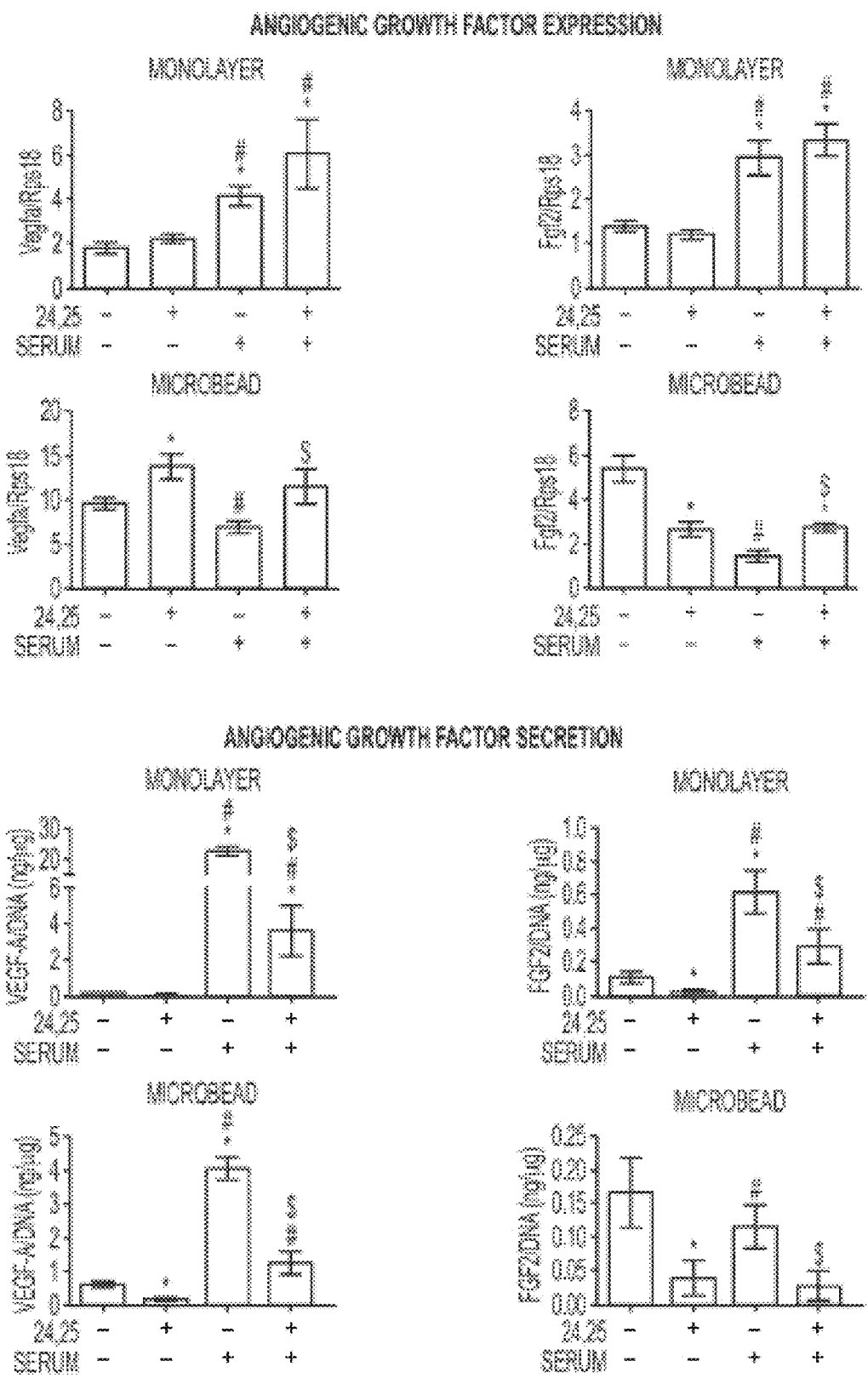
FIG. 11 shows the effect of 24R,25-dihydroxyvitamin D3 (24,25) and fetal bovine serum (serum) on angiogenic factor production from monolayer and microencapsulated rat adipose stem cells (n=6 samples).

As shown in FIG. 11, serum increased expression and secretion of Vegfa and Fgf2 in monolayer cultures. Serum increased secretion of VEGF-A and FGF-2 in monolayer cultures and VEGF-A in microbead cultures. 24,25 decreased secretion of VEGF-A and FGF-2 in monolayer and microbead cultures.

Figure 12:
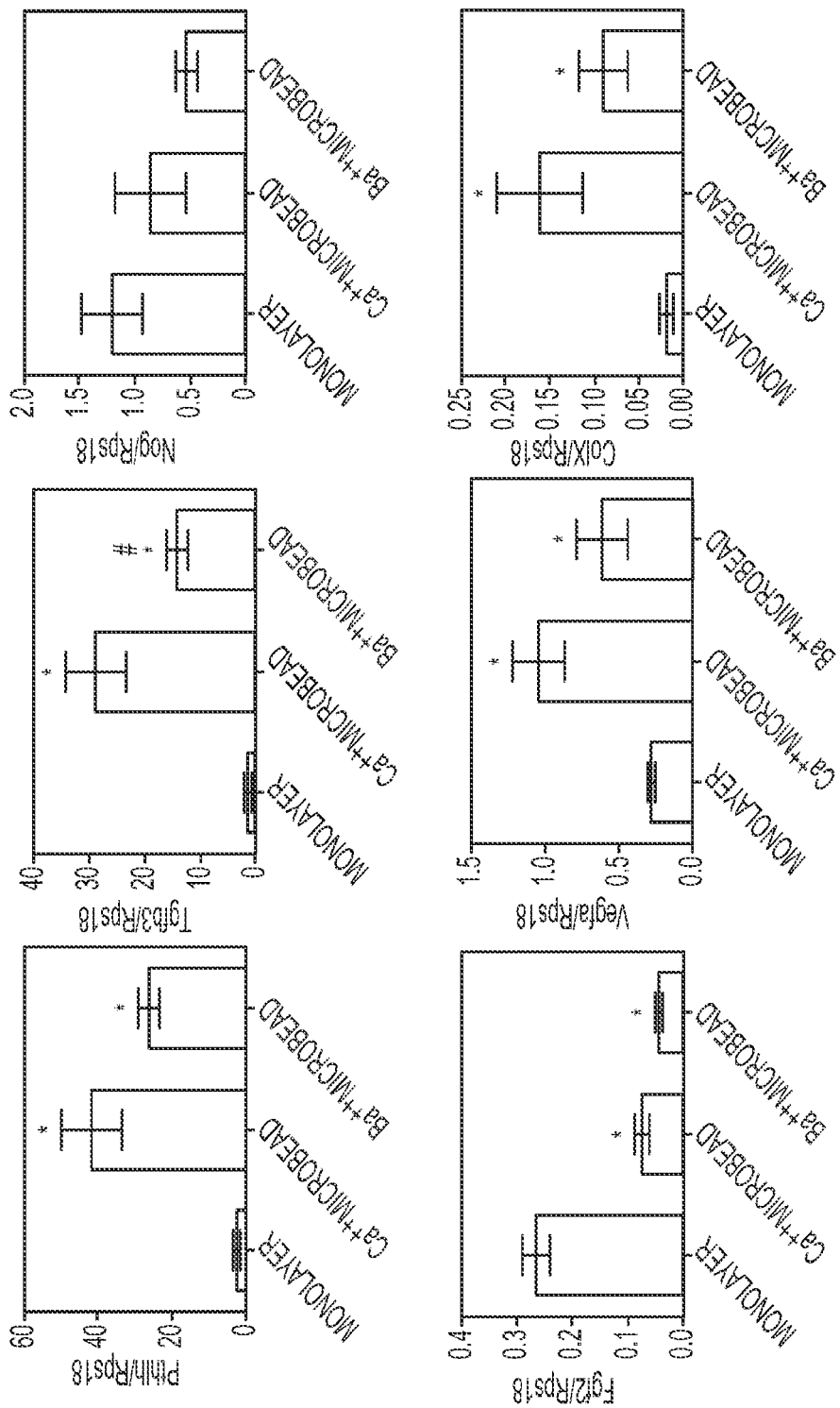
FIG. 12 shows the effect of $Ca^{++}$ on chondrogenic and angiogenic factor expression of microencapsulated human adipose stem cells (n=6 samples).

As shown in FIG. 12, microencapsulation increased the expression of Pthlh, Tgfb3 and Vegfa. Microencapsulation decreased the expression of Fgf2. $Ca^{++}$ was partially responsible for increases in Tgfb3.

Figure 13:
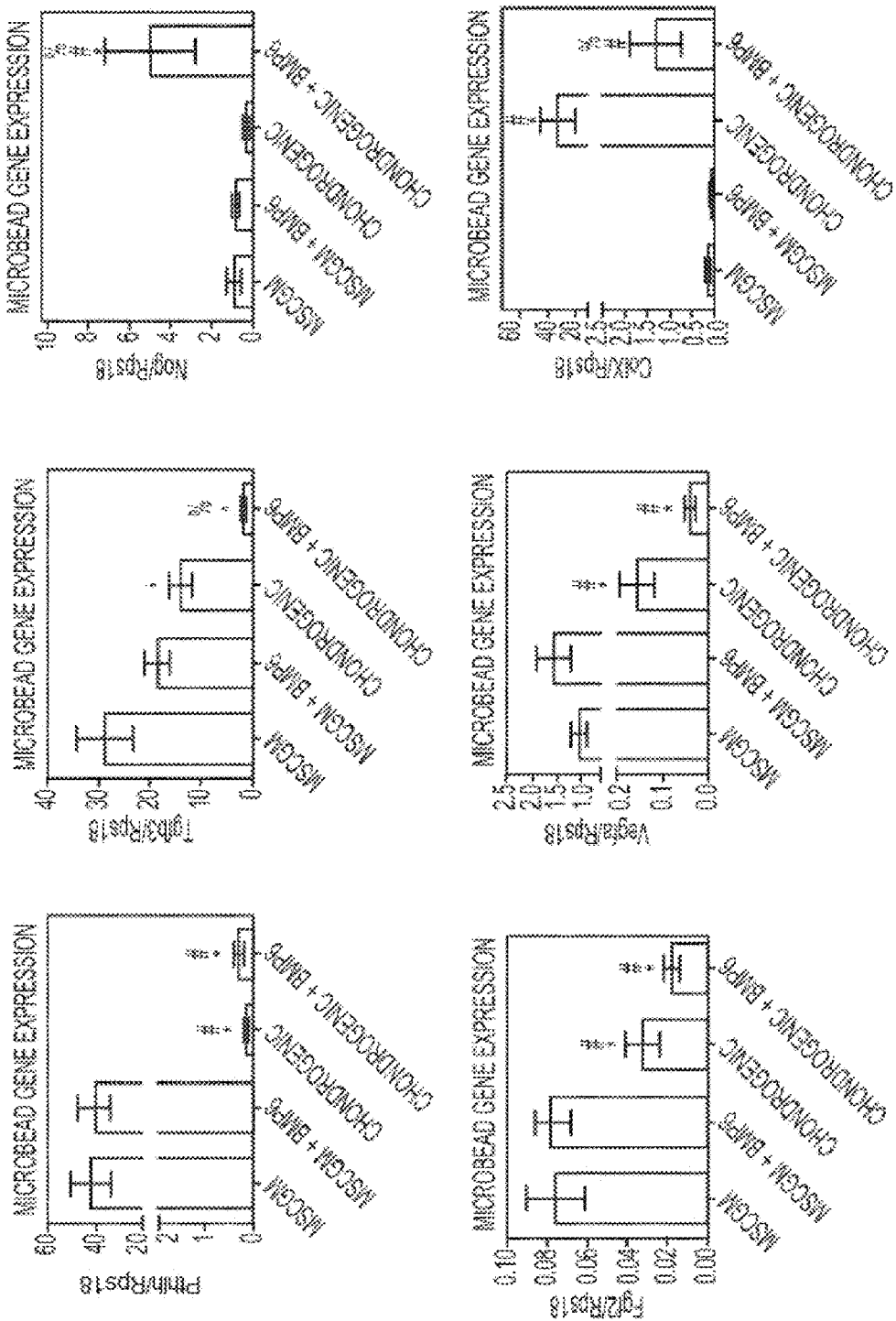
FIG. 13 shows the effect of BMP-6 on chondrogenic and angiogenic factor expression of microencapsulated human adipose stem cells (n=6 samples).

As shown in FIG. 13, BMP-6 was specifically responsible for decreasing expression of Tgfb3 and Vegfa in hASCs in chondrogenic medium. Adding BMP-6 to MSCGM did not increase or decrease expression of any measured growth factor. BMP-6 was specifically responsible for increasing Noggin in chondrogenic medium.

Figure 14:
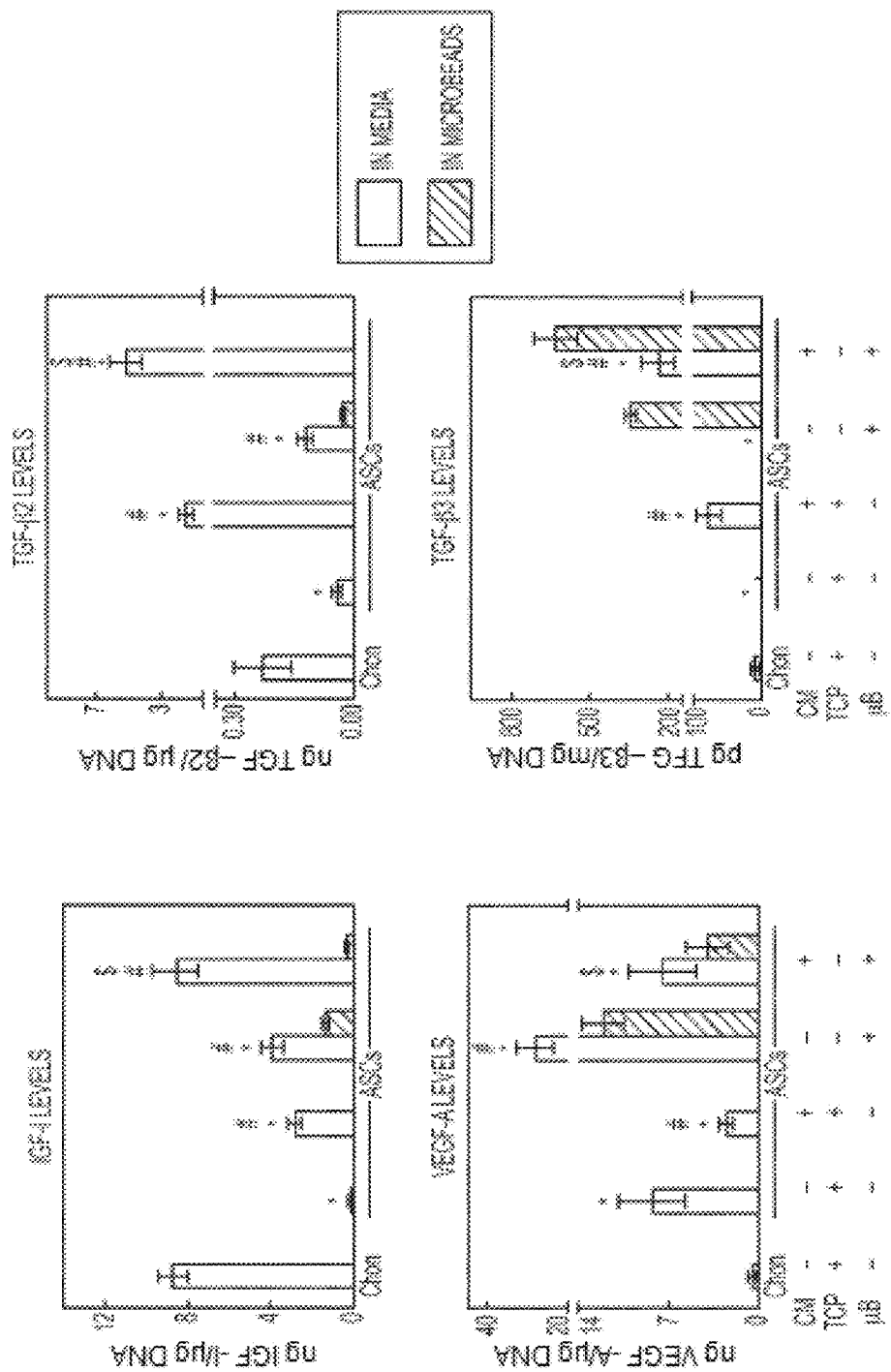
FIG. 14 shows growth factor secretion from and retention in microbeads (n=6 samples).
Figure 15:
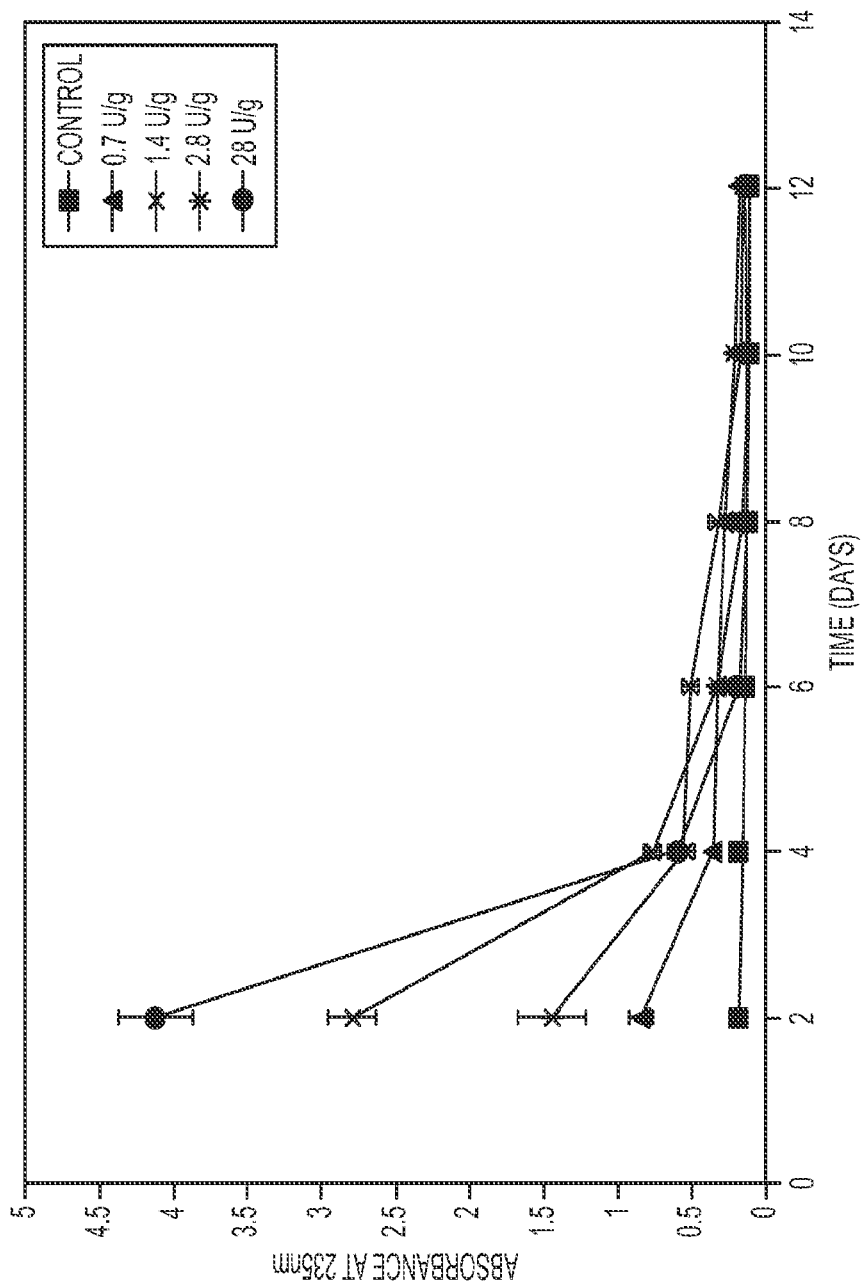
FIG. 15 shows release of uronate products from degrading alginate microbeads over a 12-day period with varying concentrations of incorporated alginate lyase.
Figure 16:
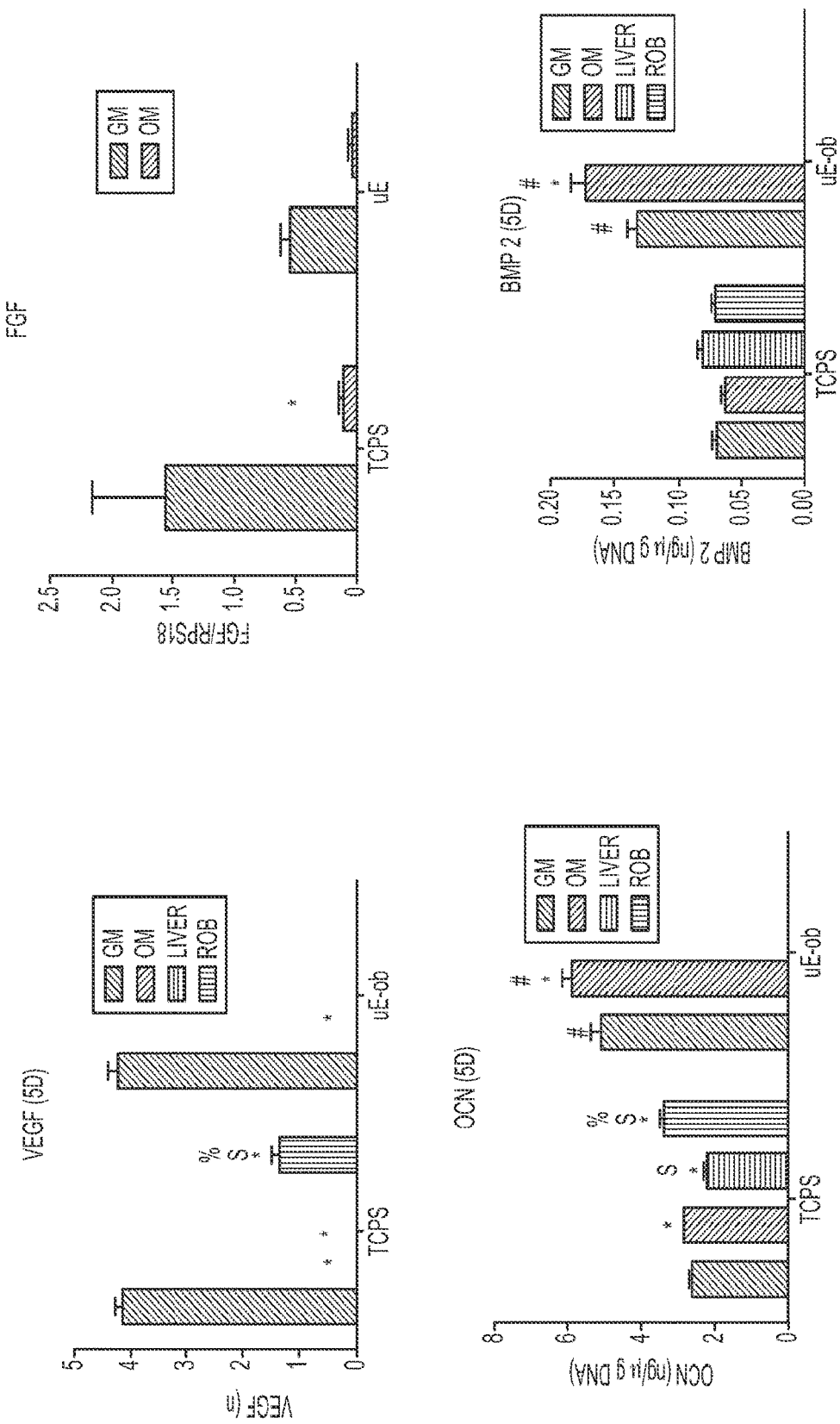
FIG. 16 shows the effect of osteogenic medium and microencapsulation on angiogenic and osteogenic factors (n=6+SE. *$p<0.05$ vs. GM, $$p<0.05$ vs. OM, % $p<0.05$ vs. liver, #$p<0.05$ vs. TCPS).

As shown in FIG. 14, VEGF-A and TGF-β3 were retained in the microbead. Little IGF-I or TGF-β2 were retained in the microbead.

Example 22

Incorporating Protease Cleavable Site (Method: Covalently Modifying Alginate with MMP-Cleavable Sites)

A protocol for covalently modifying MMP-cleavable and related peptide sequences has been developed and optimized (Rowley, J. A., G. Madlambayan, et al. (1999), "Alginate hydrogels as synthetic extracellular matrix materials," Biomaterials 20 (1): 45-53; Fonseca, K. B., S. J. Bidarra, et al. (2011), "Molecularly designed alginate hydrogels susceptible to local proteolysis as three-dimensional cellular microenvironments," Acta Biomater 7 (4): 1674-1682). Very low molecular weight, high mannuronate content alginate (VLVM, FMC BioPolymer) can be covalently modified with the 12 amino acid oligopeptide GGYGPVGLIGGK (SEQ ID NO:15) (custom-synthesized by GenScript, Piscataway, N.J.) (Fonseca, K. B., S. J. Bidarra, et al. (2011). "Molecularly designed alginate hydrogels susceptible to local proteolysis as three-dimensional cellular microenvironments." Acta Biomater 7 (4): 1674-1682). The cleavage site is the peptide bond between the glycine (G) and the leucine (L). Lysine (K) can be inserted near the C-terminus to provide an additional primary amino group for the coupling reaction and to yield a double-end grafted peptide. Tyrosine (Y) can be included for subsequent detection via UV spectroscopy and G spacers can be incorporated to increase accessibility of the target MMP-site. 10 mg/ml LVM can be added to 0.1 M MES buffer (Sigma) and 0.3 M NaCl (pH=6.5) and dissolved overnight at room temperature. N-Hydroxy-sulfosuccinimide (Fisher) and 1-ethyl-(dimethylaminopropyl)-carbodiimide (Sigma) at a molar ratio of 1:2 and 10 mg peptide/g alginate can then be added. After 20 hours at room temperature, the reaction can then be quenched with 180 mg hydroxylamine and unreacted species can be separated from the polymer by dialysis (MWCO 3500) for 3 days. The MMP-cleavable alginate solution can then be sterile filtered (0.2 μm) and lyophilized. Peptide grafting will be quantified using UV absorbance spectra in the 200-300 nm region and a BCA protein quantification kit (Fisher) (Fonseca, K. B., S. J. Bidarra, et al. (2011), "Molecularly designed alginate hydrogels susceptible to local proteolysis as three-dimensional cellular microenvironments," Acta Biomater 7 (4): 1674-1682). Double-ended grafting can be quantified using a fluorescamine assay (Lorenzen, A. and S. W. Kennedy (1993), "A Fluorescence-Based Protein Assay for Use with a Microplate Reader," Analytical Biochemistry 214 (1): 346-348). 50 μL 10 mg/ml alginate solutions in Tricine Buffer (50 mMTricine, 200 mMNaCl, pH 7.5, Sigma) will be reacted with 100 μl of 0.375 mM fluorescamine in acetone and measured (390 nm excitation, 470 nm emission). Fluorescence readings can then be converted into concentration of free amino groups using glycine solutions as standards. The amount of free amines corresponds to tethered (single-end grafted) peptide. Subtraction of this amount from the total amount of immobilized peptide reveals the extent of double-ended grafting.

Example 23

Incorporating Site that is Susceptible to Hydrolysis (Method: Alginate Oxidation)

A protocol for oxidizing alginate has been optimized over numerous studies (Bouhadir, Hausman et al. 1999; Bouhadir, Lee et al. 2001; Boontheekul, Kong et al. 2005). A 10 mg/mL solution of low molecular weight, high mannuronate content alginate (LVM, FMC BioPolymer, Sandvika, Norway) (8.0 g, 40.4 mmoluronate) in distilled water can be mixed with an aqueous solution of 0.25 M sodium periodate (2.0 mmol) (Sigma, St. Louis, Mo.) in the dark at room temperature. After 24 hours the reaction can be stopped by the addition of an equimolar amount of ethylene glycol (Fisher, Pittsburgh, Pa.) (Bouhadir, Hausman et al. 1999). The solution can then be dialyzed (MWCO 1000, Spectra/Por, Rancho Dominguez, Calif.) for 3 days, sterile filtered (0.2 μm), and lyophilized. The extent of oxidation can be quantified by measuring the number of aldehydes in these polymers using t-butyl carbazate (Sigma) (Bouhadir, Hausman et al. 1999). Excess carbazate can be added to the polymer solution, reacting with the aldehydes to form stable carbazones. The quantity of unreacted carbazate will be determined by adding a TNBS solution (Sigma), and measuring the absorbance of the colored complex (trinitrophenyl derivative) that forms at 334 nm. Aqueous formalin solutions varying in concentration can be used to calibrate the assay to aldehyde concentration.

Bouhadir, K. H., D. S. Hausman, et al. (1999). "Synthesis of cross-linked poly(aldehyde guluronate) hydrogels." Polymer 40 (12): 3575-3584

Bouhadir, K. H., K. Y. Lee, et al. (2001). "Degradation of partially oxidized alginate and its potential application for tissue engineering." Biotechnol Prog 17 (5): 945-950

Boontheekul, T., H. J. Kong, et al. (2005). "Controlling alginate gel degradation utilizing partial oxidation and bimodal molecular weight distribution." Biomaterials 26 (15): 2455-2465.

Example 24

Adding a Chelator, Lower Ionic Binding Affinity Cross-Linker

Chitosan Microparticle Formation

Chitosan microparticles can be fabricated using an oil-in-water single emulsion (Jayasuriya and Bhat 2009; Bhat, Dreifke et al. 2010). 5 mL of 15 mg/mL Protasan UP CL 113 (FMC BioPolymer, ~150 kDA) dissolved in 1% acetic acid at room temperature can be filtered (0.2 μm) to remove insoluble components. The chitosan solution can then be mixed with an equal volume of acetone. This mixture (9 ml) can then be emulsified into 60 mL of corn oil (Sigma) containing 1 mL Tween 20 (Sigma) by homogenizing at 5000 RPM for 5 minutes using a PT3100 (Kinematica), then incubated at 37° C. under agitation at 870 rpm for 14 hours. 1 mL of 64 mg/mL tripolyphosphate (TPP, Sigma) can then be added to cross-link the chitosan microparticles. After 4 hours, an equal volume of hexane is added and the solution can be vacuum filtered (0.2 μm), air dried, washed 3 times in DI water, and lyophilized.

Microencapsulation

Molar ratios of 1:0, 25:75, 50:50, 75:25, and 0:1 of $CaSO_4$ or $CaCO_3$ and chitosan can be dissolved in saline at 5 mg/mL. The $CaSO_4$/chitosan solution can then be mixed with 20 mg/mL VLVM and 10 mg/mL LVM alginates at a 1:1 volume ratio as previous described (Cohen, Malone et al. 2006; Lee, Gleghorn et al. 2007). Microencapsulation can be performed as described above, but $CaCl_2$ concentration can be varied between 0 and 50 mM. 20 mg/mL LVM alginate microbeads can serve as a control. Additionally, varying concentrations of a calcium chelator (sodium citrate) can be added to the alginate and crosslinking solutions at concentrations ranging from 0 to 50 mM.

Cohen, D. L., J. I. Lipton, et al. (2010). "Additive manufacturing for in situ repair of osteochondral defects." Biofabrication 2 (3): 035004

Lee, C. S., J. P. Gleghorn, et al. (2007). "Integration of layered chondrocyte-seeded alginate hydrogel scaffolds." Biomaterials 28 (19): 2987-2993

Example 25

Alginate Lyase or Chelator is Released from a Secondary Nanoparticle or Microparticle Method: Encapsulation of Alginate Lyase Agarose microparticles can be fabricated using a water-in-oil single emulsion similar to previously described methods (Wang and Wu 1997; Bratt-Leal, Carpenedo et al. 2011). 30 mg/mL solution (2 mL) of Ultra-low melt SeaPrepAgarose (Lonza, Rockland, Me.) can be prepared in deionized (dI) water at 60° C. The agarose solution can then be added drop-wise to 60 mL of corn oil (Sigma) containing 1 mL Tween 20 (Sigma). An emulsion can then be created by homogenizing at 5000 RPM for 5 minutes using a PT3100 (Kinematica, Switzerland). The emulsion can be cooled at 4° C. for 20 minutes and agarose microparticles can be retrieved through centrifugation at 200 g for 10 minutes and washed 3 times with 25 mL of dI water to remove residual oil. Samples can then be lyophilized and stored at −80° C. prior to experiments. Upon the initiation of each experiment, the lyophilized particles can be rehydrated in a 1 mL solution of DI water containing 10 mg (~100 units) of alginate lyase (Sigma). Depending on the results, alternative methods of encapsulation include using gelatin (Tabata, Hijikata et al. 1999; Bratt-Leal, Carpenedo et al. 2011) and chondroitin sulfate (Lim, Hammoudi et al. 2011).

Wang, N. and X. S. Wu (1997). "Preparation and characterization of agarose hydrogel nanoparticles for protein and peptide drug delivery." Pharm Dev Technol 2 (2): 135-142

Bratt-Leal, A. M., R. L. Carpenedo, et al. (2011). "Incorporation of biomaterials in multicellular aggregates modulates pluripotent stem cell differentiation." Biomaterials 32 (1): 48-56

Tabata, Y., S. Hijikata, et al. (1999). "Neovascularization effect of biodegradable gelatin microspheres incorporating basic fibroblast growth factor." J Biomater Sci Polym Ed 10 (1): 79-94

Lim, J. J., T. M. Hammoudi, et al. (2011). "Development of nano- and microscale chondroitin sulfate particles for controlled growth factor delivery." Acta Biomater 7 (3): 986-995

Example 26

Adding Enzyme Directly to the Alginate Microbead (at a Lower Temperature)

Preparation of Alginate/Lyase Solution
4% LVM alginate
1. Dissolve 2.0 g LVM alginate in 50 ml saline
2. Mix until completely dissolved on the stir plate with magnetic stir bar Alginate Lyase Stock Solutions
10 U/ml Alginate Lyase stock
Dissolve 3.6 mg alginate lyase powder in 10 ml of saline to make 10 U/ml alginate lyase stock, vortex until dissolved
5 U/ml Alginate Lyase stock
Make 5 ml of 5 U/ml alginate lyase by adding 2.5 ml of 10 U/ml alginate lyase stock to 2.5 ml of saline Cool solutions to 4° C. or place on ice.

Table 3 shows different ratios of alginate lyase to alginate

TABLE 3

| Ratio (w/w) | alginate lyase:alginate (U:g) | Alginate Lyase 5 U/ml stock (ml) | Saline (ml) | Final Concentration of Alginate lyase |
|---|---|---|---|---|
| 1:40000 | 0.7 | 0.028 | 4.97 | 0.07 U/ml |
| 1:20000 | 1.4 | 0.056 | 4.94 | 0.08 U/ml |
| 1:10000 | 2.8 | 0.112 | 4.89 | 0.093 U/ml |
| 1:1000 | 28 | 1.12 | 3.88 | 0.112 U/ml |

Preparation of Alginate Microbeads
For example for 1:1000 (w/w) alginate lyase:alginate
In the mixture of alginate lyase/alginate the weight/weight ratio is 0.02 mg of alginate lyase:200 mg of alginate which is equivalent to 1:1000 (w/w)
1. Mix 5 ml of 4% LVM alginate with 5 ml of 0.07 U/ml alginate lyase at 4° C.
2. Mix at 1000 rpm for 1 minute at 4° C.
3. Use 1.8 ml of this mixture to form alginate microbeads with a microencapsulator using a cross linking solution of 75 mM $CaCl_2$ (pH 7.34) at 4° C.
4. The beads were rinsed in water twice and then suspended in 1.8 mM $CaCl_2$ at 4° C.

Example 27

Preparation of Alginate Lyase/Alginate Solution

Sterile low molecular weight alginate with a high mannuronate to guluronate ratio (40% guluronate) is dissolved in saline at a concentration of 40 mg/mL. A solution of alginate lyase in saline is also made at a concentration of 5 units/mL. The alginate and alginate lyase solutions are then cooled down to 4° C. Once at 4° C., the solutions are mixed to form final alginate lyase (units):alginate (g) ratios ranging from 0.5 to 100. This alginate lyase/alginate solution is then used to microencapsulate cells as previously described, except at 4° C. and using a cross-linking solution containing 75 mM $CaCl_2$, 92 mM glucose, and 15 mM 4-(2-hydroxyethyl)-1-piperazineethanesulfonic acid (pH=7.3, Sigma). Once fabricated, microbeads can be returned to physiological temperature (37° C.).

The following examples relate to treating mesenchymal stem cells, in particular adipose stem cells, with osteogenic media to decrease production of angiogenic factors and increase production of osteogenic factors.

Example 28

Isolation of Cells

ASCs were isolated from the inguinal fat pad of 125 g Sprague Dawley rats (Harlan Laboratories, Indianapolis, Ind., USA)[14,15], from human donors according to an approved IRB protocol, or from Lonza (PT 5006). Briefly, rat fat pads were washed three times in Dulbecco's Modified Eagle Medium (DMEM, Invitrogen, Carlsbad, Calif., USA) with 3% penicillin and streptomycin (Invitrogen) and incubated in trypsin (Invitrogen) for 30 minutes. Fat pads were then diced and digested in 150 units/mL collagenase (Sigma, St. Louis, Mo., USA) and 3 units/mL dispase (Invitrogen) in DMEM for four hours. ASCs were then pelleted and seeded at 5,000 cells/$cm^2$ in LonzaMesenchymal Stem Cell Growth Medium (MSCGM, Lonza Walkersville, Md., USA). After one passage, these cells were positive for CD73 and CD271 and negative for CD45 [15].

Example 29

Microencapsulation

Once primary ASCs reached 90% confluence, cells were trypsinized and the first passaged ASCs were then microencapsulated. Low molecular weight (~150 kDa) alginate with a high mannuronate to guluronate ratio (40% guluronate) was UV light sterilized overnight and dissolved in 155 mM sodium chloride (Ricca Chemical, Arlington, Tex., USA) at a concentration of 20 mg/mL. ASCs were then seeded at $25 \times 10^6$ cells/mL, and microspheres were created using a Nisco Encapsulator VAR Vi LIN-0043 (Nisco Engineering AG, Zurich, Switzerland) at a 5 mL/hr flow rate, 0.175 mm nozzle inner diameter, and 6 kV/cm electrostatic potential [12,18]. Microbeads were cross-linked in a solution containing 50 mM $CaCl_2$, 150 mM glucose, and 15 mM 4-(2-hydroxyethyl)-1-piperazineethanesulfonic acid (pH=7.3, Sigma) for 15 minutes. The microbeads were washed 3 times in MSCGM prior to cell culture studies. First passaged ASCs were also plated in 6-well plates (FIG. 3A).

Example 30

ASC Cell Culture

Once first passaged ASCs reached 90% confluence, ASC monolayers and microbeads were then treated for 5 days (14 days for hASCs) with MSCGM, osteogenic medium (OM, Lonza Walkersville, Md., USA) with L-glutamine, dexamethasone, beta-glycerophosphate, and ascorbic acid. Once media were changed on the fifth/fourteenth day, RNA was collected after 8 hours as described below while media and ASCs lysed in 0.05% Triton X-100 were collected after 24 hours. Monolayer fourth passaged osteoblasts and kidney cells (HEK 239) were cultured in DMEM, 10% FBS, and Sprague Dawley-derived clone 9 liver cells (ATCC, Manassas, Va., USA) cultured in F12K medium and 10% FBS served as controls. All media contained 1% penicillin and streptomycin.

Example 31

Growth Factor Expression and Production

Microbeads were uncross-linked in 82.5 mM sodium citrate (Sigma), pelleted at 500 g for 10 minutes and washed 2 more times in sodium citrate to remove any residual alginate. TRIzol reagent (Invitrogen) was added to the resulting cell pellet, homogenized using a QIAshredder (QIAGEN, Valencia, Calif., USA), and RNA was isolated using chloroform. 1 μg RNA was then reverse transcribed to cDNA using a High Capacity Reverse Transcription cDNA kit (Applied Biosystems, Carlsbad, Calif., USA). Expression of growth factors genes were quantified as previously described using real-time PCR with gene-specific primers using the Step One Plus Real-time PCR System and Power Sybr® Green Master Mix (Applied Biosystems) [20]. Primers were designed using Beacon Designer software (Premier Biosoft, Palo Alto, Calif., USA) and synthesized by Eurofins MWG Operon (Huntsville, Ala., USA) unless otherwise noted (Table 3). Bone Morphogenetic Protein 2 (BMP2), Osteoprotegerin (OPG), VEGF-A, FGF-2, and osteocalcin (OCN) production over the last 24 hours of culture was quantified using ELISA (R&D Systems) and a radioimmunoassay for the OCN (BTI Inc. Stoughton, Mass., USA) and normalized to DNA content measured with a Quant-iTPicoGreen kit (Invitrogen).

REFERENCES

1. Giordano, A., U. Galderisi, I. R. Marino, From the laboratory bench to the patient's bedside: an update on clinical trials with mesenchymal stem cells. J Cell Physiol 2007; 211:27-35.
2. Gimble, J. M. F. Guilak, Differentiation potential of adipose derived adult stem (ADAS) cells. Curt Top Dev Biol 2003; 58:137-60.
3. Gimble, J. F. Guilak, Adipose-derived adult stem cells: isolation, characterization, and differentiation potential. Cytotherapy 2003; 5:362-9.
4. Baraniak, P. R. T. C. McDevitt, Stem cell paracrine actions and tissue regeneration. Regen Med 2010; 5:121-43.
5. Macchiarini, P., M. Birchall, A. Hollander, et al., Clinical transplantation of a tissue-engineered airway Authors' reply. Lancet 2009; 373:718-719.
6. Mobasheri, A., C. Csaki, A. L. Clutterbuck, et al., Mesenchymal stem cells in connective tissue engineering and regenerative medicine: applications in cartilage repair and osteoarthritis therapy. Histol Histopathol 2009; 24:347-66.
7. Hou, N., P. Cui, J. Luo, et al., Tissue-engineered larynx using perfusion-decellularized technique and mesenchymal stem cells in a rabbit model. Acta Otolaryngol 2011; 131:645-52.
8. Gomez-de-Antonio, D., M. Zurita, M. Santos, et al., Stem cells and bronchial stump healing. J Thorac Cardiovasc Surg 2010; 140:1397-401.
9. McCarty, R. C., C. J. Xian, S. Gronthos, et al., Application of autologous bone marrow derived mesenchymal stem 9. cells to an ovine model of growth plate cartilage injury. Open Orthop J 2010; 4:204-10.
10. Kim, B. S., K. S. Kang, S. K. Kang, Soluble factors from ASCs effectively direct control of chondrogenic fate. Cell Prolif 2010; 43:249-61.
11. Endres, M., N. Wenda, H. Woehlecke, et al., Microencapsulation and chondrogenic differentiation of human mesenchymal progenitor cells from subchondral bone marrow in Ca-alginate for cell injection. Acta Biomater 2010; 6:436-44.
12. Moyer, H. R., R. C. Kinney, K. A. Singh, et al., Alginate microencapsulation technology for the percutaneous delivery of adipose-derived stem cells. Ann Plast Surg 2010; 65:497-503.
13. Grellier, M., P. L. Granja, J. C. Fricain, et al., The effect of the co-immobilization of human osteoprogenitors and endothelial cells within alginate microspheres on mineralization in a bone defect. Biomaterials 2009; 30:3271-8.
14. Dosier, C. R., C. P. Erdman, J. H. Park, et al., Resveratrol effect on osteogenic differentiation of rat and human adipose derived stem cells in a 3-D culture environment. Journal of the Mechanical Behavior of Biomedical Materials 2011; In Press.
15. Erdman, C. P., C. R. Dosier, R. Olivares-Navarrete, et al., Effects of Resveratrol on Enrichment of Adipose-derived Stem Cells and their Differentiation to Osteoblasts in Two and Three Dimensional Cultures. Journal of Tissue Engineering and Regenerative Medicine 2011; In Press.
16. Boyan, B. D., Z. Schwartz, L. D. Swain, et al., Differential expression of phenotype by resting zone and growth region costochondral chondrocytes in vitro. Bone 1988; 9:185-94.
17. Hurst-Kennedy, J., M. Zhong, V. Gupta, et al., 24R,25-Dihydroxyvitamin D3, lysophosphatidic acid, and p53: a signaling axis in the inhibition of phosphate-induced chondrocyte apoptosis. J Steroid Biochem Mol Biol 2010; 122:264-71.
18. Lee, C. S., H. R. Moyer, R. A. Gittens, et al., Regulating in vivo calcification of alginate microbeads. Biomaterials 2010; 31:4926-34.
19. Fitzgerald, J. B., M. Jin, D. Dean, et al., Mechanical compression of cartilage explants induces multiple time-dependent gene expression patterns and involves intracellular calcium and cyclic AMP. J Biol Chem 2004; 279:19502-11.
20. Olivares-Navarrete, R., S. L. Hyzy, J. H. Park, et al., Mediation of osteogenic differentiation of human mesenchymal stem cells on titanium surfaces by a Wnt-integrin feedback loop. Biomaterials 2011; 32:6399-411.
21. Schwartz, Z., D. L. Schlader, V. Ramirez, et al., Effects of vitamin D metabolites on collagen production and cell proliferation of growth zone and resting zone cartilage cells in vitro. J Bone Miner Res 1989; 4:199-207.
22. O'Keefe, R. J., J. E. Puzas, J. S. Brand, et al., Effects of transforming growth factor-beta on matrix synthesis by chick growth plate chondrocytes. Endocrinology 1988; 122:2953-61.
23. Nasatzky, E., Z. Schwartz, B. D. Boyan, et al., Sex-dependent effects of 17-beta-estradiol on chondrocyte differentiation in culture. J Cell Physiol 1993; 154:359-67.
24. Schwartz, Z., V. L. Sylvia, D. D. Dean, et al., The synergistic effects of vitamin D metabolites and transforming growth factor-beta on costochondral chondrocytes are mediated by increases in protein kinase C activity involving two separate pathways. Endocrinology 1998; 139:534-45.
25. Raines, A. L., R. Olivares-Navarrete, M. Wieland, et al., Regulation of angiogenesis during osseointegration by titanium surface microstructure and energy. Biomaterials 2010; 31:4909-17.
26. Moyer, H. R., Y. Wang, T. Farooque, et al., A new animal model for assessing cartilage repair and regeneration at a nonarticular site. Tissue Eng Part A 2010; 16:2321-30.
27. Singh, K., H. Moyer, J. K. Williams, et al., Fibrin glue: a scaffold for cellular-based therapy in a critical-sized defect. Ann Plast Surg 2011; 66:301-5.
28. Palmer, A. W., R. E. Guldberg, M. E. Levenston, Analysis of cartilage matrix fixed charge density and three-dimensional morphology via contrast-enhanced microcomputed tomography. Proc Natl Acad Sci USA 2006; 103:19255-60.
29. Polacek, M., J. A. Bruun, J. Elvenes, et al., The secretory profiles of cultured human articular chondrocytes and mesenchymal stem cells: implications for autologous cell transplantation strategies. Cell Transplant 2010.
30. Rehman, J., D. Traktuev, J. Li, et al., Secretion of angiogenic and antiapoptotic factors by human adipose stromal cells. Circulation 2004; 109:1292-8.
31. Rubina, K., N. Kalinina, A. Efimenko, et al., Adipose stromal cells stimulate angiogenesis via promoting progenitor cell differentiation, secretion of angiogenic factors, and enhancing vessel maturation. Tissue Eng Part A 2009; 15:2039-50.
32. Kilroy, G. E., S. J. Foster, X. Wu, et al., Cytokine profile of human adipose-derived stem cells: expression of angiogenic, hematopoietic, and pro-inflammatory factors. J Cell Physiol 2007; 212:702-9.
33. Robinson, C. J. S. E. Stringer, The splice variants of vascular endothelial growth factor (VEGF) and their receptors. J Cell Sci 2001; 114:853-65.
34. Connolly, D. T., D. M. Heuvelman, R. Nelson, et al., Tumor vascular permeability factor stimulates endothelial cell growth and angiogenesis. J Clin Invest 1989; 84:1470-8.
35. Pufe, T., V. Harde, W. Petersen, et al., Vascular endothelial growth factor (VEGF) induces matrix metalloproteinase expression in immortalized chondrocytes. J Pathol 2004; 202:367-74.
36. Schweigerer, L., G. Neufeld, J. Friedman, et al., Capillary endothelial cells express basic fibroblast growth factor, a mitogen that promotes their own growth. Nature 1987; 325:257-9.
37. Deckers, M. M., M. Karperien, C. van der Bent, et al., Expression of vascular endothelial growth factors and their receptors during osteoblast differentiation. Endocrinology 2000; 141:1667-74.
38. Kim, J. H., M. C. Lee, S. C. Seong, et al., Enhanced proliferation and chondrogenic differentiation of human synovium-derived stem cells expanded with basic fibroblast growth factor. Tissue Eng Part A 2011; 17:991-1002.
39. Perrier, E., M. C. Ronziere, R. Bareille, et al., Analysis of collagen expression during chondrogenic induction of human bone marrow mesenchymal stem cells. Biotechnol Lett 2011.
40. Nishizawa, K., S. Imai, T. Mimura, et al., In-advance trans-medullary stimulation of bone marrow enhances spontaneous repair of full-thickness articular cartilage defects in rabbits. Cell Tissue Res 2010; 341:371-9.
41. Argun, M., M. Oner, A. Guney, et al., The healing of full-thickness articular cartilage defects in rabbits: suc- 41. cessful results with fibroblast growth factor. Eklem Hastalik Cerrahisi 2010; 21:147-52.
42. Hashimoto, S., L. Creighton-Achermann, K. Takahashi, et al., Development and regulation of osteophyte formation during experimental osteoarthritis. Osteoarthritis Cartilage 2002; 10:180-7.
43. Pfander, D., D. Kortje, R. Zimmermann, et al., Vascular endothelial growth factor in articular cartilage of healthy and osteoarthritic human knee joints. Ann Rheum Dis 2001; 60:1070-3.
44. Enomoto, H., I. Inoki, K. Komiya, et al., Vascular endothelial growth factor isoforms and their receptors are expressed in human osteoarthritic cartilage. Am J Pathol 2003; 162:171-81.
45. Matsumoto, T., G. M. Cooper, B. Gharaibeh, et al., Cartilage repair in a rat model of osteoarthritis through intraarticular transplantation of muscle-derived stem cells expressing bone morphogenetic protein 4 and soluble Flt-1. Arthritis Rheum 2009; 60:1390-405.
46. Kubo, S., G. M. Cooper, T. Matsumoto, et al., Blocking vascular endothelial growth factor with soluble Flt-1 improves the chondrogenic potential of mouse skeletal muscle=derived stem cells. Arthritis Rheum 2009; 60:155-65.
47. Maes, C., I. Stockmans, K. Moermans, et al., Soluble VEGF isoforms are essential for establishing epiphyseal vascularization and regulating chondrocyte development and survival. J Clin Invest 2004; 113:188-99.
48. Gerber, H. P., T. H. Vu, A. M. Ryan, et al., VEGF couples hypertrophic cartilage remodeling, ossification and angiogenesis during endochondral bone formation. Nat Med 1999; 5:623-8.
49. Ahmed, N., R. Dreier, A. Gopferich, et al., Soluble signalling factors derived from differentiated cartilage tissue affect chondrogenic differentiation of rat adult marrow stromal cells. Cell Physiol Biochem 2007; 20:665-78.
50. Fischer, J., A. Dickhut, M. Rickert, et al., Human articular chondrocytes secrete parathyroid hormone-related protein and inhibit hypertrophy of mesenchymal stem cells in coculture during chondrogenesis. Arthritis Rheum 2010; 62:2696-706.
51. Bian, L., D. Y. Zhai, R. L. Mauck, et al., Coculture of human mesenchymal stem cells and articular chondrocytes reduces hypertrophy and enhances functional properties of engineered cartilage. Tissue Eng Part A 2011; 17:1137-45.
52. Hildner, F., S. Concaro, A. Peterbauer, et al., Human adipose-derived stem cells contribute to chondrogenesis in coculture with human articular chondrocytes. Tissue Eng Part A 2009; 15:3961-9.
53. Goldring, M. B., K. Tsuchimochi, K. Ijiri, The control of chondrogenesis. J Cell Biochem 2006; 97:33-44.
54. Kavalkovich, K. W., R. E. Boynton, J. M. Murphy, et al., Chondrogenic differentiation of human mesenchymal stem cells within an alginate layer culture system. In Vitro Cell Dev Biol Anim 2002; 38:457-66.
55. Estes, B. T., B. O. Diekman, J. M. Gimble, et al., Isolation of adipose-derived stem cells and their induction to a chondrogenic phenotype. Nat Protoc 2010; 5:1294-311.
56. Diekman, B. O., C. R. Rowland, D. P. Lennon, et al., Chondrogenesis of adult stem cells from adipose tissue and bone marrow: induction by growth factors and cartilage-derived matrix. Tissue Eng Part A 2010; 16:523-33.

TABLE 4

Primer Sequences

| Gene | Direction | Sequence |
|------|-----------|----------|
| Acan | Sense | GCT TCG CTG TCC TCA ATG C (SEQ ID NO: 1) |
|      | Antisense | AGG TGT CAC TTC CCA ACT ATC C (SEQ ID NO: 2) |
| Col2 | Sense | CGAGTATGGAAGCGAAGG (SEQ ID NO: 3) |
|      | Antisense | GCTTCTTCTCCTTGCTCTTGC (SEQ ID NO: 4) |
| Comp | Sense | AGT GAC AGC GAT GGT GAT GG (SEQ ID NO: 5) |
|      | Antisense | TCC CCG TCC TGG TCT TGG (SEQ ID NO: 6) |
| Pdgfa | Sense | GAGGAGACGGATGTGAGG (SEQ ID NO: 7) |
|       | Antisense | ACGGAGGAGAACAAAGACC (SEQ ID NO: 8) |
| Runx2 | Sense | TTGGACACCTTGGACGCTAATT (SEQ ID NO: 9) |
|       | Antisense | AGA GGC AGA AGT CAG AGG (SEQ ID NO: 10) |
| Sox9 | Sense | GTG GGA GCG ACA ACT TTA CC (SEQ ID NO: 11) |
|      | Antisense | ATC GGA GCG GAG GAGGAG (SEQ ID NO: 12) |
| Vegfa | Sense | GGACATCTTCCAGGAGTACC (SEQ ID NO: 13) |
|       | Antisense | CGTCTTGCTGAGGTAACC (SEQ ID NO: 14) |

Sense and antisense primers for FGF-2 were obtained from Qiagen: Product Name Rn_FGF2_1 SG QuantiTect Primer Assay NM_019305 Catalog #: QT00189035.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition for affecting chondrogenic gene expression when contacting a chondrocyte comprising injectable biodegradable polymeric hydrogel controlled-release microbeads, wherein the microbeads comprise mesenchymal stem cells and alginate, wherein alginate lyase is incorporated into the alginate, and wherein the expression, production, or secretion of an angiogenic factor or a hypertrophic factor or both by the mesenchymal stem cells is inhibited by contact with chondrogenic medium, or the expression, production, or secretion of a chondrogenic factor or an anti-hypertrophic factor or both by the mesenchymal stem cells is stimulated by contact with chondrogenic medium, and wherein the mesenchymal stem cells are obtainable by contact with a chondrogenic medium for 5 days.

2. The composition of claim 1, wherein the microbeads are about 200 micrometers or less in diameter.

3. The composition of claim 1, wherein the mesenchymal stem cells are adipose stem cells.

4. The composition of claim 3, wherein the angiogenic factor is VEGF-A or FGF-2, or a combination of both.

5. The composition of claim 3, wherein the hypertrophic factor is FGF-18.

6. The composition of claim 3, wherein the chondrogenic factor is TGF-β1, TGF-β2, TGF-β3, IGF-1, or PTHrP, or a combination thereof.

7. The composition of claim 3, wherein the anti-hypertrophic factor is Noggin.

8. The composition of claim 1, wherein the microbeads are a renewable reservoir for the angiogenic factor, hypertrophic factor, chondrogenic factor, or anti-hypertrophic factor, or a combination thereof, which are expressed, produced, or secreted by the mesenchymal stem cells.

9. The composition of claim 8, wherein the mesenchymal stem cells are adipose stem cells.

10. The composition of claim 1, wherein the mesenchymal stem cells are are conditioned with chondrogenic medium before the stem cells are encapsulated in the microbeads.

11. The composition of claim 1, wherein the mesenchymal stem cells are conditioned with chondrogenic medium after the stem cells are encapsulated in the microbeads.

* * * * *

SEQUENCE LISTING

<160> NUMBER OF SEQ ID NOS: 15

<210> SEQ ID NO 1
<211> LENGTH: 19

```
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 1
gcttcgctgt cctcaatgc                                                      19

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 2
aggtgtcact tcccaactat cc                                                  22

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 3
cgagtatgga agcgaagg                                                       18

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 4
gcttcttctc cttgctcttg c                                                   21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 5
agtgacagcg atggtgatgg                                                     20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 6
tccccgtcct ggtcttgg                                                       18

<210> SEQ ID NO 7
<211> LENGTH: 18
<212> TYPE: DNA
```

```
<213> ORGANISM: Artificial Sequence
<220> FEATURE:
<223> OTHER INFORMATION: Description of Artificial Sequence: note =
      synthetic construct

<400> SEQUENCE: 7
gaggagacgg atgtgagg                                                  18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 8
acggaggaga acaaagacc                                                 19

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 9
ttggacacct tggacgctaa tt                                             22

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 10
agaggcagaa gtcagagg                                                  18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 11
gtgggagcga caactttacc                                                20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 12
atcggagcgg aggaggag                                                  18

<210> SEQ ID NO 13
<211> LENGTH: 20
<212> TYPE: DNA
<213> ORGANISM: Artificial Sequence
```

```
<220> FEATURE:
<223> OTHER INFORMATION: Description of Artificial Sequence: note =
      synthetic construct

<400> SEQUENCE: 13
ggacatcttc caggagtacc                                                      20

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 14
cgtcttgctg aggtaacc                                                        18

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 15

Gly Gly Tyr Gly Pro Val Gly Leu Ile Gly Gly Lys
1               5                   10
```